United States Patent
Altschul et al.

(10) Patent No.: US 10,010,703 B2
(45) Date of Patent: *Jul. 3, 2018

(54) DRUG DEVICE CONFIGURED FOR WIRELESS COMMUNICATION

(71) Applicant: POP TEST ABUSE DETERRENT TECHNOLOGY LLC, Cliffside Park, NJ (US)

(72) Inventors: Randice Lisa Altschul, Cliffside Park, NJ (US); Neil David Theise, New York, NY (US); Razvan Andrei Ene, Vimercate (IT); Myron Rapkin, Indianapolis, IN (US); Rebecca O'Brien, Shell Knob, MO (US)

(73) Assignee: Pop Test Abuse Deterrent Technology, LLC, Cliffside Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/822,625

(22) Filed: Nov. 27, 2017

(65) Prior Publication Data

US 2018/0078747 A1 Mar. 22, 2018

Related U.S. Application Data

(62) Division of application No. 15/315,400, filed as application No. PCT/US2015/029042 on May 4, 2015, now Pat. No. 9,878,138.

(Continued)

(51) Int. Cl.
*A61M 31/00* (2006.01)
*G06F 19/00* (2018.01)
(Continued)

(52) U.S. Cl.
CPC .......... *A61M 31/002* (2013.01); *A61K 31/58* (2013.01); *A61K 45/06* (2013.01);
(Continued)

(58) Field of Classification Search
CPC ...... A61M 2205/3523; A61M 2205/52; A61M 2205/3303; A61M 5/1723
See application file for complete search history.

(56) References Cited

U.S. PATENT DOCUMENTS 4,436,094 A 3/1984 Cerami
4,953,552 A 9/1990 DeMarzo
(Continued)

FOREIGN PATENT DOCUMENTS

EP 0298020 1/1989
EP 2016898 1/2009
(Continued)

OTHER PUBLICATIONS

International Search Report for corresponding PCT Application No. PCT/US2015/029042 dated Sep. 10, 2015.
(Continued)

*Primary Examiner* — Emily Schmidt
(74) *Attorney, Agent, or Firm* — Caesar Rivise, PC

(57) ABSTRACT

This invention relates to an ingestible drug delivery device configured for wireless communication with other ingestible drug delivery devices.

8 Claims, 12 Drawing Sheets

Related U.S. Application Data

(60) Provisional application No. 62/124,208, filed on Dec. 11, 2014, provisional application No. 62/122,431, filed on Oct. 21, 2014, provisional application No. 62/122,205, filed on Oct. 14, 2014, provisional application No. 61/997,506, filed on Jun. 3, 2014.

(51) Int. Cl.
*A61K 45/06* (2006.01)
*A61K 31/58* (2006.01)
*A61B 5/00* (2006.01)

(52) U.S. Cl.
CPC ........ *G06F 19/3462* (2013.01); *A61B 5/4845* (2013.01); *A61M 2205/3523* (2013.01); *A61M 2205/3553* (2013.01); *A61M 2205/3569* (2013.01); *A61M 2205/50* (2013.01); *A61M 2205/52* (2013.01); *A61M 2205/8206* (2013.01); *A61M 2205/8268* (2013.01); *A61M 2230/005* (2013.01); *A61M 2230/20* (2013.01); *A61M 2230/201* (2013.01); *A61M 2230/208* (2013.01); *A61M 2230/50* (2013.01); *A61M 2250/00* (2013.01)

(56) References Cited

U.S. PATENT DOCUMENTS

| | | |
|---|---|---|
| 5,338,625 A | 8/1994 | Bates et al. |
| 5,347,186 A | 9/1994 | Konotchick |
| 5,497,772 A | 3/1996 | Schulman et al. |
| 5,589,932 A | 12/1996 | Garcia-Rubio et al. |
| 5,705,293 A | 1/1998 | Hobson |
| 6,075,199 A | 6/2000 | Wong |
| 6,170,485 B1 | 1/2001 | Orrico |
| 6,304,766 B1 | 10/2001 | Colvin, Jr. |
| 6,673,596 B1 | 1/2004 | Sayler et al. |
| 6,802,811 B1 | 10/2004 | Slepian |
| 6,929,636 B1 | 8/2005 | von alten |
| 7,027,134 B1 | 4/2006 | Garcia-Rubio et al. |
| 7,097,662 B2 | 8/2006 | Evans, III et al. |
| 7,118,531 B2 | 10/2006 | Krill |
| 7,125,382 B2 | 10/2006 | Zhou et al. |
| 7,212,110 B1 | 5/2007 | Martin et al. |
| 7,303,875 B1 | 12/2007 | Bock et al. |
| 7,658,736 B2 | 2/2010 | Von Alten |
| 7,665,601 B2 | 2/2010 | Portier |
| 8,425,492 B2 | 4/2013 | Herbert et al. |
| 8,518,022 B2 | 8/2013 | Trovato et al. |
| 8,636,648 B2 | 1/2014 | Gazdzinski |
| 8,986,677 B2 | 3/2015 | Altschul et al. |
| 9,327,076 B2 | 5/2016 | Trovato et al. |
| 9,878,138 B2 | 1/2018 | Altschul et al. |
| 9,878,139 B2 | 1/2018 | Altschul et al. |
| 2002/0037925 A1* | 3/2002 | Dewey ............... A61K 31/00 514/561 |
| 2002/0173745 A1 | 11/2002 | Santini |
| 2003/0052788 A1 | 3/2003 | Chung |
| 2003/0152823 A1 | 8/2003 | Heller |
| 2004/0019464 A1 | 1/2004 | Martucci |
| 2004/0193020 A1 | 9/2004 | Chiba et al. |
| 2005/0143787 A1 | 6/2005 | Boveja et al. |
| 2005/0147559 A1 | 7/2005 | von Alten |
| 2005/0228259 A1 | 10/2005 | Glukhovsky et al. |
| 2006/0130828 A1* | 6/2006 | Sexton ................ A61M 15/00 128/200.14 |
| 2006/0234369 A1 | 10/2006 | Sih |
| 2008/0132881 A1 | 6/2008 | Wood |
| 2008/0188837 A1 | 8/2008 | Belsky et al. |
| 2009/0015022 A1 | 1/2009 | Rome et al. |
| 2009/0056328 A1 | 3/2009 | Kao |
| 2009/0118579 A1 | 5/2009 | Duerschinger |
| 2009/0149839 A1* | 6/2009 | Hyde ................... A61B 1/041 604/890.1 |
| 2009/0306633 A1* | 12/2009 | Trovato ............... A61B 1/041 604/891.1 |
| 2010/0049021 A1 | 2/2010 | Jina et al. |
| 2010/0076524 A1 | 3/2010 | Forsberg et al. |
| 2010/0121315 A1 | 5/2010 | Trovato |
| 2011/0009715 A1* | 1/2011 | O'Reilly ............. G06F 19/3456 600/302 |
| 2012/0101440 A1* | 4/2012 | Kamen ............... A61B 17/3415 604/164.08 |
| 2013/0073312 A1* | 3/2013 | Thompson .......... G06F 19/3462 705/2 |
| 2013/0310726 A1* | 11/2013 | Miller ................... A61M 1/288 604/5.04 |
| 2014/0309505 A1* | 10/2014 | Euliano ................ A61B 5/4833 600/302 |
| 2015/0343144 A1 | 12/2015 | Altschul et al. |
| 2016/0030761 A1 | 2/2016 | Butters |
| 2016/0038675 A1 | 2/2016 | Estes |

FOREIGN PATENT DOCUMENTS

| | | |
|---|---|---|
| WO | WO 2003/048998 | 6/2003 |
| WO | WO 2003/106966 | 12/2003 |
| WO | WO 2007/148238 | 12/2007 |

OTHER PUBLICATIONS

2015 National Drug Threat Assessment Summary, U.S. Department of Justice Drug Enforcement Administration, Oct. 2015.

Bernstein, et al. "How Drugs Intended for Patients Ended Up in the Hands of Illegal Users: 'No One Was Doing Their Job.'" The Washington Post, Oct. 22, 2016.

Bronzino, Joseph D. "The Biomedical Engineering Handbook." Preface. Second Edition, 2000.

Bugdett, et al. "Novel Technology for the Provision of Power to Implantable Physiological Devices." J Appl Physiol 102:1658-1663, 2007.

Chen, et al., "A Miniature Biofuel Cell." J. Am. Chem. Soc., 2001, 123, 8630-8631.

Durick, et al., "Cellular Biosensors for Drug Discovery." Biosens Bioelectron., Sep. 2001;16(7-8):587-92. Abstract.

Fan, et al., "Sensitive Optical Bionsensors for Unlabeled Targets: A Review." Anal Chim Acta., Jul. 14, 2008;620(1-2):8-26. Abstract.

Hagleitner, et al. "Smart Single-Chip Gas Sensor Microsystem." Nature 414, 293-296 (Nov. 15, 2001). Abstract.

Hermanides, et al., "Sense and Nonsense in Sensors." Diabetologia (2010) 53:593-596.

Hones et al., "The Technology Behind Glucose Meters: Test Strips." Diabetes Technology & Therapeutics. May 2008, 10(s1): S-10-S-26. Abstract.

Lavrik et al., "Cantilever Transducers as a Platform for Chemical and Biological Sensors", Review of Scientific Instruments, vol. 75, No. 7, pp. 2229-2253, Jul. 2004.

Li, et al., "Development of Novel Glucose Sensing Fluids with Potential Application to Microelectromechanical Systems-Based Continuous Glucose Monitoring", Journal of Diabetes Science and Technology, vol. 2, Issue 6, pp. 1066-1074, Nov. 2008.

Martindale W., "Martindale the Extra Pharmacopoeia", 31st Edition, Aug. 1996. Abstract.

Mattley et al., "Blood Characterization Using UV/vis Spectroscopy", Proc. SPIE 2388, Advances in Fluorescence Sensing Technology II, 462 (May 8, 1995). Abstract.

Mok, et al., "Recent Progress in Nucleic Acid Aptamer-Based Biosensors and Bioassays", Sensors 2008, 8, 7050-7084.

Moore, B., "The Potential Use of Radio Frequency Identification Devices for Active Monitoring of Blood Glucose Levels", Journal of Diabetes Science and Technology, vol. 3, Issue 1, pp. 180-183, Jan. 2009.

Morrison et al., "Clinical Applications of Micro- and Nanoscale Biosensors", Biomedical Nanostructures, pp. 433-454, 2008.

Nielsen et al., "Clinical Evaluation of a Transcutaneous Interrogated Fluorescence Lifetime-Based Microsensor for Continuous Glucose Reading", Journal of Diabetes Science and Technology, vol. 3, Issue 1, pp. 98-109, Jan. 2009.

(56) References Cited

OTHER PUBLICATIONS

Physicians' Desk Reference, 2006 (60th Library/Hospital Edition), Overview.
Qi et al., "Piezoelectric Ribbons Printed onto Rubber for Flexible Energy Conversion", Nano Lett. Feb. 10, 2010;10(2):524-8. Abstract.
Remington et al., "Remington's Pharmaceutical Sciences", 1990, Publication Summary.
Schmidt, et al., "Microbial Biosensor for Free Fatty Acids Using an Oxygen Electrode Based on Thick Film Technology", Abstract, Biosens Bioelectron. 1996; 11(11):1139-45.
Snow et al., "Chemical Detection With a Single-Walled Carbon Nanotube Capacitor", Science, vol. 307, pp. 1942-1945, Mar. 25, 2005.
Title II of the Drug Quality and Security Act, Drug Supply Chain Security, Food and Drug Administration, Jan. 1, 2015, http://www.fda.gov/Drugs/DrugSafety/DrugIntegrityandSupplyChainSecurity/DrugSupplyChainSecurityAct/ucm376829.htm.
Pharmacist Kian Gohari in Manhattan Federal Court for Conspiring to Distribute Oxycodone and Conspiring to Commit Healthcare Fraud, The United States Attorneys Office South District of New York, Nov. 16, 2016, https://www.justice.gov/usao-sdny/pr/pharmacist-kian-gohari-convicted-manhattan-federal-court-conspiring-distribute.
Vahist, S. Kumar, "A Review of Microcantilevers for Sensing Applications", AZojomo Journal of Materials Online, Jun. 18, 2007.
Wacharasindu, et al. "Radioisotope Microbattery Based on Liquid Semiconductor", Appl. Phys. Lett 95, 014103 (2009).
Wadum et al., "Fluorsecently Labelled Bovine acyl-CoA-binding Protein Acting as an acyl-CoA Sensor: Interaction with CoA and acyl-CoA Esters and its Use in Measuring Free acyl-CoA Esters and Non-esterified Fatty Acids", Biochem. J. (2002) 365, 165-172.
Yang et al., "On-Chip Electrochemical Impedance Spectroscopy for Biosensor Arrays", IEEE Sensors 2006, EXCO, Daegu, Korea, Oct. 22-25, 2006.
Yang et al., "Converting Biomechanical Energy into Electricity by a Muscle-Movement-Driven Nanogenerator", Nano Lett., 2009, 9 (3)m pp. 1201-1205.
Yang et al., "Power Generation with Laterally Packed Piezoelectric Fine Wires", Nature Nanotechnology 4, 34-39 (2009).
Yusa et al., "Controlled Multiple Quantum Coherences of Nuclear Spin in a Nonometre-Scale Device", Nature 434, 1001-1005 (Apr. 21, 2005).
Declaration of Randice Lisa Altschul Under 37 C.F.R. 1.132 filed in U.S. Appl. No. 14/703,163, now U.S. Pat. No. 9,662,392.
Declaration of Michael Mazzilli Under 37 C.F.R. 1.132 filed in U.S. Appl. No. 14/703,163, now U.S. Pat. No. 9,662,392.
Supplementary European Search Report for related European Patent Application No. EP15803922 dated Dec. 22, 2017.
Supplementary European Search Report dated Dec. 22, 2017.

\* cited by examiner

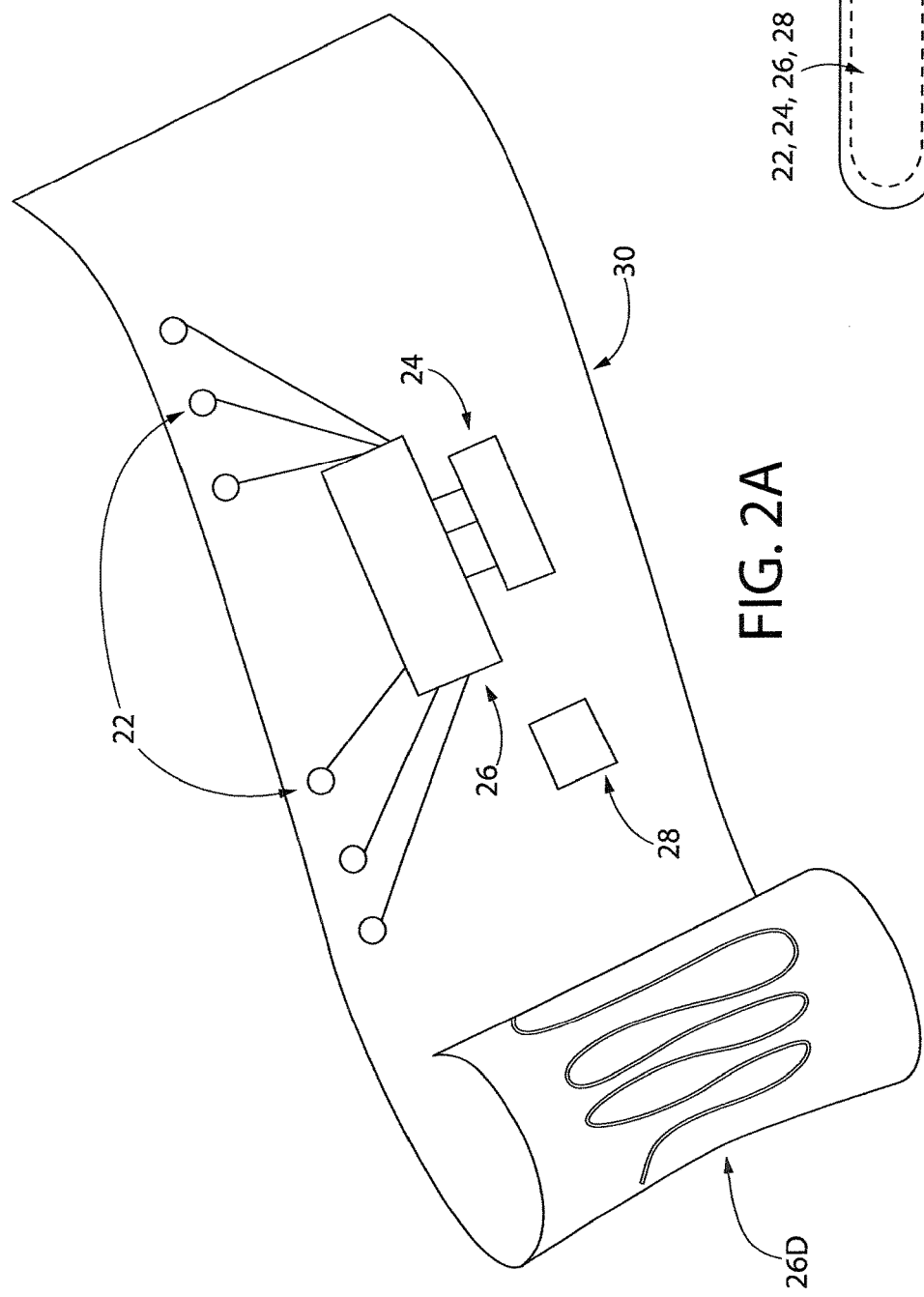
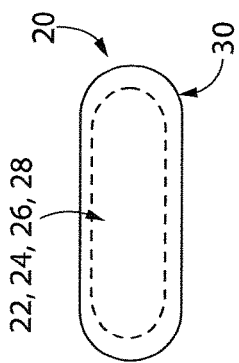
FIG. 2A
FIG. 2B

DRUG DEVICE CONFIGURED FOR WIRELESS COMMUNICATION

CROSS-REFERENCE TO RELATED APPLICATIONS

This Divisional application claims the benefit under 35 U.S.C. § 121 of application Ser. No. 15/315,400 filed on Dec. 1, 2016 which in turn is a U.S. national phase application that claims the benefit under 35 U.S.C. § 371 of PCT Application No. PCT/US2015/029042 filed on May 4, 2015 which in turn claims the benefit under 35 U.S.C. § 119(e) to: U.S. Provisional Application Ser. No. 61/997,506 filed Jun. 3, 2014; U.S. Provisional Application Ser. No. 62/122,205, filed Oct. 14, 2014, U.S. Provisional Application Ser. No. 62/122,431, filed Oct. 21, 2014, U.S. Provisional Application Ser. No. 62/124,208, filed Dec. 11, 2014, all of which are incorporated herein by reference in their entireties.

BACKGROUND OF THE INVENTION

Field of Invention

This invention relates to an ingestible drug delivery device configured for wireless communication with other ingestible drug delivery devices and the storage of provenance data of the drug delivery device therein.

According to the CDC, a poisoning occurs when a person's exposure to a natural or manmade substance has an undesirable effect. A drug poisoning occurs when that substance is an illegal, prescription, or over-the-counter drug. Most fatal poisonings in the United States result from drug poisoning.

Poisoning can be classified as:
self-harm or suicide when the person wants to harm himself;
assault or homicide when the person wants to harm another; and
Unintentional, also known as "accidental," when no harm is intended. Unintentional drug poisoning includes drug overdoses resulting from drug misuse, drug abuse, and taking too much of a drug for medical reasons.

Drug overdose death rates in the United States have never been higher. Drug overdose death rates have risen steadily in the United States since 1970.
In 2007, 27,658 unintentional drug overdose deaths occurred in the United States.
Drug overdose deaths were second only to motor vehicle crash deaths among leading causes of unintentional injury death in 2007 in the United States.
The increase in drug overdose death rates is largely because of prescription opioid painkillers
Among deaths attributed to drugs, the most common drug categories are cocaine, heroin, and a type of prescription drug called opioid painkillers.
"Opioids" are synthetic versions of opium. They have the ability to reduce pain but can also suppress breathing to a fatal degree when taken in excess. Examples of opioids are oxycodone (OxyContin®), hydrocodone (Vicodin®), and methadone.
There has been at least a 10-fold increase in the medical use of opioid painkillers during the last 20 years because of a movement toward more aggressive management of pain.
Because opioids cause euphoria, they have been associated increasingly with misuse and abuse. Opioids are now widely available in illicit markets in the United States.

There is a need to perfect a "Smart Pill" to prevent deaths by overdose. The answer to this need rests in the present invention which provides for a unique and proprietary capsule with the capability to "know" when there is a prescribed dosage of a certain constituent in the body and prevent any additional dosage to be released into the body.

Sustained and extended release capsules have been available in the pharmaceutical industries for years but they do not prevent the release of a certain constituent into the body, instead they just prolong the time in which it would be released. This does not solve the problem of overdosing.

The present invention addresses the problem of overdosing, amongst other problems by providing the Smart Pill System. The smart pill system comprises several technologies (e.g., silicon, sensors, peer wireless communication), different devices (e.g., pill itself, enabling terminals), and an encrypted network for communication and data storage. The system is able to ensure reasonable anti-counterfeit and origin traceback, with a multilayered security system, and good overdose protection. On the top of the present system one can build a full system of diagnoses, follow-up, automatic dosage, and health management.

The smart pill itself is a self-contained electronic device with, e.g., a micro controller, memory, wireless communication capabilities, onboard sensors, and a Micro-Electro-Mechanical System (MEMS) drug delivery system. The devices can communicate with the pill are called programming terminals which are may be linked to a central database using a protected encrypted network. The central database stores, e.g., all the relevant pill information, tracks and enables its uses at all levels from manufacturer to patient, makes possible expiring date tracking and prevents unauthorized use of the pills. The smart pill comprises e.g., a printed flex circuit contain the micro controller with Flash memory, sensors, One Time Programmable memory, wireless communication and antenna, wrapped around drug compartment, e.g., MEMS pump, and battery.

The smart pill has a built in sensor that knows when one or more additional smart pills are in the body and if they are detected, the "API" Active Pharmaceutical Ingredient (which also include drug product that includes API and buffers, etc.) will not be released. Thru Micro-encapsulation the present invention uses a programmable sensor. The sensor is programmed via RF or other means to tell the sensor in each capsule the prescribed dosage. i.e.: 200 mg in a 4 hour period. Each capsule knows when another capsule is in the body via the sensors contained therein. The Drug Company or the Pharmacist would preset the pill to know what its prescribed dosage is. The patient would take his prescribed dosage of one or more pills. The sensors detect one another and also detect that they are the only two pills in the body and thus release the API into the system. The release of API can be through a variety of means; osmotic plug piston, polymer cracking or trigger initiated solubilization on the capsule itself or other capsule voids, release from ion-bound linkage from polymer side chains to release the API. Another embodiment of the present invention, one which could be pharmacist controlled is by controlling the release of the active ingredient: release/pump it in the dissolving part of the pill, neutralize/block the active part. The smart Capsule can also be obtained by: sealing the passage to the dissolving part, neutralizing the active part by "cement" it in an inert material and chemically or physically (temperature/light etc) neutralize the active ingredient. Another embodiment of the present invention in a pump form which could be controlled for different scenarios (e.g., emergencies, environmental changes, etc.) could also be described like two electrodes in water. The water compartment has a flexible wall. If you start making the water electrolyze you will obtain gases, which will increase the volume and press outward the flexible wall (or a piston). Thus no motor is required in this embodiment; where an electrolytic activation is utilized, the process is reversible, i.e., by reversing the current oxygen and hydrogen recombine to form water, thus decreasing volume.

If the patient takes an additional quantity of pills (one or more than prescribed dosage) the new pills entering the system will detect the presence of the previous pills that have already released their API load and may also detect the quantity of metabolites. The detection can be made via RF signal, pH, acidity level, detection of drug or metabolites presence, etc. If the detection of released capsules is made by the newly entering capsules, those capsules will not release their API into the system and instead travel through the body as whole units and be released through the anus in the feces. No further API would be released into the system unless the sensor detects that it is the prescribed time of entry, timed drug half-life, sensor detected drug depletion (initial drug and/or metabolites). Batteries if needed can be encapsulated so as to not be a material threat to the patient.

The Smart Pills can also detect other API's, drugs of abuse; alcohol; pregnancy and can prevent release of teratogenic APIs when the patient is determined to be pregnant. The Smart Pills can also use a variety of sensors including but not limited to electronic, biological, chemical, harmonic, and digital sensors.

Smart Pills can be preprogrammed by the manufacturer and/or the pharmacist to prevent drug interactions. i.e.: a drug is taken by the patient and either intentionally or in error another drug which should not be combined with the first drug is taken. The second drug detects the first drug and the API is not released into the system. Smart Pills could also be preprogrammed by the pharmacist to know the patient. The capsules recognize certain features about the patient's physiology and would only release the API into the system of the prescribed user, thus preventing unauthorized usage by others who are not prescribed the drug.

Smart Pills can also be made in pill, tablet, and a variety of other packaging for home or clinical usage, whether through administration by intravenous, oral, rectal, etc. All embodiments are for use with humans as well as animals and have application in agricultural use too.

This invention further relates to an attachable device for retail packaging configured for wireless communication with other retail packages with the devices. In exemplary embodiments, the smart pill system incorporates this technology.

Retail packages are conveniently placed upon retail shelves but they need human interaction to take inventory of the shelves and to stock the shelves. If the human is not diligent the shelf can remain empty and the consumer would not be able to purchase the desired product.

Many high tech endeavors have been applied to this problem including but not limited to wireless devices on the shelves themselves, wireless devices to scan bar codes on the packages and human tallying of the items themselves usually with bar code readers.

All of the above works but tend to be very costly and only the high end retailer can afford to structure the retail environment with the technology. The present invention levels the playing field and makes the technology available to every retail establishment that has access to a "Smart Phone", a tablet or a computer through the use of an Inventory Application ("APP") that maintains the data being sent by the wireless devices. The Present Invention consists of a digital tag that is attached or made a part of each package, label, etc. It can incorporate or be made a part of the UPC Bar Code and retains that information as part of its digital signature. The human who maintains the inventory simply walks by the shelves and receives a signal that the package on the shelf transmits. The tags also speak to one another when they arrive on the shelf to determine quantity on the shelf. This information is also wirelessly sent to the APP.

All references cited herein are incorporated herein by reference in their entireties.

BRIEF SUMMARY OF THE INVENTION

The invention provides an ingestible drug delivery device configured for wireless communication with other ingestible drug delivery devices, said drug delivery device comprising: a capsule body comprising: a sensor for sensing at least one biologic condition within a patient and providing a first signal representative thereof; a bioactive substance module comprising a container for holding a volume and/or quantity of bioactive substance therein and a microactuator for dispensing said bioactive substance from said container to a location outside of said capsule body; an electronics module, coupled to said sensor and said bioactive substance module, said electronics module comprising a processor, a transponder and a memory (e.g., flash, OTP, etc.), said memory comprising data selected from the group consisting of: (a) data related to the patient who is permitted to ingest said ingestible drug medical device; (b) data related to said bioactive substance; (c) data related to a healthcare provider that enabled said electronics module; (d) data related to said sensor; (e) data related to the provenance of said ingested drug medical device; (f) combinations thereof, a power source coupled to said sensor, said bioactive substance module and said electronics module; and wherein said processor controls said transponder to transmit at least one wireless signal and to receive at least one wireless signal from at least one other ingestible medical device, and wherein said processor receives said first signal and analyzes said first signal with all of said data along with said received at least one wireless signal for controlling said microactuator for dispensing said bioactive substance.

The invention provides an ingestible drug delivery device wherein said data related to the patient who is permitted to ingest said ingestible drug delivery device comprises the identification of the patient.

The invention provides an ingestible drug delivery device wherein said data related to the patient who is permitted to ingest said ingestible drug delivery device comprises the medical conditions of the patient.

The invention provides an ingestible drug delivery device wherein the healthcare provider is selected from the group consisting of a doctor, physician's assistant, nurse, pharmacist, physical therapist, and dentist.

The invention provides an ingestible drug delivery device wherein said data related to said healthcare provider that enabled said processor of said ingested drug delivery device comprises a digital signature of said healthcare provider.

The invention provides an ingestible drug delivery device further comprising an interlock, said interlock preventing the dispensing of said bioactive substance if said processor determines that whoever ingested said ingestible drug delivery device is not the patient that is permitted to ingest said ingestible drug delivery device.

The invention provides an ingestible drug delivery device wherein said volume of bioactive substance comprises an active pharmaceutical ingredient (API) and wherein said ingestible drug delivery device comprises a rupture detection mechanism that causes said API to deactivate if said ingestible drug delivery device is tampered with.

The invention provides an ingestible drug delivery device wherein said sensor is capable of detecting the concentration of bioactive substance in the patient, and can prevent release of additional bioactive substance when contraindicated.

The invention provides an ingestible drug delivery device wherein said sensor is capable of detecting pregnancy, and can prevent release of bioactive substance when the patient is determined to be pregnant.

The invention provides an ingestible drug delivery device wherein said sensor is selected from the group consisting of electronic, biological, chemical, digital sensors, and combinations thereof.

The invention provides an ingestible drug delivery device wherein said sensor is selected from the group consisting of a pH sensor, a temperature sensor, a glucose sensor, a pregnancy sensor, a drug sensor, a phenylalanine sensor, and combinations thereof.

The invention provides an ingestible drug delivery device wherein said sensor comprises a drug sensor for analytes selected from the group consisting of alcohol, nicotine, caffeine, cocaine (including crack cocaine), *cannabis*, amphetamines (including crystal methamphetamine), opiates and opiate analogues (including heroine, oxycodone, hydrocodone, hydromorphone, methadone), dextromethorphan, benzodiazepines, ecstasy (MDMA), GHB, barbiturates, khat, kratom, PCP, LSD, ketamine, peyote, mescaline, psilocybin, rohypnol, *Salvia divinorum*, antidepressants, anti-anxiety medications, sleep aids, allergy medications, and combinations thereof, and can prevent release of bioactive substance when contraindicated.

The invention provides an ingestible drug delivery device wherein the bioactive substance has abuse resistant technology.

The invention provides an ingestible drug delivery device wherein the ingestible drug delivery device is configured to track the drug delivery device from manufacturer to the patient, to enable a health care provider to determine the origin of the drug delivery device, to confirm that at least one of the right type and the right dosage of the medication was delivered to the patient, and/or to enable the ingestible drug delivery device to release at least one bioactive substance to the patient, the ingestible drug delivery device comprising: an electronics module capable of receiving data, wherein the electronics module is operative to perform at least one function selected from the group consisting of: receiving a unique identity for the ingestible drug delivery device, wherein the ingestible drug delivery device comprises the unique identity that is associated with at least one of the manufacturer and the medication; receiving information from a patient interface device in communication with the ingestible drug delivery device and the patient, wherein at the time the patient takes the ingestible drug delivery device, the patient interface device is operative to detect the unique identity associated with the ingestible drug delivery device and confirm delivery of the medication to the patient, that optionally enables the release of at least one bioactive substance to a patient; receiving information related to the patient who is permitted to ingest said ingestible drug delivery device comprises the identification of the patient, that optionally enables the release of at least one bioactive substance to a patient; receiving information from data related to a healthcare provider that enables the release of at least one bioactive substance to the patient; and/or receiving the detected unique identity associated with the ingestible drug delivery device detected via a patient interface device and the confirmation of delivery of the medication to the patient via the ingestible drug delivery device, that optionally enables the release of at least one bioactive substance to a patient; and combinations thereof, wherein the processor is operative to confirm the origin of the medication and the type of the medication based at least on the unique identity of the ingestible drug delivery device, to track the drug delivery device from manufacturer to the patient, to enable a health care provider to determine the origin of the drug delivery device, to confirm that at least one of the right type and the right dosage of the medication was delivered to the patient, and/or to enable the ingestible drug delivery device to release at least one bioactive substance to the patient, and optionally, wherein the ingestible drug delivery device further comprises an interlock, said interlock preventing the dispensing of said bioactive substance if said processor determines that whomever ingested said ingestible drug delivery device is not the patient that is permitted to ingest said ingestible drug delivery device.

The invention provides an ingestible drug delivery device wherein the processor is operative to communicate with a datacenter database to, at least, retrieve medical information about the patient and provide information related to the medication to be administered to the patient.

The invention provides an ingestible drug delivery device wherein the processor is operative to validate at least one of the type and dosage selected by the health care provider prior to dispensing the medication to the patient.

The invention provides an ingestible drug delivery device wherein the processor is operative to communicate with an interrogation unit, wherein the interrogation unit is operative to interrogate the ingestible drug delivery device and receive the unique identity of the ingestible drug delivery device to confirm the origin of the medication and the type of the medication, wherein the computer is operative to interrogate the ingestible drug delivery device and receive the unique identity of the identifier from the ingestible drug delivery device.

The invention provides an ingestible drug delivery device wherein the processor is operative to prevent release of the bio-active substance.

The invention provides an ingestible drug delivery device wherein the processor is operative to receive biometric parameters from the patient interface device, wherein the biometric parameters can identify the patient.

The invention provides an ingestible drug delivery device wherein the ingestible drug delivery device further comprises a deactivation module comprising a container for holding a volume and/or quantity of a deactivator and a microactuator for dispensing said deactivator to said bioactive substance module, wherein the deactivator module is coupled to said bioactive substance module, and wherein the electronics module is coupled to said deactivator module, said electronics module comprising a processor, a transponder and a memory.

The invention provides an ingestible drug delivery device wherein the ingestible drug delivery device further comprises a deactivation module comprising a container for holding a volume and/or quantity of a deactivator and a microactuator for dispensing said deactivator to said patient, wherein the deactivation substance is selected from the group consisting of an antagonist to the bioactive substance, and a pharmaceutical.

The invention provides a method for preventing accidental or intentional overdosing of at least one bioactive substance, said method comprising: (a) forming an ingestible drug delivery device having a sensor for sensing at least one biologic condition within a patient and providing a first signal representative thereof; a bioactive substance module comprising a container for holding a volume and/or quantity of bioactive substance therein and a microactuator for dispensing said bioactive substance from said container to a location outside of said capsule body; an electronics module, coupled to said sensor and said bioactive substance module, said electronics module comprising a processor, a transponder and a memory, said memory comprising capsule data that comprises data selected from the group consisting of: data related to the patient who ingested said ingestible drug medical device; data related to said bioactive substance; data related to a healthcare provider that enabled said processor; data related to said sensor; data related to the provenance of said ingested drug medical device; and combinations thereof a power source coupled to said sensor, said bioactive substance module and said electronics module; (b) upon ingesting said ingestible drug delivery device, listening, by said processor, for at least one wireless signal from any other ingested drug delivery device and if no said at least one wireless signal is received within a predetermined period, said processor declaring itself a master drug delivery device and moving to step (c), and if said at least one wireless signal is received within said predetermined period, said processor wirelessly transmits an identification signal and halts any dispense process and continues to listen for another wireless signal; and (c) analyzing said first signal with said capsule data for controlling said microactuator for dispensing said bioactive substance.

The invention provides a method further comprising the step of said master drug delivery device transmitting a wireless signal, following transmission of said at least one wireless signal, at a predetermined interval and then listening for any response signal from any other ingested drug delivery device.

The invention provides a method further comprising the step of said processor of said master drug delivery device determining whether the large intestine has been entered or whether eight hours has elapsed since ingestion.

The invention provides a method further comprising the step of said processor of said master drug delivery device storing the identification and receipt time of any identification signal received by said processor.

The invention provides a method further comprising the step of said processor of said master drug delivery device organizing the identifications of a plurality of ingested drug delivery devices based upon said respective receipt times of respective identification signals to form drug delivery device data.

The invention provides a method further comprising the step of said processor of said master drug delivery device communicating with the ingested drug delivery device whose receipt time was closest to the ingestion of said master drug delivery device.

The invention provides a method further comprising the step of said processor of said master drug delivery device reaching either the large intestine or whether said eight hours has elapsed, whichever occurs first, and conferring to said ingested drug delivery device, whose receipt time was closest to the ingestion of said master drug delivery device, a title of new master drug delivery device along with said drug delivery device data, said original master drug delivery device shutting down permanently.

The invention provides a method further comprising the step of said new master drug delivery device analyzing said first signal with said capsule data for controlling said microactuator for dispensing said bioactive substance.

The invention provides a method wherein said data related to the patient who is permitted to ingest said ingestible drug delivery device comprises the identification of the patient.

The invention provides a method wherein said data related to the patient who is permitted to ingest said ingestible drug delivery device comprises the medical conditions of the patient.

The invention provides a method wherein the healthcare provider is selected from the group consisting of a doctor, a physician's assistant, nurse, pharmacist, physical therapist, and dentist.

The invention provides a method wherein said data related to said healthcare provider that enabled said processor of said ingested drug delivery device comprises a digital signature of said healthcare provider.

The invention provides a method further comprising the step of preventing the dispensing of said bioactive substance if said processor determines that whomever ingested said ingestible drug delivery device is not the patient that is permitted to ingest said ingestible drug delivery device.

The invention provides a method wherein said volume of bioactive substance comprises an active pharmaceutical ingredient (API) and further comprising step of deactivating said API if said ingestible drug delivery device is tampered with.

The invention provides a method wherein said sensor is capable of detecting the concentration of bioactive substance in the patient, and can prevent release of additional bioactive substance when contraindicated.

The invention provides a method wherein said sensor is capable of detecting pregnancy, and prevents release of bioactive substance when the patient is determined to be pregnant.

The invention provides a method wherein said sensor is selected from the group consisting of electronic, biological, chemical, digital sensors, and combinations thereof.

The invention provides a method wherein said sensor is selected from the group consisting of a pH sensor, a temperature sensor, a glucose sensor, a pregnancy sensor, a drug sensor, a temperature sensor, a phenylalanine sensor, and combinations thereof.

The invention provides a method wherein said sensor comprises a drug sensor for analytes selected from the group consisting of alcohol, nicotine, caffeine, cocaine (including crack cocaine), *cannabis*, amphetamines (including crystal methamphetamine), opiates and opiate analogues (including heroine, oxycodone, hydrocodone, hydromorphone, methadone), dextromethorphan, benzodiazepines, ecstasy (MDMA), GHB, barbiturates, khat, kratom, PCP, LSD, ketamine, peyote, mescaline, psilocybin, rohypnol, *Salvia divinorum*, antidepressants, anti-anxiety medications, sleep aids, allergy medications, and combinations thereof, and prevents release of additional bioactive substance when contraindicated.

The invention provides a method further comprising the step of preventing the dispensing of said bioactive substance if said processor determines that the patient that ingested a compound selected from the group consisting of alcohol, nicotine, caffeine, cocaine (including crack cocaine), *can-*

*nabis*, amphetamines (including crystal methamphetamine), opiates and opiate analogues (including heroine, oxycodone, hydrocodone, hydromorphone, methadone), dextromethorphan, benzodiazepines, ecstasy (MDMA), GHB, barbiturates, khat, kratom, PCP, LSD, ketamine, peyote, mescaline, psilocybin, rohypnol, *Salvia divinorum*, antidepressants, anti-anxiety medications, sleep aids, allergy medications, and combinations thereof wherein said sensor is capable of detecting the concentration of bioactive substance in the patient, and prevents release of additional bioactive substance when contraindicated.

The invention provides a method wherein the ingestible drug delivery device further comprises a deactivation module comprising a container for holding a volume and/or quantity of a deactivator and a microactuator for dispensing said deactivator to said bioactive substance module, wherein the deactivator module is coupled to said bioactive substance module, and wherein the electronics module is coupled to said deactivator module, said electronics module comprising a processor, a transponder and a memory.

The invention provides a method of tracking an ingestible drug delivery device from a manufacturer of the ingestible drug delivery device to a patient, track the drug delivery device from the manufacturer to a patient, to enable a health care provider to determine the origin of the drug delivery device, to confirm that at least one of the right type and the right dosage of the medication was delivered to the patient, and/or to enable the ingestible drug delivery device to release at least one bioactive substance to the patient, the ingestible drug delivery device comprising: an electronics module capable of receiving data, wherein the electronics module is operative to perform at least one function selected from the group consisting of: receiving a unique identity for the ingestible drug delivery device, wherein the ingestible drug delivery device comprises the unique identity that is associated with at least one of the manufacturer and the medication; receiving information from the patient interface device in communication with the ingestible drug delivery device and the patient, wherein at the time the patient takes the ingestible drug delivery device, the patient interface device is operative to detect the unique identity associated with the ingestible drug delivery device and confirm delivery of the medication to the patient, that optionally enables the release of at least one bioactive substance to a patient; receiving information related to the patient who is permitted to ingest said ingestible drug delivery device comprises the identification of the patient, that optionally enables the release of at least one bioactive substance to a patient; receiving information from data related to a healthcare provider that enables the release of at least one bioactive substance to a patient; and/or receiving the detected unique identity associated with the ingestible drug delivery device detected via a patient interface device and the confirmation of delivery of the medication to the patient via the ingestible drug delivery device, that optionally enables the release of at least one bioactive substance to a patient; and combinations thereof, the method comprising the steps of: confirming the origin of the medication and the type of the medication based at least on the unique identity of the ingestible drug delivery device, to track the drug delivery device from manufacturer of the ingestible drug delivery device to the patient, to enable a health care provider to determine the origin of the drug delivery device, to confirm that at least one of the right type and the right dosage of the medication was delivered to the patient, and/or to enable the ingestible drug delivery device to release at least one bioactive substance to the patient, and optionally, preventing the dispensing of said bioactive substance if said processor determines that whomever ingested said ingestible drug delivery device is not the patient that is permitted to ingest said ingestible drug delivery device, wherein the ingestible drug delivery device further comprises an interlock.

The invention provides a method wherein the processor is operative to communicate with a datacenter database to at least one of retrieve medical information about the patient and provide information related to the medication to be administered to the patient.

The invention provides a method wherein the processor is operative to validate at least one of the type and dosage selected by the health care provider prior to dispensing the medication to the patient.

The invention provides a method wherein the processor is operative to communicate with an interrogation unit, wherein the interrogation unit is operative to interrogate the ingestible drug delivery device and receive the unique identity of the ingestible drug delivery device to confirm the origin of the medication and the type of the medication, wherein the computer is operative to interrogate the ingestible drug delivery device and receive the unique identity of the identifier from the ingestible drug delivery device.

The invention provides a method wherein the processor is operative to: prevent release of the bio-active substance.

The invention provides a method wherein the processor is operative to receive biometric parameters from the patient interface device, wherein the biometric parameters can identify the patient.

The invention provides a method wherein the ingestible drug delivery device further comprises a deactivation module comprising a container for holding a volume and/or quantity of a deactivator and a microactuator for dispensing said deactivator to said bioactive substance module, wherein the deactivator module is coupled to said bioactive substance module, and wherein the electronics module is coupled to said deactivator module, said electronics module comprising a processor, a transponder and a memory.

The invention provides a method wherein the ingestible drug delivery device further comprises a deactivation module comprising a container for holding a volume and/or quantity of a deactivator and a microactuator for dispensing said deactivator to said patient, wherein the deactivation substance is selected from the group consisting of an antagonist to the bioactive substance, and a pharmaceutical.

The invention provides a method for treating or preventing addiction, addiction induced anxiety, and/or withdrawal symptoms wherein said method comprises: (a) selecting a patient in need of treating or preventing addiction, addiction induced anxiety, and/or withdrawal symptoms; (b) providing at least one ingestible drug delivery device configured for wireless communication with other ingestible drug delivery devices, each of said drug delivery devices comprising: a capsule body comprising: a sensor for sensing at least one biologic condition within a patient and providing a first signal representative thereof; a bioactive substance module comprising a container for holding a volume and/or quantity of bioactive substance therein and a microactuator for dispensing said bioactive substance from said container to a location outside of said capsule body; an electronics module, coupled to said sensor and said bioactive substance module, said electronics module comprising a processor, a transponder and a memory, said memory comprising data selected from the group consisting of: (i) data related to the patient who is permitted to ingest said ingestible drug medical device; (ii) data related to said bioactive substance; (iii) data related to a healthcare provider that enabled said electronics module; (iv) data related to said sensor; (v) data related to the provenance of said ingested drug medical device, and combinations thereof; a power source coupled to said sensor, said bioactive substance module and said electronics module; and wherein said processor controls said transponder to transmit at least one wireless signal and to receive at least one wireless signal from at least one other ingestible medical device, and wherein said processor receives said first signal and analyzes said first signal with all of said data along with said received at least one wireless signal for controlling said microactuator for dispensing said bioactive substance; wherein the bioactive substance is at least one glucocorticoid receptor antagonist in a therapeutically effective amount; and (c) administering the ingestible delivery device to the patient, wherein addiction, addiction induced anxiety, and/or withdrawal symptoms are treated and/or prevented in the patient. The invention provides a method wherein the at least one glucocorticoid receptor antagonist is in a pharmaceutical preparation. The invention provides a method wherein the glucocorticoid receptor antagonist is selected from the group consisting of ORG 34517, 11-(substituted phenyl)-estra-4,9-diene derivatives, and 11-(substituted phenyl)-estra-4,9-diene derivatives of formula I

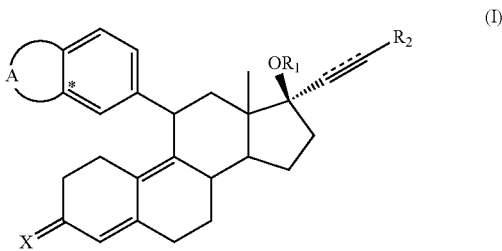

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond. The invention provides a method wherein the GCR antagonist is ORG34517.

The invention provides a method of treating or preventing addiction, addiction induced anxiety, and/or withdrawal symptoms in a patient in need thereof, comprising: (a) selecting a patient in need of treating or preventing addiction, addiction induced anxiety, and/or withdrawal symptoms; (b) providing at least one ingestible drug delivery device configured for wireless communication with other ingestible drug delivery devices, said drug delivery device comprising: a capsule body comprising: a sensor for sensing at least one biologic condition within a patient and providing a first signal representative thereof; a bioactive substance module comprising a container for holding a volume and/or quantity of bioactive substance therein and a microactuator for dispensing said bioactive substance from said container to a location outside of said capsule body; an electronics module, coupled to said sensor and said bioactive substance module, said electronics module comprising a processor, a transponder and a memory, said memory comprising data selected from the group consisting of: (i) data related to the patient who is permitted to ingest said ingestible drug medical device; (ii) data related to said bioactive substance; (iii) data related to a healthcare provider that enabled said electronics module; (iv) data related to said sensor; (v) data related to the provenance of said ingested drug medical device, and combinations thereof; a power source coupled to said sensor, said bioactive substance module and said electronics module; and wherein said processor controls said transponder to transmit at least one wireless signal and to receive at least one wireless signal from at least one other ingestible medical device, and wherein said processor receives said first signal and analyzes said first signal with all of said data along with said received at least one wireless signal for controlling said microactuator for dispensing said bioactive substance; wherein said bioactive substance is a composition comprising: i) a first therapeutic agent which is a GCR antagonist, or pharmaceutically acceptable salts thereof; ii) at least one or possibly more additional therapeutic agent(s) selected from the group consisting of anxiolytics, antidepressants, neuroleptics, or other psychotropic medications and combinations thereof; and iii) at least one pharmaceutically acceptable carrier, wherein the first and second therapeutic agents are each present in an amount which, in combination, is a therapeutically effective amount for treating or preventing addiction, addiction induced anxiety, and/or withdrawal symptoms; and (c) administering the ingestible drug delivery device to the patient, wherein addiction, addiction induced anxiety, and/or withdrawal symptoms are treated and/or prevented in the patient. The invention provides a method wherein the second therapeutic agent is selected from the group consisting of at least one anti-anxiety drug, at least one anti-depressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one anti-depressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof. The invention provides a method wherein the GCR antagonist is selected from the group consisting of ORG 34517, 11-(substituted phenyl)-estra-4, 9-diene derivatives, and 11-(substituted phenyl)-estra-4,9-diene derivatives of formula I

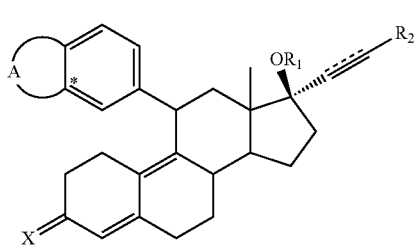

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond. The invention provides a method wherein the GCR antagonist is ORG34517.

The invention provides a method for treatment of withdrawal from narcotics and subsequent prevention of relapse of narcotic use in a patient in need of such treatment, said method comprising: (a) selecting a patient in need of treatment of withdrawal from narcotics and subsequent prevention of relapse of narcotic use; (b) providing an ingestible drug delivery device comprising: a sensor for sensing at least one biologic condition within a patient and providing a first signal representative thereof; a bioactive substance module comprising a container for holding a volume and/or quantity of bioactive substance therein and a microactuator for dispensing said bioactive substance from said container to a location outside of said capsule body; an electronics module, coupled to said sensor and said bioactive substance module, said electronics module comprising a processor, a transponder and a memory, said memory comprising capsule data that comprises data selected from the group consisting of: data related to the patient who ingested said ingestible drug medical device; data related to said bioactive substance; data related to a healthcare provider that enabled said processor; data related to said sensor; data related to the provenance of said ingested drug medical device, a combinations thereof; a power source coupled to said sensor, said bioactive substance module and said electronics module; (c) administering the at least one ingestible delivery device to the patient, wherein upon ingesting said ingestible drug delivery device, listening, by said processor, for at least one wireless signal from any other ingested drug delivery device and if no said at least one wireless signal is received within a predetermined period, said processor declaring itself a master drug delivery device and moving to step (c), and if said at least one wireless signal is received within said predetermined period, said processor wirelessly transmits an identification signal and halts any dispense process and continues to listen for another wireless signal; and d) analyzing said first signal with said capsule data for controlling said microactuator for dispensing said bioactive substance, wherein said bioactive substance is a composition comprising: i) a first therapeutic agent which is a GCR antagonist, or pharmaceutically acceptable salts thereof; ii) optionally separated from the first therapeutic agent, at least one or possibly more additional therapeutic agent(s) selected from the group consisting of opioid analgesics and combinations thereof; and iii) at least one pharmaceutically acceptable carrier, wherein the first and second therapeutic agents are each present in an amount which, in combination, is a therapeutically effective amount for treatment of withdrawal from narcotics and subsequent prevention of relapse of narcotic use in a patient in need of such treatment, wherein subsequent to the administration, the patient withdrawal from narcotics is treated and subsequent relapse of narcotic use is prevented. The invention provides a method wherein the second therapeutic agent is selected from the group consisting of at least one narcotic selected from the group consisting of opioid analgesics, morphine, codeine, buprenorphine, tramadol, fentany, hydromonorphone, morphine, oxycodone/naloxone, opiate, opium, acetyldihydrocodeine, alfentani, allylprodine, alphamethylfentanyl, alphaprodine, benzylmorphine, betaprodine, bezitriamide, buprenorphine, butorphanol, bremazocine, carfentan (carfentanyl), contin, dextromoramide, dextropropoxyphene, dezocine, diacetylmorphine, diamorphine, dihydrocodeine, dihydromorphine, dihydromorphone, diphenoxylate, dipipanone, enadoline, ethylketazocine, ethylmorphine, etonitazene, etorphine, fentanyl, heroin, hydrocodone, hydromorphin (hydromorphine), hydromorphone, ketazocine, ketobemidone, lefetamine, levomethadon, levomethadyl, levomethorphan, levor-phanol, loperamide, meperidine, meptazinol, methadone, methadyl, methylmorphine, morphin (morphine), nalbuphine, narcotic, nicocodeine, nicomorphine, normorphine, noscapin, ohmefentanyl, oripavine, oxycodone, oxycontin, oxymorphone, papaveretum, papaverin, pentazocine, percocet, peronine, pethidine, phenazocine, phencyclidine, pholcodine, piritramid (priitramidine), prodine, promedol, propoxyphene, remifentanil, sufentanil, tapentadol, thebaine, tilidine, tramadol, ultracet, and combinations thereof. The invention provides a method wherein the GCR antagonist is selected from the group consisting of ORG 34517, 11-(substituted phenyl)-estra-4,9-diene derivatives, and 11-(substituted phenyl)-estra-4,9-diene derivatives of formula I

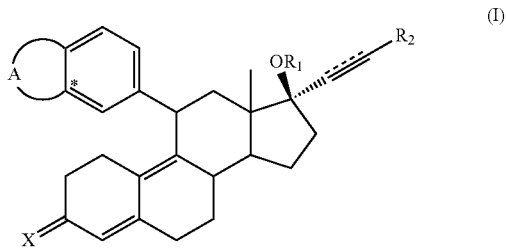

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH;

and the interrupted line represents an optional bond. The invention provides a method wherein the GCR antagonist is ORG34517.

The invention provides a method for treatment of withdrawal from narcotics and subsequent prevention of relapse of narcotic use in a patient in need of such treatment, said method comprising: (a) selecting a patient in need of treatment of withdrawal from narcotics and subsequent prevention of relapse of narcotic use; (b) providing an ingestible drug delivery device comprising: a sensor for sensing at least one biologic condition within a patient and providing a first signal representative thereof; a bioactive substance module comprising a container for holding a volume and/or quantity of bioactive substance therein and a microactuator for dispensing said bioactive substance from said container to a location outside of said capsule body, wherein said bioactive substance is a composition comprising: i) a first therapeutic agent which is a GCR antagonist, or pharmaceutically acceptable salts thereof; ii) optionally separated from the first therapeutic agent, at least one or possibly more additional therapeutic agent(s) selected from the group consisting of opioid analgesics and combinations thereof; and iii) at least one pharmaceutically acceptable carrier, wherein the first and second therapeutic agents are each present in an amount which, in combination, is a therapeutically effective amount for treatment of withdrawal from narcotics and subsequent prevention of relapse of narcotic use in a patient in need of such treatment; and an electronics module, coupled to said sensor and said bioactive substance module, said electronics module comprising a processor, a transponder and a memory, said memory comprising capsule data that comprises data selected from the group consisting of: data related to the patient who ingested said ingestible drug medical device; data related to said bioactive substance; data related to a healthcare provider that enabled said processor; data related to said sensor; data related to the provenance of said ingested drug medical device; and combinations thereof; a power source coupled to said sensor, said bioactive substance module and said electronics module; (c) administering to said patient at least one ingestible delivery device, wherein upon ingesting said ingestible drug delivery device, listening, by said processor, for at least one wireless signal from any other ingested drug delivery device and if no said at least one wireless signal is received within a predetermined period, said processor declaring itself a master drug delivery device and moving to step (c), and if said at least one wireless signal is received within said predetermined period, said processor wirelessly transmits an identification signal and halts any dispense process and continues to listen for another wireless signal; and (d) analyzing said first signal with said capsule data for controlling said microactuator for dispensing said bioactive substance wherein said step of analyzing comprises: (i) receiving a unique identity for the ingestible drug delivery device, wherein the ingestible drug delivery device comprises the unique identity that is associated with at least one of the manufacturer and the medication; (ii) receiving information from the patient interface device in communication with the ingestible drug delivery device and the patient, wherein at the time the patient takes the ingestible drug delivery device, the patient interface device is operative to detect the unique identity associated with the ingestible drug delivery device and confirm delivery of the medication to the patient, that optionally enables the release of at least one bioactive substance to a patient; (iii) receiving information related to the patient who is permitted to ingest said ingestible drug delivery device comprises the identification of the patient, that optionally enables the release of at least one bioactive substance to a patient; (iv) receiving information from data related to a healthcare provider that enables the release of at least one bioactive substance to a patient; (v) receiving the detected unique identity associated with the ingestible drug delivery device detected via a patient interface device and the confirmation of delivery of the medication to the patient via the ingestible drug delivery device, that optionally enables the release of at least one bioactive substance to a patient; and (e) confirming the origin, type and dosage of said at least one bioactive substance based at least on the unique identity of the ingestible drug delivery device; (f) dispensing said at least one bioactive substance to the patient if said origin, type and dosage were confirmed in step (e) and disabling the dispensing of said at least one bioactive substance to the patient from said ingestible drug delivery device if said origin, type and dosage of said at least one bioactive substance was not confirmed in step (e). The invention provides a method wherein the second therapeutic agent is selected from the group consisting of at least one narcotic selected from the group consisting of opioid analgesics, morphine, codeine, buprenorphine, tramadol, fentany, hydromonorphone, morphine, oxycodone/naloxone, opiate, opium, acetyldihydrocodeine, alfentani, allylprodine, alphamethylfentanyl, alphaprodine, benzylmorphine, betaprodine, bezitriamide, buprenorphine, butorphanol, bremazocine, carfentan (carfentanyl), contin, dextromoramide, dextropropoxyphene, dezocine, diacetylmorphine, diamorphine, dihydrocodeine, dihydromorphine, dihydromorphone, diphenoxylate, dipipanone, enadoline, ethylketazocine, ethylmorphine, etonitazene, etorphine, fentanyl, heroin, hydrocodone, hydromorphin (hydromorphine), hydromorphone, ketazocine, ketobemidone, lefetamine, levomethadon, levomethadyl, levomethorphan, levorphanol, loperamide, meperidine, meptazinol, methadone, methadyl, methylmorphine, morphin (morphine), nalbuphine, narcotic, nicocodeine, nicomorphine, normorphine, noscapin, ohmefentanyl, oripavine, oxycodone, oxycontin, oxymorphone, papaveretum, papaverin, pentazocine, percocet, peronine, pethidine, phenazocine, phencyclidine, pholcodine, piritramid (priitramidine), prodine, promedol, propoxyphene, remifentanil, sufentanil, tapentadol, thebaine, tilidine, tramadol, ultracet, and combinations thereof. The invention provides a method wherein the GCR antagonist is selected from the group consisting of ORG 34517, 11-(substituted phenyl)-estra-4,9-diene derivatives, and 11-(substituted phenyl)-estra-4,9-diene derivatives of formula I

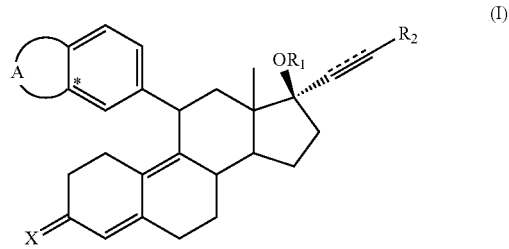

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond. The invention provides a method wherein the GCR antagonist is ORG34517. The invention provides a method further comprising the step of said master drug delivery device transmitting a wireless signal, following transmission of said at least one wireless signal, at a predetermined interval and then listening for any response signal from any other ingested drug delivery device. The invention provides a method further comprising the step of said processor of said master drug delivery device determining whether the large intestine has been entered or whether eight hours has elapsed since ingestion. The invention provides a method further comprising the step of said processor of said master drug delivery device storing the identification and receipt time of any identification signal received by said processor. The invention provides a method further comprising the step of said processor of said master drug delivery device organizing the identifications of a plurality of ingested drug delivery devices based upon said respective receipt times of respective identification signals to form drug delivery device data. The invention provides a method further comprising the step of said processor of said master drug delivery device communicating with the ingested drug delivery device whose receipt time was closest to the ingestion of said master drug delivery device. The invention provides a method further comprising the step of said processor of said master drug delivery device reaching either the large intestine or whether said eight hours has elapsed, whichever occurs first, and conferring to said ingested drug delivery device, whose receipt time was closest to the ingestion of said master drug delivery device, a title of new master drug delivery device along with said drug delivery device data, said original master drug delivery device shutting down permanently. The invention provides a method further comprising the step of said new master drug delivery device analyzing said first signal with said capsule data for controlling said microactuator for dispensing said bioactive substance. The invention provides a method wherein said data related to the patient who is permitted to ingest said ingestible drug delivery device comprises the identification of the patient. The invention provides a method wherein said data related to the patient who is permitted to ingest said ingestible drug delivery device comprises the medical conditions of the patient. The invention provides a method wherein the healthcare provider is selected from the group consisting of a doctor, a physician's assistant, nurse, pharmacist, physical therapist, and dentist. The invention provides a method wherein said data related to said healthcare provider that enabled said processor of said ingested drug delivery device comprises a digital signature of said healthcare provider. The invention provides a method further comprising the step of preventing the dispensing of said bioactive substance if said processor determines that whoever ingested said ingestible drug delivery device is not the patient that is permitted to ingest said ingestible drug delivery device. The invention provides a method wherein said volume of bioactive substance comprises an active pharmaceutical ingredient (API) and further comprising step of deactivating said API if said ingestible drug delivery device is tampered with. The invention provides a method wherein said sensor is capable of detecting the concentration of bioactive substance in the patient, and can prevent release of additional bioactive substance when contraindicated.

The invention provides a method wherein said sensor is capable of detecting pregnancy, and prevents release of bioactive substance when the patient is determined to be pregnant. The invention provides a method wherein said sensor is selected from the group consisting of electronic, biological, chemical, digital sensors, and combinations thereof. The invention provides a method wherein said sensor is selected from the group consisting of a pH sensor, a temperature sensor, a glucose sensor, a pregnancy sensor, a drug sensor, a temperature sensor, a phenylalanine sensor, and combinations thereof. The invention provides a method wherein said sensor comprises a drug sensor for analytes selected from the group consisting of alcohol, nicotine, caffeine, cocaine (including crack cocaine), *cannabis*, amphetamines (including crystal methamphetamine), opiates and opiate analogues (including heroine, oxycodone, hydrocodone, hydromorphone, methadone), dextromethorphan, benzodiazepines, ecstasy (MDMA), GHB, barbiturates, khat, kratom, PCP, LSD, ketamine, peyote, mescaline, psilocybin, rohypnol, *Salvia divinorum*, antidepressants, anti-anxiety medications, sleep aids, allergy medications, and combinations thereof, and prevents release of additional bioactive substance when contraindicated. The invention provides a method further comprising the step of preventing the dispensing of said bioactive substance if said processor determines that the patient that ingested a compound selected from the group consisting of alcohol, nicotine, caffeine, cocaine (including crack cocaine), *cannabis*, amphetamines (including crystal methamphetamine), opiates and opiate analogues (including heroine, oxycodone, hydrocodone, hydromorphone, methadone), dextromethorphan, benzodiazepines, ecstasy (MDMA), GHB, barbiturates, khat, kratom, PCP, LSD, ketamine, peyote, mescaline, psilocybin, rohypnol, *Salvia divinorum*, antidepressants, anti-anxiety medications, sleep aids, allergy medications, and combinations thereof wherein said sensor is capable of detecting the concentration of bioactive substance in the patient, and prevents release of additional bioactive substance when contraindicated. The invention provides a method wherein the ingestible drug delivery device further comprises a deactivation module comprising a container for holding a volume and/or quantity of a deactivator and a microactuator for dispensing said deactivator to said bioactive substance module, wherein the deactivator module is coupled to said bioactive substance module, and wherein the electronics module is coupled to said deactivator module, said electronics module comprising a processor, a transponder and a memory.

The invention provides a kit for comprising: (a) at least one ingestible drug delivery device of the invention comprising a at least one pharmaceutical composition in a therapeutically effective amount; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition. The invention provides a product of manufacture comprising at least one ingestible drug delivery device of the invention comprising at least one pharmaceutical composition in a therapeutically effective amount in a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist, and instructions for use.

The compositions and/or devices of the invention can be used for prevention and/or treatment of conditions and/or indications as set forth herein.

BRIEF DESCRIPTION OF SEVERAL VIEWS OF THE DRAWINGS

The invention will be described in conjunction with the following drawings in which like reference numerals designate like elements and wherein:

FIG. 2A is an unraveled version of a Smart Pill of the present invention showing the Smart Pill components positioned on a substrate having an antenna embedded therein;

FIG. 2B is a Smart Pill in its ready to use form;

DETAILED DESCRIPTION OF PREFERRED EMBODIMENTS OF THE INVENTION

Figure 1:
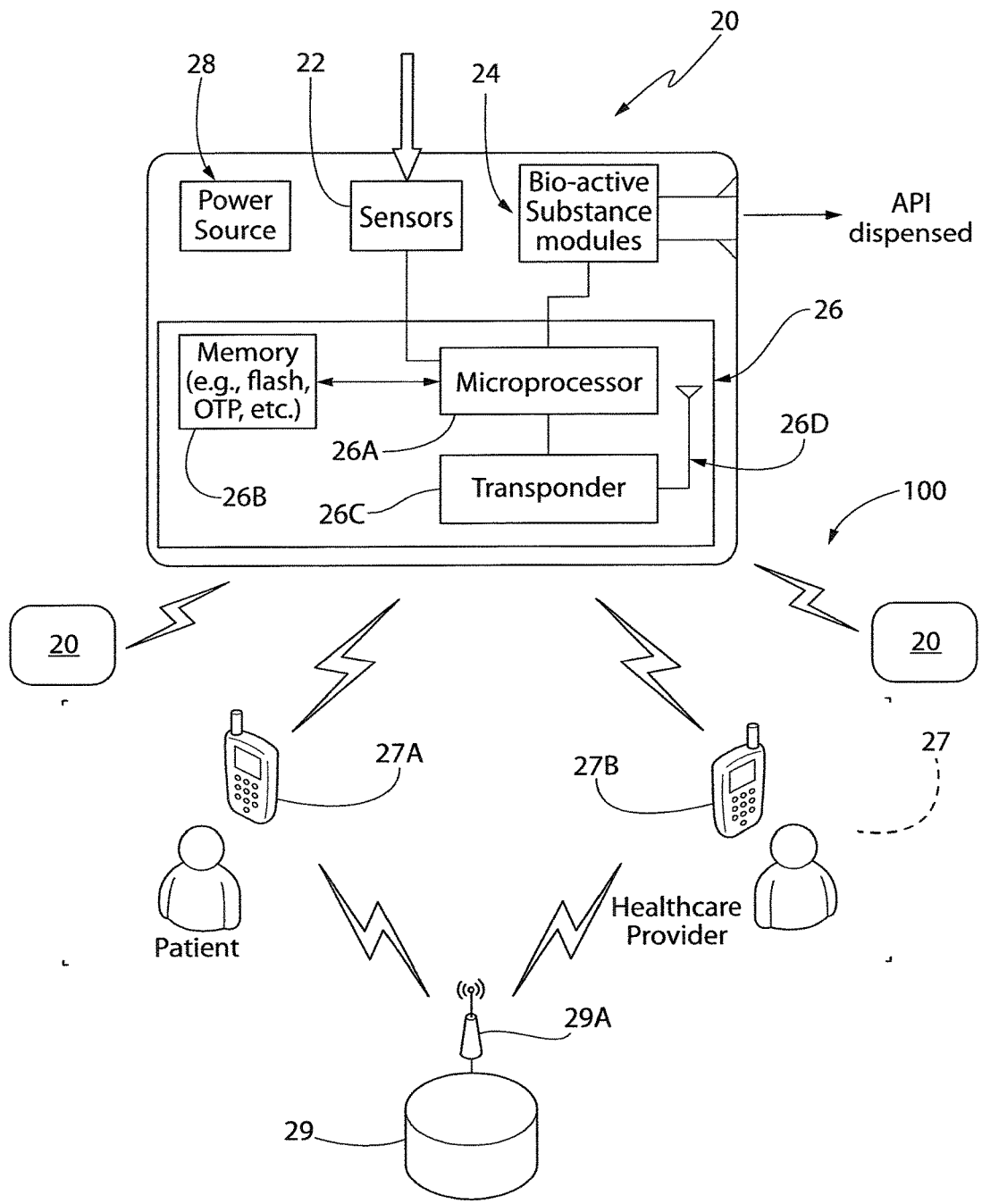
FIG. 1 is a block diagram of an exemplary Smart Pill and wireless encrypted network of the present invention.

An amount is "effective" as used herein, when the amount provides an effect in the subject. As used herein, the term "effective amount" means an amount of a compound or composition sufficient to significantly induce a positive benefit, including independently or in combinations the benefits disclosed herein, but low enough to avoid serious side effects, i.e., to provide a reasonable benefit to risk ratio, within the scope of sound judgment of the skilled artisan. For those skilled in the art, the effective amount, as well as dosage and frequency of administration, may easily be determined according to their knowledge and standard methodology of merely routine experimentation based on the present disclosure.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant. The subject can include, but is not limited to, human, equine, bovine, ovine, swine, rodent, canine, feline, avian, amphibian, or reptile.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a disease or condition, or a combination of therapies (e.g., a combination of prophylactic or therapeutic agents).

As used herein, the terms "therapies" and "therapy" can refer to any method(s), composition(s), and/or agent(s) that can be used in the prevention, treatment and/or management of a disease or condition, or one or more symptoms thereof.

As used herein, the terms "treat," "treatment," and "treating" in the context of the administration of a therapy to a subject refer to the reduction or inhibition of the progression and/or duration of a disease or condition, the reduction or amelioration of the severity of a disease or condition, and/or the amelioration of one or more symptoms thereof resulting from the administration of one or more therapies.

The healthcare provider may be any of the healthcare providers described herein, including a doctor, physician's assistant, nurse, pharmacist, physical therapist, dentist, weight management specialist, and the like. The healthcare professional may also be a more general service provider such as a personal trainer, yoga instructor, or the like. In another embodiment, the healthcare professional may be an institution or organization, such as a hospital, university, health maintenance organization, dentist office and the like.

Ingestible Drug Delivery Device

The invention is directed to an ingestible drug delivery device which may communicate with other ingestible drug delivery devices and/or other electronic devices to, for example, control release of bioactive substances. FIG. 1 depicts an exemplary diagram of the ingestible drug delivery device. The ingestible drug delivery device of the invention may comprise, for example, at least one electronics module operably connected to sensor, a bioactive substances module, a deactivation module and a power source. The electronics module may be configured to receive at least one signal from one or more sensors, including information regarding one or more physiological conditions of a vertebrate subject. The electronics module can be programmable and can include memory, and a transponder. The at least one electronics module can be configured to implement logic such as comparison, sorting, reduction, and/or endpoint determination. The electronics module can be configured to collect and analyze multiple data points in a relative fashion, including either serially or in parallel. The electronics module can be configured to receive information from at least one of a sensor, a timekeeping device, a user interface, and an outside operating source. The electronics module can process the information from the one or more sensors into at least one resulting instruction and providing the at least one resulting instruction to, for example, the bio-active substance module and/or the deactivation module. The electronics module can transmit information and/or instructions using, for example, a transponder.

The electronics module may comprise a programmable microprocessor which can be directed through a number of sources including, but not limited to, pre-programmed information in the programmable microprocessor regarding one or more physiological conditions of the subject; information provided by user input regarding one or more physiological conditions of the subject; activation/deactivation by, for example, a healthcare provider; or programming provided by the electronics module regarding one or more physiological conditions of the subject.

Another key aspect of the ingestible drug delivery device is that the provenance, i.e., the origins and subsequent activity(ies) of each drug delivery device is stored within the memory of that device. Thus, the manufacturer, the API content and amount, the communication history, the healthcare provider (e.g., pharmacist) who prepared or otherwise "enabled" the drug device etc., i.e., any activity or individual associated with the drug device is stored in the memory. All of this information can be recalled by appropriate wireless commands to the particular drug device.

Networking

The electronics module can be configured to receive at least one signal from the one or more sensors and to provide instructions in the form of at least one signal to the one or more bioactive substance module and/or deactivation modules. The digital processing units can be configured to receive at least one signal from the one or more sensors and to process the signal into one or more resulting instructions and provide the instructions in the form of at least one signal to the programmable microprocessor. The electronics module can be configured to receive at least one signal from the one or more digital processing units, for example other ingestible drug delivery devices of the invention, and to provide instructions in the form of at least one signal to the one or more bioactive substance module and/or deactivation modules. A signal can include, for example, an optic signal, a light signal, a chromatic signal, an acoustic signal, a vibrational signal, an infrared (IR) signal, an electronic signal, a digital signal, a radio signal, a wireless signal, or any other detectable signal. A signal from the one or more sensors, digital processing unit, or programmable microprocessor can be part of the communication between the one or more sensors, the programmable microprocessor, the digital processing unit, and/or the one or more bioactive substance module and/or deactivation modules. For example, the programmable microprocessor, the digital processing unit, or the one or more sensors can be configured with one or more transmitter and/or one or more receiver and can utilize for communication transmissions such as radiowaves. For example, the one or more sensor may include a means for transmitting radiofrequency signals and may include, e.g., an analyte sensor-enabled RFID tag (see, e.g., in Moore, J. Diabetes Sci. Technol. 3: 180-183, 2009, which is incorporated herein by reference). Miniaturized (0.5.times.0.5.times.5 mm) Implantable sensors are produced by BIORASIS Inc. including the GLUCOWIZARD®, an implantable sensor that senses glucose levels and transmits the information to a proximal communicator. A bio-sensor chip can be used that includes a passive transponder, glucose sensor and integrated circuitry. See, e.g., U.S. Pat. No. 7,125,382 to Zhou entitled "Embedded Bio-sensor System," which is incorporated herein by reference. See, e.g., Digital Angel Corporation, St. Paul, Minn. Transmission communications may include frequency-hopping spread spectrum technology such as BLUETOOTH® wireless technology. The acoustic transmission communication may include frequency-hopping spread spectrum technology such as BLUETOOTH® wireless technology.

Vehicles of communication include a network. In various aspects, the network may comprise local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players, telephones, including mobile telephones and cordless telephones, and computers and computer-related devices and components, such as printers.

Accordingly, in various aspects, the communications interface may comprise one or more interfaces such as, for example, a wireless communications interface, a network interface, a transmit interface, a receive interface, a media interface, a system interface, a component interface, a switching interface, a chip interface, a microprocessor, and so forth. When implemented by a wireless device or within wireless system, for example, the mobile computer may include a wireless interface comprising one or more antennas, transmitters, receivers, transceivers, amplifiers, filters, control logic, and so forth.

In various implementations, the described aspects may communicate over wireless shared media in accordance with a number of wireless protocols. Examples of wireless protocols may include various wireless local area network (WLAN) protocols, including the Institute of Electrical and Electronics Engineers (IEEE) 802.xx series of protocols, such as IEEE 802.11a/b/g/n, IEEE 802.16, IEEE 802.20, and so forth. Other examples of wireless protocols may include various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), ZigBee, and so forth.

In various implementations, the described aspects may comprise part of a cellular communication system. Examples of cellular communication systems may include CDMA cellular radiotelephone communication systems, GSM cellular radiotelephone systems, North American Digital Cellular (NADC) cellular radiotelephone systems, Time Division Multiple Access (TDMA) cellular radiotelephone systems, Extended-TDMA (E-TDMA) cellular radiotelephone systems, Narrowband Advanced Mobile Phone Service (VAMPS) cellular radiotelephone systems, third generation (3G) systems such as WCDMA, CDMA-2000, UMTS cellular radiotelephone systems compliant with the Third-Generation Partnership Project (3GPP), and so forth.

In various aspects, the electronics module includes the functionality to wirelessly receive and/or wirelessly transmit data, e.g., physiologic data, to a computer, such as a mobile computer.

Further, in various aspects, the electronics module may incorporate and/or be associated with, e.g., communicate with, various devices. Such devices may generate, receive, and/or communicate data, e.g., physiologic data. The devices include, for example, "intelligent" devices such as cellular phones, personal data assistants, or devices configured to be used by a health care provider or a patient to receive or transmit data to and from the ingestible drug delivery devices.

The mobile computer may be implemented as a mobile telephone. For example, the mobile computer may be implemented as a short-range, portable electronic device used for mobile voice or data communication over a network of specialized cell site base stations. The mobile telephone is sometimes known as or referred to as "mobile," "wireless," "cellular phone," "cell phone," or "hand phone (HP)."

Figure 9:
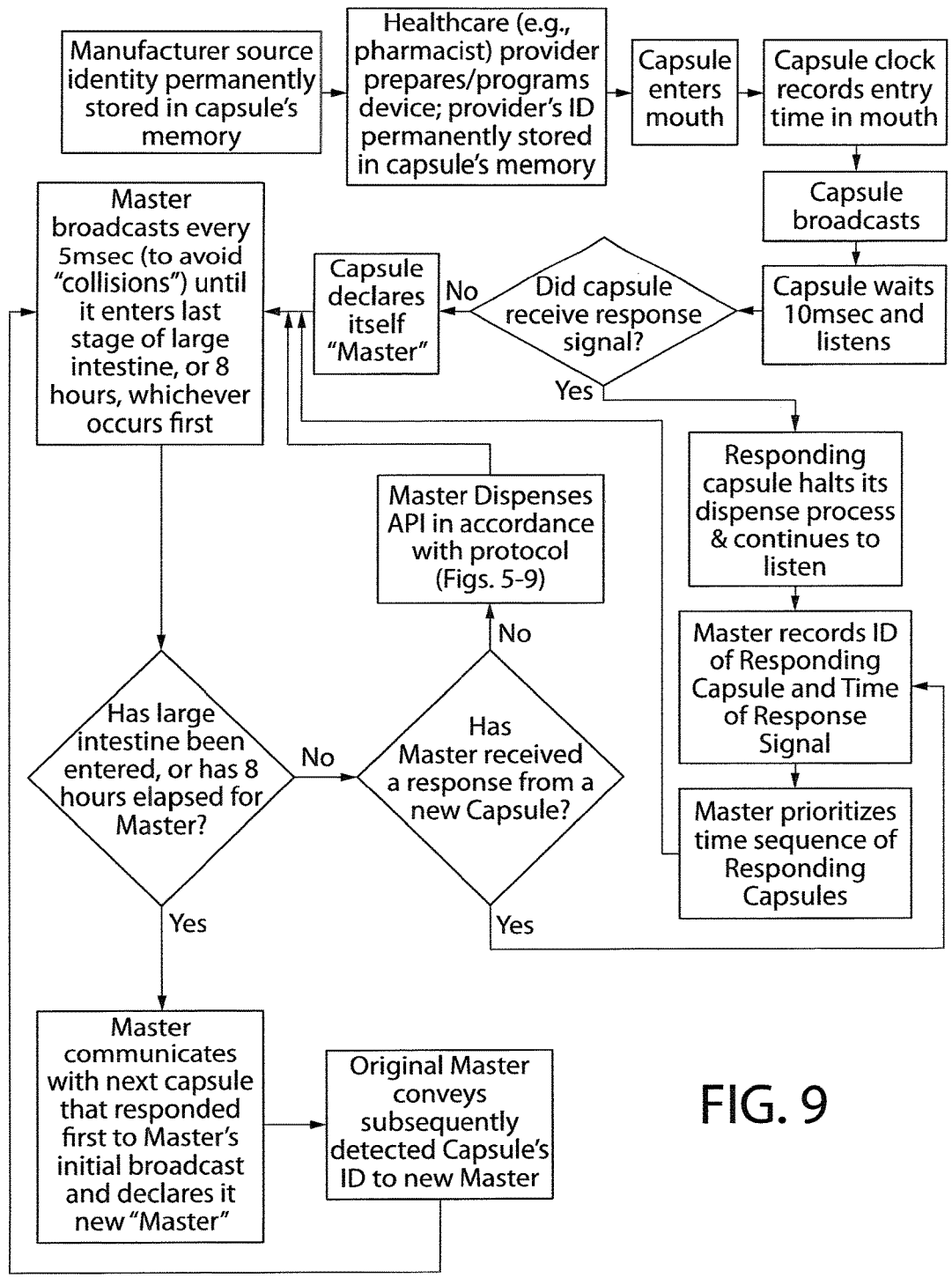
FIG. 9 is a an alternative protocol for avoiding inadvertent and intentional overdosing.

FIG. 9 provides an exemplary wireless communication protocol where more than one Smart Pill is ingested by an individual. This protocol, among other things, prevents inadvertent or intentional overdosing by the individual who ingests them. In general, each ingestible drug delivery device initially "listens" for the broadcast of another ingested drug delivery device. If no signal is received within a predetermined period of time, that ingestible drug delivery device declares itself the "master" and begins to broadcast a signal at periodic intervals. Any subsequently ingested drug delivery devices will receive the broadcast signal and will deactivate their API delivery mechanism while responding with their particular ID number that is stored by the "master" in time sequence. If subsequently ingested drug delivery devices are permitted by the physician, when the master reaches its destination or final dispensement, it communicates to the ingested drug delivery device that entered the individual's body just after the master entered to be the new "master." In addition, the time sequence by ID number is also transmitted from the old master to the new master. If, on the other hand, only the master was permitted to dispense the API, then no new master is declared and all subsequently-ingested drug delivery devices remain inactive for their duration in the individual's body.

Sensors

The ingestible drug delivery device may be configured to receive one or more signals from one or more sensors can be part of the communication between the sensors and the electronics module or the programmable microprocessor. A signal from the programmable microprocessor can be part of the communication between the programmable microprocessor and the one or more bioactive substance module and/or deactivation modules. For example, where the one or more sensors are configured to emit an electromagnetic signal following detection of a physiological condition of the subject, the programmable microprocessor can include an EM signal detection device, such as a detection device configured to detect non-visible light or light of a specific wavelength. See, for example, U.S. Patent Application No. 2003/0143580 to Straus, titled "Rapid and sensitive detection of molecules," which is incorporated herein by reference. In embodiments in which the one or more sensors are configured to emit optically detectable signals, the one or more sensors can include, in part or in whole, an optically permeable section (e.g. a window), and the one or more sensors or the programmable microprocessor can include, in part, a spectrophotometer and/or light source configured to elicit signals related to information regarding a physiological condition of the subject. For example, the one or more sensors can include at least one of a chromogen, fluorescent agent, luminescent agent, a quantum dot, or a compound configured to exhibit alterable optical density. A light source associated with the one or more sensors can include, for example, a light emitting diode or a white light source, such as a source configured to provide light in a variable and/or specific wavelength, including infrared (IR) or ultraviolet (UV). See, for example, U.S. Pat. No. 5,183,740 to Ligler et al., titled "Flow immunosensor method and apparatus," U.S. Pat. No. 7,459,713 to Coates, titled "Integrated handheld sensing system approach for handheld spectral measurements having a disposable sample handling apparatus," U.S. Patent Application No. 2008/0265146 to Coates, titled "Integrated sensing module for handheld spectral measurements," which are herein incorporated by reference. For example, a sensor pair consisting of light emitter and light detector can be configured to be a part of the one or more sensors. The electronics module sensor can include a digital signal processor and/or software for converting the light signal into information able to be stored or communicated between the digital processing unit, programmable microprocessor, and sensors. See, for example: U.S. Pat. No. 6,623,698 to Kuo, titled "Saliva-monitoring biosensor head toothbrush;" U.S. Pat. No. 7,314,453 to Kuo, titled "Handheld diagnostic device with renewable biosensor;" U.S. Patent Application No. 2003/0023189 to Kuo, titled "Handheld diagnostic device with renewable biosensor;" and U.S. Patent Application No. 2002/0127143 to Kuo, titled "Saliva-monitoring biosensor electrical toothbrush," which are herein incorporated by reference. In some embodiments, the one or more sensors can use electric pulses to measure the conductivity of one or more tissues of the subject to measure a physiological condition of the subject, e.g., pH, pCO.sub.2, blood flow, blood pressure, skin temperature, core temperature, tissue temperature, or blood oxygenation. See, for example, U.S. Pat. Nos. 6,623,698 and 7,314,453 to Kuo.

The device including one or more bioactive substance module and/or deactivation modules configured to be administered to a subject, and a programmable microprocessor configured to provide instructions to the one or more bioactive substance module and/or deactivation modules in response to information regarding one or more physiological conditions of the vertebrate subject can further include one or more sensors operably connected to the programmable microprocessor and configured to sense one or more indicator of the one or more physiological conditions. The one or more sensors can be operably connected to the electronics module. The electronics module can be operably connected to the programmable microprocessor and can be configured to receive information from the sensor, to process the information into at least one resulting instruction, and to provide the at least one resulting instruction to the programmable microprocessor. The programmable microprocessor is configured to provide instructions to the one or more bioactive substance module and/or deactivation modules in response to information from the one or more sensors regarding one or more physiological conditions of the patient. The one or more indicator of the one or more physiological conditions can include a plasma and/or localized tissue level of one or more analytes, e.g. a metabolic analyte, in the subject. In an aspect, the one or more analytes can include analytes associated with a disorder. In an aspect, the one or more metabolic analytes can include metabolic analytes associated with a metabolic disorder. The one or more metabolic analytes indicative of a metabolic disorder include, but are not limited to, glucose, free fatty acids, triglycerides, insulin, glucagon, pro-inflammatory molecules, cholesterol, low density lipoprotein (LDL), and high-density lipoprotein (HDL).

The one or more sensors are configured to provide data to the electronics module and/or the programmable microprocessor regarding the plasma and/or tissue levels of analytes associated with a disorder. The programmable microprocessor is configured to respond to the data received from the sensors by adjusting the one or more bioactive substance module and/or deactivation modules to appropriately release or not release the bioactive substance in order to treat a disorder. Alternatively or in addition, the electronics module is configured to process the data from the sensor and provide instructions and/or programming to the programmable microprocessor to adjust the one or more bioactive substance module and/or deactivation modules to appropriately release the deactivation substance to, for example, deactivate the bioactive substance.

The one or more sensors may be configured to provide data to the electronics module and/or the programmable microprocessor regarding the plasma, blood, and/or tissue levels of bioactive substance. The programmable microprocessor may be configured to respond to the data received from the sensors by adjusting the one or more bioactive substance module and/or deactivation modules to appropriately release and/or not release the bioactive substance and/or deactivation substance in order to titrate, for example, blood and/or or plasma concentration, to for example, treat a condition or prevent overdose. Alternatively or in addition, the electronics module is configured to process the data from the sensor and provide instructions and/or programming to the programmable microprocessor to adjust the one or more bioactive substance module and/or deactivation modules to appropriately release the deactivation substance to, for example, deactivate the bioactive substance.

In an aspect, the one or more analytes can include, but are not limited to, utilizable glucose, produced and/or released glycerol, free fatty acids, cAMP (indicative of beta-adrenergic receptor stimulation), hexokinase and phosphofructokinase or their enzymatic activities or products.

The device can include one or more sensors configured to sense one or more other physiological conditions of the subject including, but not limited to, pH, pCO2, blood flow, blood pressure, skin temperature, core temperature, tissue temperature, or blood oxygenation. The one or more sensors can also be configured to sense measures of physical activity of the subject as a means for estimating daily energy expenditure. Measures of physical activity of a subject include, but are not limited to, body temperature, heart rate, skin resistance, motion/acceleration, and velocity.

The one or more sensors operably connected with the electronics module and/or programmable microprocessor can include, but are not limited to, one or more biosensors, chemical sensors, pressure sensors, temperature sensors, flow sensors, viscosity sensors, shear sensors (e.g., for measuring the effective shear modulus of the fluid at a frequency or strain-rate), pH sensors, optical sensors (e.g., charged couple device (CCD) array), optical waveguide sensors, acoustic sensors, surface acoustic wave sensors, quartz microbalance sensors, metal oxide sensors, bulk acoustic wave sensors, plate acoustic wave sensors, electrical sensors, magnetic sensors, interdigitated microelectrode sensors, electrochemical sensors, electrically conducting sensors, artificial noses, electronic noses, electronic tongues, semiconductive gas sensors, mass spectrometers, near infrared and infrared spectrometers, ultraviolet sensors, visible light-based sensors, fluorescence spectrophotometers, conductive-polymers, gas-fluorescence spectrophotometers, impedance spectrometers, aptamer-based biosensors, ion mobility spectrometry, photo-ionization detectors, amplifying fluorescent polymer sensors, ion mobility spectrometry, electrical impedance, microgravimetric sensors, cantilever and microcantilever sensors, accelerometers, global positioning devices, clocks or time-keeping devices. See, e.g., U.S. Pat. Nos. 5,522,394; 5,873,835; 6,409,674; 6,111,520; 6,278,379; 6,475,639; 6,802,811; 6,855,115; 6,517,482; 6,675,030; 6,836,678; 6,954,662; 7,184,810; 7,299,080, and U.S. Patent Application 2005/0277839, each of which is incorporated herein by reference.

The one or more sensors can include a single sensor or an array of sensors, and is not limited to a particular number or type of sensors. The one or more sensors can be very small, comprising a sensor or array of sensors, having, for example, a biosensor, a chemical sensor (Snow Science, 2005, 307: 1942-1945), a gas sensor (Hagleitner et al., Nature, 2001 414:293-296), an electronic nose, a nuclear magnetic resonance imager (Yusa et al., Nature, 2005, 343:1001-1005). The foregoing references are each incorporated herein by reference. Further examples of sensors are provided in The Biomedical Engineering Handbook, Second Edition, Volume I, J. D. Bronzino, Ed., Copyright 2000, CRC Press LLC, pp. V-1-51-9; Morrison et al., "Clinical Applications of Micro- and Nanoscale Biosensors" in Biomedical Nanostructures. Edited by K. E. Gonsalves, C. L. Laurencin, C. R. Halberstadt, L. S, Nair. 2008, John Wiley & Sons, Inc.; and U.S. Pat. No. 6,802,811, each of which is incorporated herein by reference.

The one or more sensors can be configured to detect an analyte that includes, but is not limited to, a biological marker, an antibody, an antigen, a peptide, a polypeptide, a neuropeptide, a protein, a complex, an enzyme, a hormone, a neurotransmitter, a nucleic acid, a cell (and, in some cases, a cell of a particular type, e.g. by methods used in flow cytometry), a cell fragment, a cellular component, a platelet, an organelle, a gamete, a pathogen, a lipid, a lipoprotein, an alcohol, an acid, an ion, an immunomodulator, a sterol, a carbohydrate, a saccharide, a polysaccharide, a glycoprotein, a metal, an electrolyte, a metabolite, an organic compound, an organophosphate, a drug, a therapeutic, a gas, a pollutant, or a tag. The one or more sensors can include one or more binding elements configured to interact with an analyte including, but not limited to, binding molecules, recognition elements, antibodies or fragments thereof, oligonucleotide or peptide based aptamers (see, e.g., Mok & Li Sensors 8: 7050-7084, 2008, which is incorporated herein by reference), receptors or ligands, artificial binding substrates (e.g. those formed by molecular imprinting), or any other examples of molecules and/or substrates capable of interacting with an analyte.

In an aspect, the device including the one or more sensors can include one or more optical sensors. An optical sensor can be configured to measure the optical absorption, optical emission, fluorescence, or phosphorescence, luminescence of an analyte or an associated tag or binding element, other tissues of interest, or combinations thereof. Such optical properties can be inherent optical properties of the analyte, e.g. autofluorescence, or can be optical properties of materials added or introduced into the body of the subject that interact with the analyte, other tissues of interest, or combinations thereof. Optical sensing of materials in blood, for example, is described in Manley et al., "Blood characterization using UV/VIS spectroscopy" Proc. SPIE Advances in Fluorescence Sensing Technology II, Joseph R. Lakowicz; Ed. Vol. 2388, p. 462-470, 1995 and U.S. Pat. Nos. 5,589,932 and 7,027,134, each of which is incorporated herein by reference.

The ingestible drug delivery devices may include one or more sensors configured to sense the blood glucose levels in the subject. The one or more sensors can include a glucose sensor that is either an integral part of the device, wherein the sensors is operably connected to the programmable microprocessor as described herein, or is in a separate device, for example a glucose sensing device in wireless communication with the programmable microprocessor in the device described herein. A number of different glucose monitors have been described using, for example, pin prick, transdermal, or implantable devices. See, e.g., U.S. Pat. Nos. 4,436,094; 4,953,552; 5,497,772; U.S. Patent Applications 2010/0049021; 2010/0081910; each of which is incorporated herein by reference. The one or more sensors can include one or more electrochemical- or photochemical-based sensors wherein a measurable chemical reaction occurs in response to the presence of one or more analyte. For example, many electrochemical sensors use enzymes as specifiers for the analyte. The enzymes cause a chemical reaction, such as a reduction reaction, and electrons released by the reaction are transferred to a mediator molecule, which itself is converted. The mediator then transfers the electrons to an electrode for electrochemical measurement or transfers the electrons to an indicator molecule for photochemical responses. Ferrocene derivatives and hexacyanoferrate are examples of one-electron mediators. Quinones are an example of two-electron mediators. A glucose sensor included in the device uses as the specifier an oxidoreductase that oxidizes glucose to gluconolactone. Electrons from the glucose are then transferred to the oxidized form of a mediator molecule, which in turn delivers the electrons to an electrode. The amount of electric current generated is proportional to the amount of glucose in the sample, and electronics within the sensor convert the signal, and the signal is communicated to the programmable microprocessor or the electronics module that is operably connected to the programmable microprocessor. See, e.g., Hones, et al., Diabetes Techn & Therap, 10: Supplement 1 S10-S26, 2008. Examples of commercially available glucose monitors using such technology in measuring blood glucose levels of a subject include, but are not limited to, OneTouch® blood glucose monitors (LifeScan-Johnson & Johnson, Milpitas, Calif.), Accu-Chek® blood glucose monitors (F. Hoffman-Roche A G, Basel, Switzerland), and Ascencia® blood glucose monitors (Bayer HealthCare LLC, Tarrytown, N.Y.).

In an aspect, the glucose sensor for measuring blood glucose levels of a subject can include a continuous monitoring system, examples of which include, but are not limited to Freestyle. Navigator® glucose monitor (Abbot Diabetes Care, Alameda, Calif.), Guardian® Real-Time glucose monitor (Medtronic MiniMed, Northridge, Calif.), and Dex-Com® SEVEN® glucose monitor (DexCom, San Diego, Calif.). See, e.g., Hermanides & DeVries, Diabetologia, 53: 593-596, 2010, which is incorporated herein by reference. The FreeStyle Navigator® glucose monitor, for example, is biocompatible chip implanted into the abdomen or back of the upper arm of a subject and includes an external receiver. Similarly, blood glucose sensor-enabled radio frequency identification (RFID) devices have been described for active monitoring of glucose. See, e.g., Moore, J. Diabetes Sci. Technol. 3: 180-183, 2009, which is incorporated herein by reference. Miniaturized (0.5.times.0.5.times.5 mm) implantable glucose sensors can include the GLUCOWIZZARD® implantable glucose sensor that senses glucose levels and transmits the information to a proximal communicator. See, e.g., BIORASIS Storrs/Mansfield, Conn. A bio-sensor chip can include a passive transponder, glucose sensor, and integrated circuitry. See, e.g., U.S. Pat. No. 7,125,382 to Zhou entitled "Embedded Bio-sensor System," which is incorporated herein by reference. See, e.g., Digital Angel Corporation, St. Paul, Minn. Other methods for continuous monitoring of blood glucose levels of a subject include transcutaneous fluorescence lifetime-based microsensors or subcutaneous microelectromechanical systems (MEMS)-based sensors. See, e.g., U.S. Pat. No. 6,304,766; Nielsen, et al., J. Diabetes Sci. Technol. 3: 98-109; Li, et al., J. Diabetes Sci. Technol. 2: 1066-1074, 2008, each of which is incorporated herein by reference.

In an aspect, the one or more sensors can use a charged coupled device (CCD) or complementary metal-oxide-semiconductor (CMOS) sensor, for example, in combination with a binding element that exhibits altered optical properties, e.g., fluorescence, in response to binding an analyte. For example, glycerol and/or free fatty acids can be analyzed using one or more of the sensors. A sensor for measuring a free fatty acid can include an acyl-CoA-binding protein which exhibits an increased fluorescence yield in response to binding a fatty acid. See, e.g., Wadum, et al., Biochem. J., 365: 165-172, 2002, which is incorporated herein by reference.

In an aspect, the one or more sensor can include a binding element, e.g., an antibody or oligonucleotide aptamer, configured to exhibit Forster or fluorescence resonance energy transfer (FRET) in response to binding one or more analytes in the subject. FRET is a distance-dependent interaction between the excited states of two fluorophore molecules in which excitation is transferred from a donor molecule to an acceptor molecule without emission of a photon. For use in a sensor, one or more binding molecules, e.g., antibodies or oligonucleotide aptamers, associated with the one or more sensors are configured with at least one donor molecule and at least one acceptor molecule. The interaction of an analyte with the binding molecule of the sensor results in a conformation change in the binding molecule, leading to changes in the distance between the donor and acceptor molecules and changes in measurable fluorescence.

Donor and acceptor fluorophore pairs can be considered for FRET including, but not limited to, fluorescein and tetramethylrhodamine; IAEDANS and fluorescein; fluorescein and fluorescein; and BODIPY FL and BODIPY FL, and various Alexa Fluor pairings as described herein. The cyanine dyes Cy3, Cy5, Cy5.5 and Cy7, which emit in the red and far red wavelength range (>550 nm) as well as semiconductor quantum dots can also be used for FRET-based detection systems. Quenching dyes can also be used to quench the fluorescence of visible light-excited fluorophores, examples of which include DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs can be considered for FRET associated with the binding molecule including, but not limited to, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

The one or more sensors for sensing one or more physiological conditions of a subject can include surface plasmon resonance (for planar surfaces) or localized surface plasmon resonance (for nanoparticles). Surface plasmon resonance involves detecting changes in the refractive index on a sensor surface in response to changes in molecules bound to the sensor surface. In an aspect, the surface of the sensor is a solid support coated with a thin film of metal, e.g., gold. The one or more sensors include a matrix to which is immobilized one or more binding molecules, e.g., antibodies or aptamers, that recognize one or more analytes. The sensor is illuminated by monochromatic light. Resonance occurs at a specific angle of incident light. The resonance angle depends on the refractive index in the vicinity of the surface, which is dependent upon the concentration of analyte bound to the surface. See, e.g., Raghavan & Bjorkman Structure 3: 331-333, 1995, which is incorporated herein by reference.

The one or more sensors for sensing analytes can be one or more label-free optical biosensors that incorporate other optical methodologies, e.g., interferometers, waveguides, fiber gratings, ring resonators, and photonic crystals. See, e.g., Fan, et al., Anal. Chim. Acta 620: 8-26, 2008, which is incorporated herein by reference. The light-based signal or electrical signal to the sensor is converted by a transducer, e.g., within the digital processing unit, into within the digital processing unit, which then processes the data into information that can be stored, analyzed, and communicated, including, for example, at least one resulting instruction. The electronics module provides the at least one resulting instruction to the programmable microprocessor.

The one or more sensors configured to provide information regarding one or more physiological conditions of the subject can include one or more microcantilevers. A microcantilever can act as a biological sensor by detecting changes in cantilever bending or vibrational frequency in response to binding of one or more analytes to the surface of the sensor. See, e.g., Lavrik et al., Rev. Sci. Inst, 75:4: 2229-2253, 2004, which is incorporated herein by reference. In an aspect, the sensor can include a microcantilever or a microbead as in an immunoaffinity binding array. In another aspect, a biochip can be formed that uses microcantilever bi-material, e.g., formed from gold and silicon, as sensing elements. See, e.g. Vashist J. Nanotech Online 3: DO: 10.2240/azojono0115, 2007, which is incorporated herein by reference. The gold component of the microcantilever can be coated with one or more binding molecules which upon binding one or more analytes causes the microcantilever to deflect. Aptamers or antibodies specific for one or more analytes can be used to coat microcantilevers. See, e.g., U.S. Pat. No. 7,097,662, which is incorporated herein by reference. The one or more sensors can incorporate one or more methods for microcantilever deflection detection including, but not limited to, piezoresistive deflection, optical deflection, capacitive deflection, interferometry deflection, optical diffraction grating deflection, and charge coupled device. The deflection is measured and transmitted as data by a transducer, e.g., within the digital processing unit, which then processes the data into information that can be stored, analyzed, and communicated, including, for example, at least one resulting instruction. The electronics module provides the at least one resulting instruction to the programmable microprocessor. In some aspects, the one or more microcantilevers can be a nanocantilever with nanoscale components. The one or more microcantilevers and/or nanocantilevers can be arranged into arrays. Both microcantilevers and nanocantilevers can find utility in microelectomechnical systems (MEMS) and/or nanoelectomechnical systems (NEMS).

The one or more sensors for sensing analytes can include a field effect transistor (FET) based biosensor. In this aspect, interaction of one or more analytes with one or more binding elements of the sensor induces an electrical change that is detected by the transistor. See, e.g., U.S. Pat. No. 7,303,875, which is incorporated herein by reference. The signal is processed by the electronics module into at least one resulting instruction. The electronics module provides the at least one resulting instruction to the programmable microprocessor.

The one or more sensors for sensing one or more analytes can incorporate electrochemical impedance spectroscopy. Electrochemical impedance spectroscopy can be used to measure impedance across a natural and/or artificial lipid bilayer. The sensor can incorporate an artificial bilayer that is tethered to the surface of a solid electrode. One or more receptor can be embedded into the lipid bilayer. The one or more receptors can be ion channels that open and close in response to binding of a specific analyte. The open and closed states can be quantitatively measured as changes in impedance across the lipid bilayer. The changes in impedance measured and transmitted as data by a transducer. See, e.g., Yang, et al., IEEE SENSORS 2006, EXCO, Daegu, Korea/Oct. 22-25, 2006, which is incorporated herein by reference. The signal is processed by the electronics module into at least one resulting instruction. The electronics module provides the at least one resulting instruction to the programmable microprocessor.

The one or more sensors can include cells with binding molecules that induce a measurable or detectable change in the cells, e.g., a luminescent signal, when bound to analytes. For example, one can use a bioluminescent bioreporter integrated circuit in which binding of an analyte to an engineered cell induces expression of a reporter polypeptide linked to a luminescent response. See, e.g., U.S. Pat. No. 6,673,596; Durick & Negulescu Biosens. Bioelectron. 16: 587-592, 2001, each of which is incorporated herein by reference. Alternatively, the one or more cell can be engineered to emit an electrical signal in response to interacting with one or more analytes. In a further aspect, an implantable biosensor can include genetically modified cells that respond to binding analytes by emitting a measurable electrical signal in response to one or more intracellular second messenger molecules that in turn modulate the activity of one or more ion channels in the genetically modified cells. The genetically modified cells act as an implantable biosensor that can be coupled via an electrical or optical interface to electronics module that processes the signal into at least one resulting instruction and provides the at least one resulting instruction to a programmable microprocessor. See U.S. Patent Application 2006/0234369 A1; which is incorporated herein by reference. In another aspect, a biosensor can include a microbial biosensor. For example, a microbial biosensor and an oxygen electrode can be used to sense free fatty acid. See, e.g., Schmidt, et al., Biosensors Bioelectronics 11: 1139-1145, 1996, which is incorporated herein by reference.

The one or more sensors can be configured to include an assembly for in vivo microdialysis. In vivo microdialysis allows for continuous sampling from the interstitial fluid of a tissue with minimal influence on surrounding tissues and/or whole body function. A microdialysis probe can be inserted into a tissue of interest, and perfused at a constant flow rate with a physiological buffer, e.g., saline. The tip of the probe consists of a semi-permeable membrane through which compounds in the interstitial fluid of the tissue can diffuse and subsequently be sampled from the outlet tubing of the probe.

The one or more sensors can include one or more temperature sensors configured to measure temperature in one or more tissues. The temperature sensor can be a thermistor, a thermocouple, or a resistive temperature detector. In an aspect, the temperature sensor is an integral component of a self-contained, fully ingestible device.

The one or more sensors can include one or more sensors that are calorimeters configured to measure caloric intake and/or energy expenditure. In an aspect, the one or more calorimeter can include an indirect calorimeter configured to assess the physical activity of the subject by periodically monitoring heart rate, body temperature, skin resistance, motion/acceleration sensing, velocity and providing an estimate of caloric intake/energy expenditure. The indirect calorimeter can include one or more of a temperature sensor, a heart rate sensor, an accelerometer, a global positioning system, or a combination thereof. See, e.g., U.S. Patent Application 2009/0240113, which is incorporated herein by reference. An example of a wireless patch system configured for estimating energy expenditure has been described and includes sensors, electrodes, and accelerometers. This system measures a variety of physiological conditions including temperature, heart rate, respiratory rate, and skin conductivity and uses this information in an algorithm to calculate the number of calories consumed, the number of calories burned, and the net yield. See, e.g., U.S. Patent Application 2010/0049004, which is incorporated herein by reference. Other examples of calorie counters based on activity measurements have been described. See, e.g., U.S. Pat. Nos. 4,100,401; 4,159,416; 5,815,954; and 7,334,472, each of which is incorporated herein by reference. Other means for performing calorimetry include, but are not limited to, the Haldane gravimetric method, open-circuit calorimeter with mask, spirographic method, assessment of heat loss and oxygen consumption.

The one or more sensors of the device can be configured to send data regarding a physiological condition in the subject to the programmable microprocessor of the device or to a electronics module operably connected to the programmable microprocessor. Conversely, the electronics module can be configured to instruct the one or more sensors to collect and transmit data or other information regarding one or more physiological conditions or indicators thereof at specified regular intervals and/or when triggered by sensed events or by initiation of particular device activity. The device may further include information storage. For example, measurement of one or more physiological condition may be collected and stored at specified times on a daily basis with an associated time stamp. More than one physiological condition may be measured simultaneously and associated with one another during processing. For example, measurement of temperature, or a localized temperature of an associated nerve tissue or circulatory tissue, can be assessed at the same time as measurement of blood glucose levels. A temperature measurement can also be triggered by other sensor activity such as when a measured exertion level reaches a specified limit value or immediately following caloric intake.

Smart Pill 20 and Associated Encrypted Network 100

As mentioned previously and as shown in FIG. 1, the smart pill 20 itself is a self-contained electronic device comprising onboard sensors 22, bio-active substance modules (e.g., a MEMS drug delivery system) 24, an electronics module 26 and a power source (e.g., battery) 28. The electronics module 26 comprises a microprocessor (e.g., a micro controller) 26A, memory (e.g., flash memory, OTP-one time programmable memory, etc.) 26B, and wireless communication capabilities (e.g., a transponder) 26C having an antenna 26D. By way of example only, the smart pill 20 is implemented on a printed flex circuit 30 (see FIGS. 2A-2B) in which the antenna 26D is embedded therein. This flex circuit 30 is then rolled and formed into a capsule configuration, as shown most clearly in FIG. 2B. The smart pill 20 can also be implemented as a system-in-package (SiP) that can take several configurations (e.g., the form of a rolled printed flex board, etc.).

The devices that can communicate with the pill 20 are called programming terminals 27 which are linked to a central database 29 (via a wireless interface 29A) using a protected wireless encrypted network 100 (FIG. 1). In particular, the programming terminals 27 are wireless devices that the patient and the healthcare provider (e.g., pharmacist, physician, pill manufacturer) use to communicate with the pill 20. The device 27A is used by the patient and may comprise a smartphone supporting a secure software application for communicating with the pill to verify that the patient about to ingest the pill is the proper patient. The "app" on the device 27A is specifically configured and limited to patient-pill communication; thus, the patient is not enabled to alter the pill software other than to upload proper patient ID thereto. On the other hand, the device 27B is used by the healthcare provider and may also comprise a smartphone supporting a secure software application that provides the authorized healthcare provider with the ability to program the pill 20 to dispense API in accordance with physician prescription for the designated patient. It should be noted that the use of the phrase "patient interface device" or "patient level terminal" or "programming device" are directed to the devices 27, whether it be operated by the patient or by the healthcare provider. It should be further noted that the pill-to-pill communication (e.g., when ingested-see FIG. 9) is also part of this wireless encrypted network 100. The central database 29 stores, e.g., all the relevant pill information, tracks and enables its uses at all levels from manufacturer to patient, makes possible expiring date tracking and prevents unauthorized use of the pills. The smart pill comprises e.g., a printed flex circuit contain the micro controller with Flash memory, sensors, One Time Programmable memory, wireless communication and antenna, wrapped around drug compartment, e.g., MEMS pump, and battery.

Figure 2C:
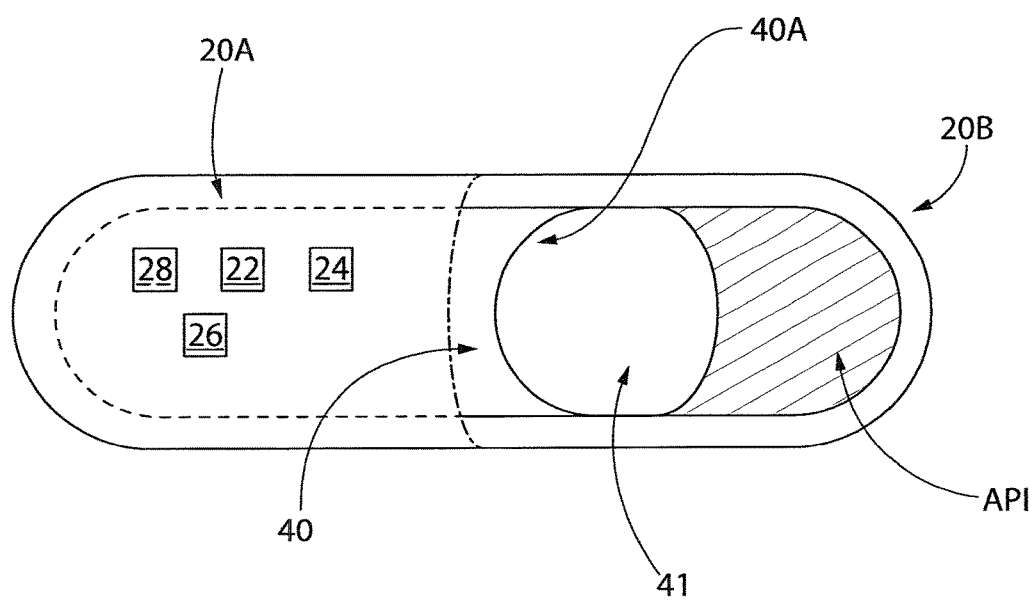
FIG. 2C is a functional diagram of the Smart Pill showing an electrolytic actuator for dispensing the active pharmaceutical ingredient (API), showing the pill in its initial state.
Figure 2D:
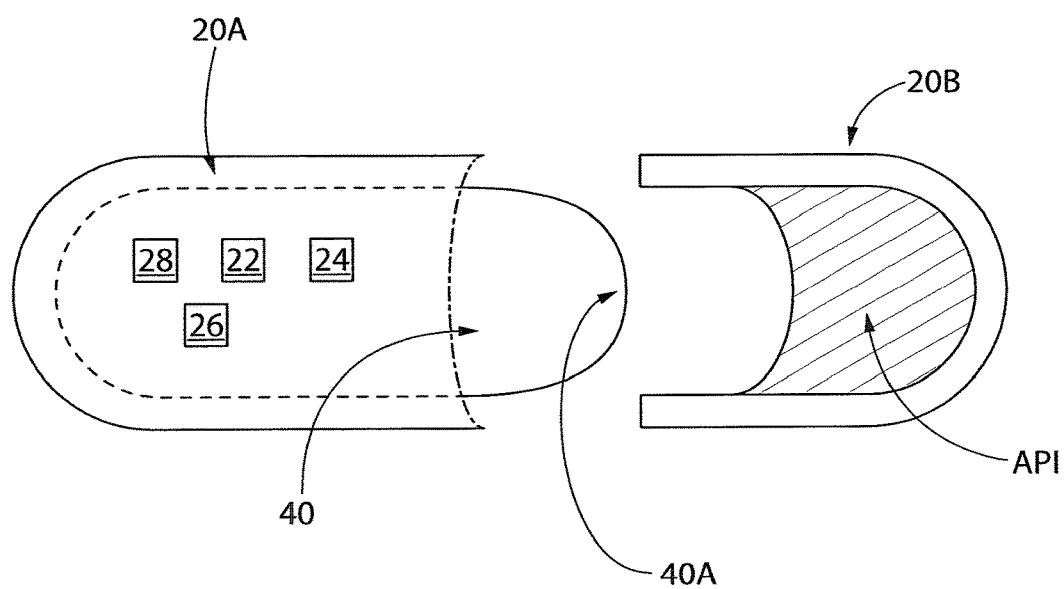
FIG. 2D is a functional diagram of the Smart Pill showing the electrolytic actuator activated for dispensing the API.
Figure 2E:
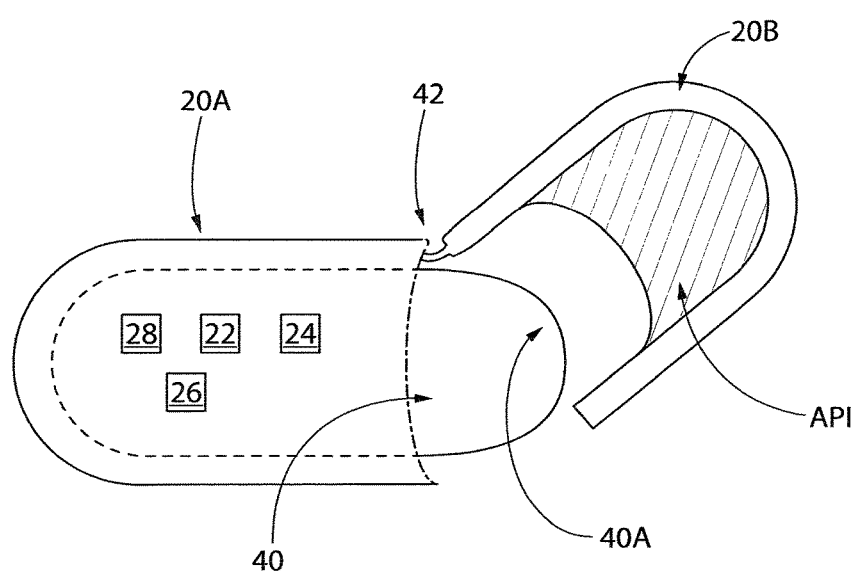
FIG. 2E is a functional diagram of the Smart Pill showing an alternative to maintaining the pill components connected together during and after the dispensing of the API.

An alternative to the pill's API dispensing mechanism may comprise the use of an electrolytic actuator, as shown most clearly in FIGS. 2C-2E. In particular, the pill comprises an electrolytic actuator 40 having an operative end 40A comprising an elastic membrane. In the pill's 20 initial state (FIG. 2C), the membrane 40A is separated from the API by a vacuum 41. When commanded by the microprocessor 26A, the electrolytic actuator 40 causes the elastic membrane to inflate/expand, thereby separating the pill's 20 capsule compartments 20A/20B to permit the dispensing of the API, as shown in FIG. 2D. Furthermore, an alternative to having the pill components 20A/20B separate upon actuator activation, an internal hinge 42 may be provided to keep these components 20A/20B connected while permitting dispensing of the API.

Multilevel Security System

The multilevel security system is implemented at pill level, e.g., as a set of flags than can be raised (enabled) with certain commands and only in sequence (for the first twelve flags). The delivery system of the active ingredient is triggered if and only if the configuration of the flags is the pre-defined one. Moreover the configuration of the flags can be modified only in sequence, one at a time.

The pill security system works, e.g., like a Yale locking system where each security flag F acts like a mechanical pin, preventing the activation (key turn) of the drug delivery system. Moreover, the modification of a security flag is possible only if the previous flags (i.e. the higher activation levels) are correctly configured.

The following flags (implemented as bit level variables are envisaged):

F0: Pill terminated
F1: Pill enabled by the drug manufacturer
F2: Pill enabled by the pharmacists.
F3: Timer for controlling prescription due date started: e.g., a generic 30 days (or 60 days). In the first version could be disabled.
F3B: Pill enabled at user level. It will be used in the future applications, for the moment just reserved.
F4: Pill is ingested [status]. In the simple way is decided if the temperature is over 36° C. for at least ten minutes. For the complex system is a decision based on the readings from different sensors.
F5-F8: Reserved for different triggers connected to various measurements that the pill will be able to perform.
F8-F11: Reserved for counting the pills in case of multiple pill dosage (further developments).
F12: No other pill detected used for one pill dose.
F13-F15: Counter for command authentication errors. It prevents brute force attacks on the pill, disabling it after a predefined number of non authenticated attempts of communications.

Pill Command Security System

The pill security system is e.g., implemented via One Time Programming (OTP) of silicon. In certain embodiments, it may comprise the following components:

PID: The pill has a unique ID (e.g., 16 ANSI alphanumeric characters should be enough) S1: Shared secret: Cryptographic key programmed in the silicon. AS1: authentication system using public challenge P1, expected result R1 and method of computing M1.

Figure 3:
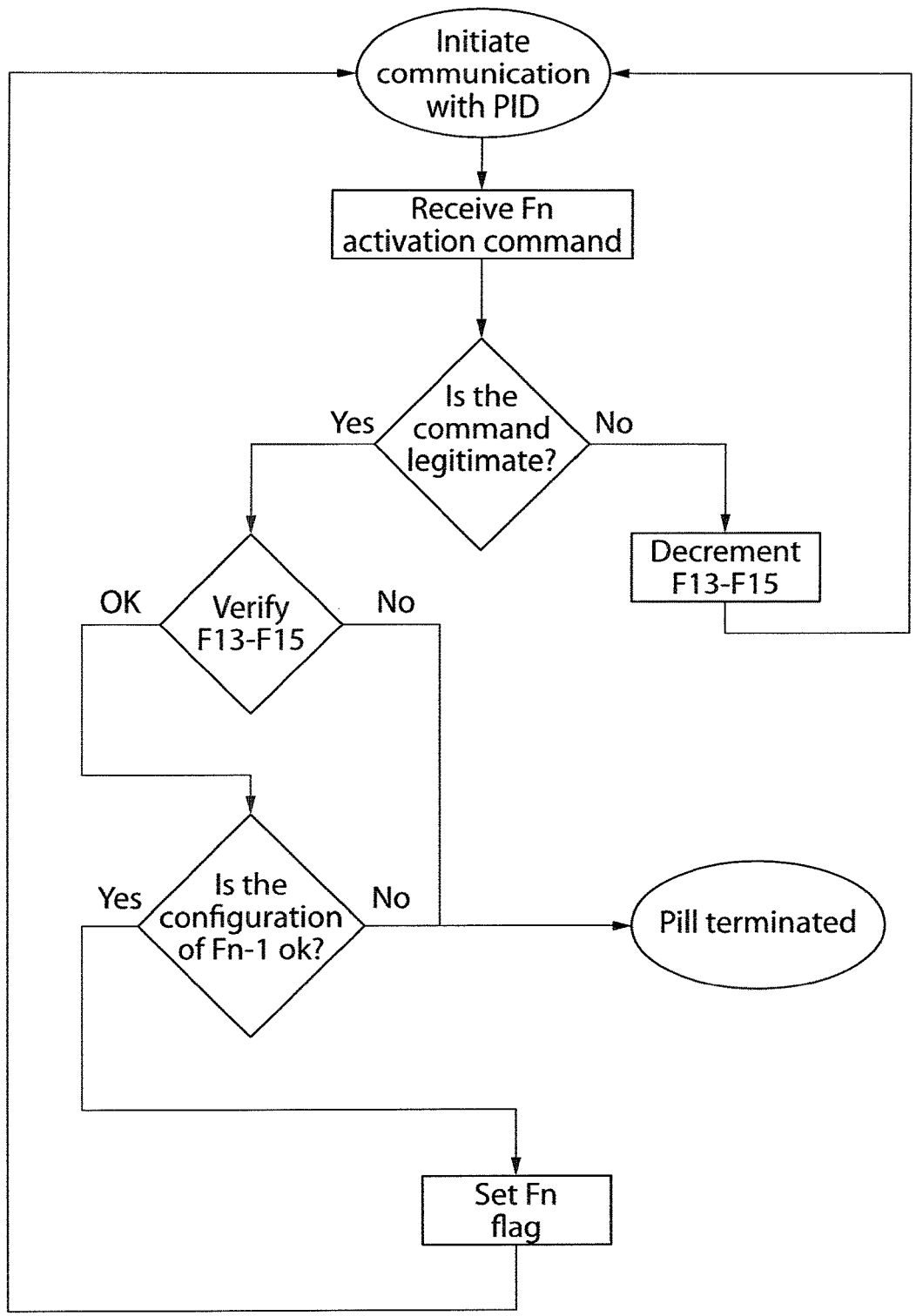
FIG. 3 is a flow diagram of the Smart Pill security flag operation.

The pill, presented with the pairs (P1, R1) uses the method M1 (for example symmetrical key algorithm for a good security, or pre-programmed random lookup table for a simpler one) and the secret seed S1 to compute the result of encryption of P1. If the result matches R1, the pair is a legitimate challenge and can authenticate the execution of one instruction. The authentication errors are used to increase the F13-F15 counter. The initial value of the F13-F15 can be pre-set thus setting the threshold for errors after which the pill considers that the communications attempts are only tampering tentatives. See FIG. 3.

The communication with the pill is not encrypted in order to have faster communication and enable emergency commands (see "Emergency overdose system").

Pill to Pill Communication

Figure 4:
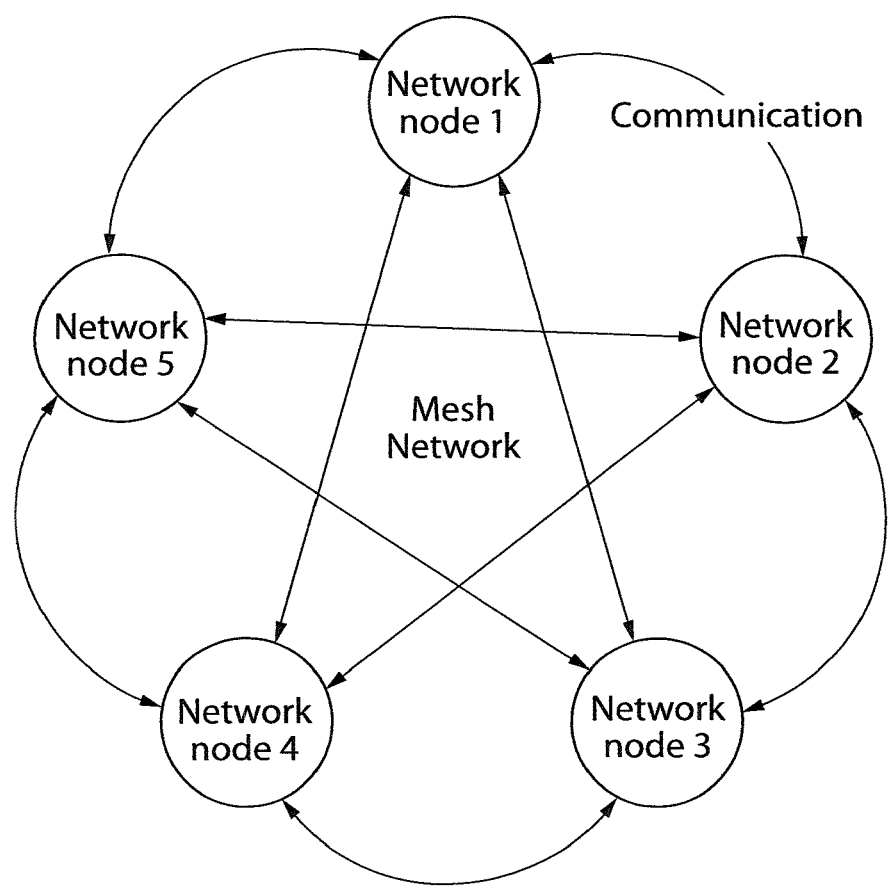
FIG. 4 is a functional diagram of a peer communication system using the Zigbee standard.
Figure 5:
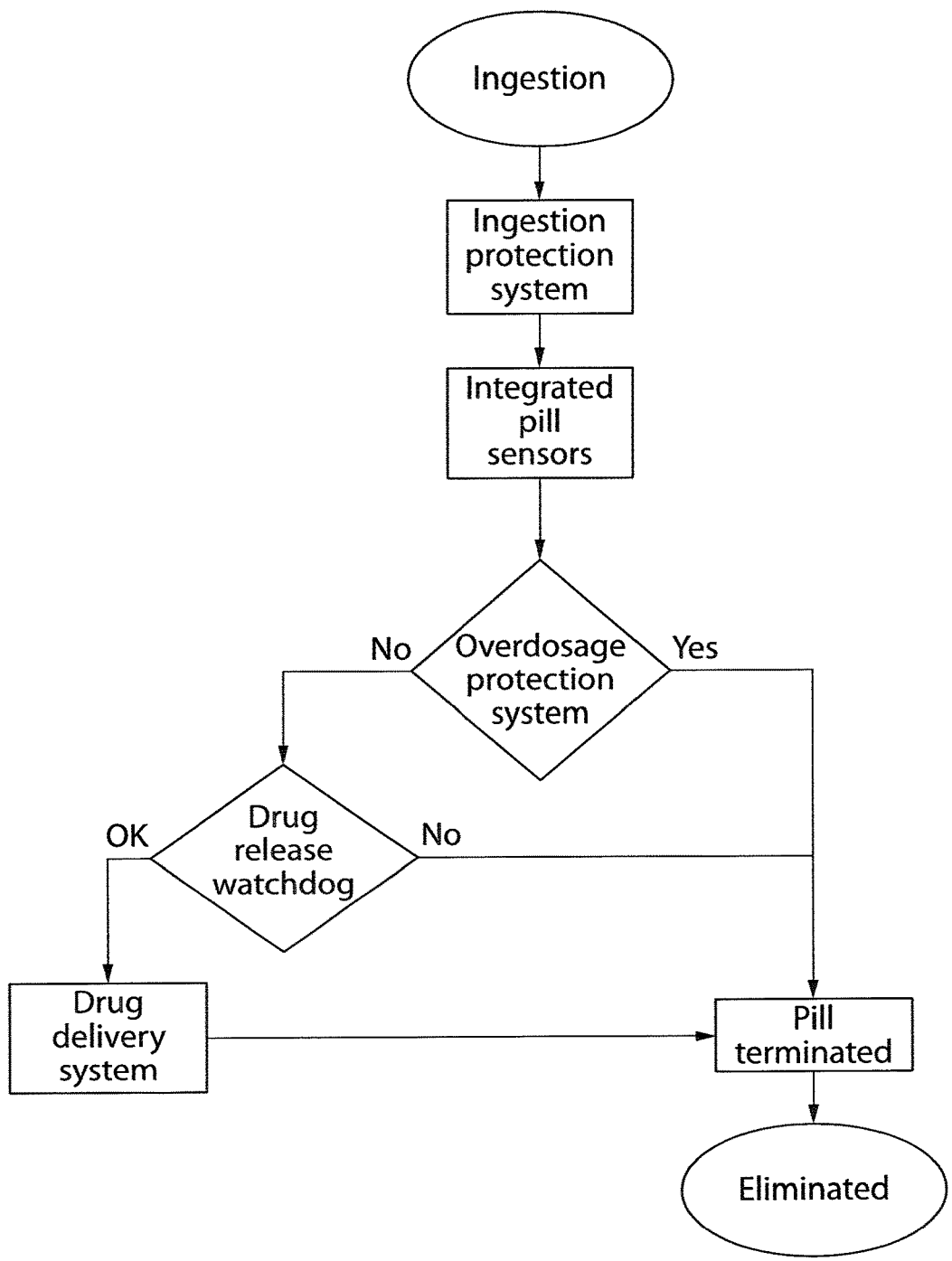
FIG. 5 is a flow diagram of Smart Pill termination and elimination.
Figure 6:
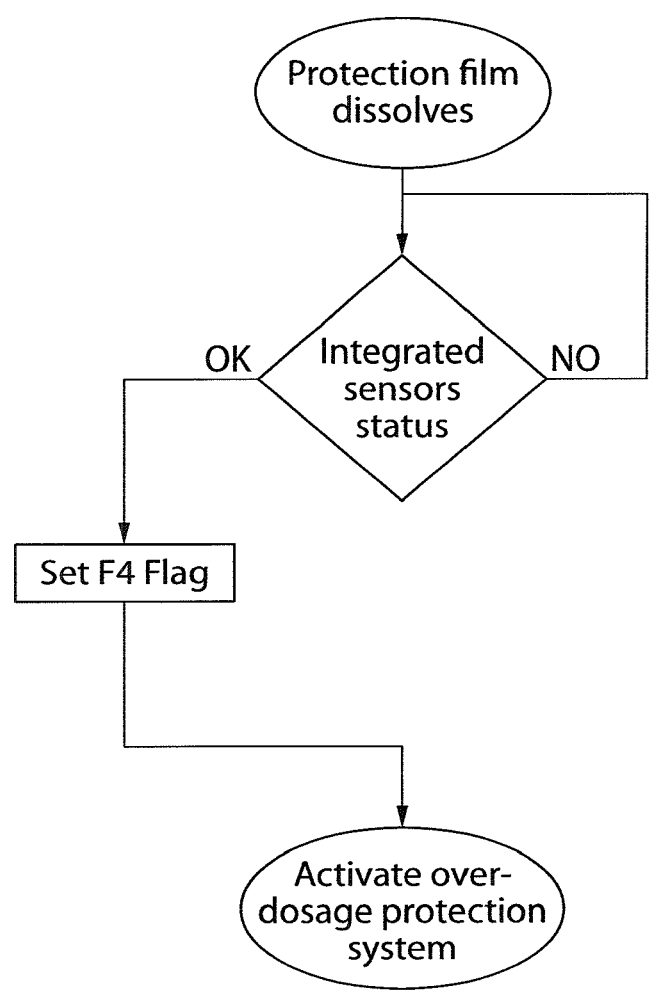
FIG. 6 is a flow diagram of activation of the Smart Pill "over dosage protection system" process.
Figure 7:
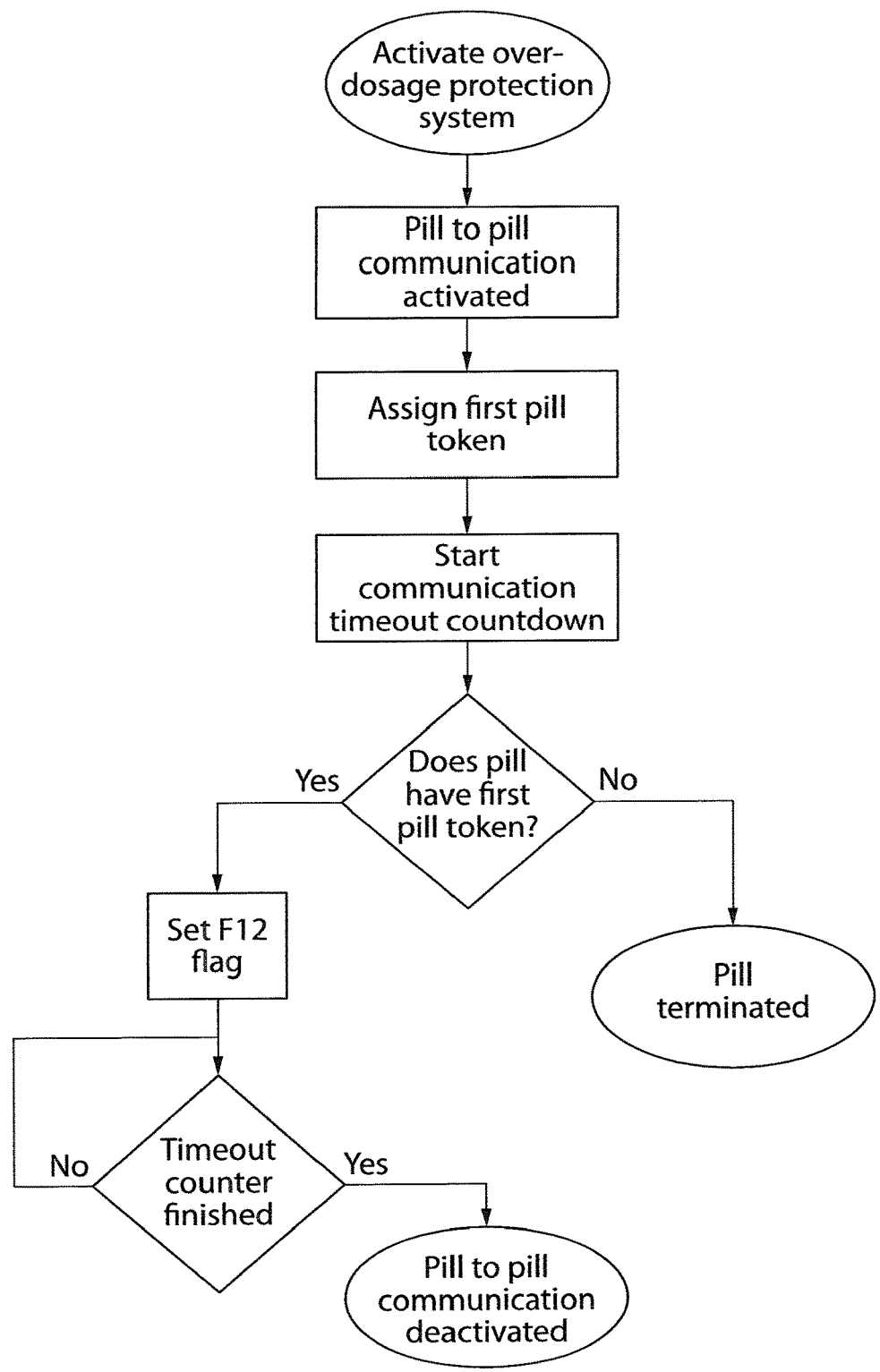
FIG. 7 is a flow diagram of the over dosage protection system.
Figure 8:
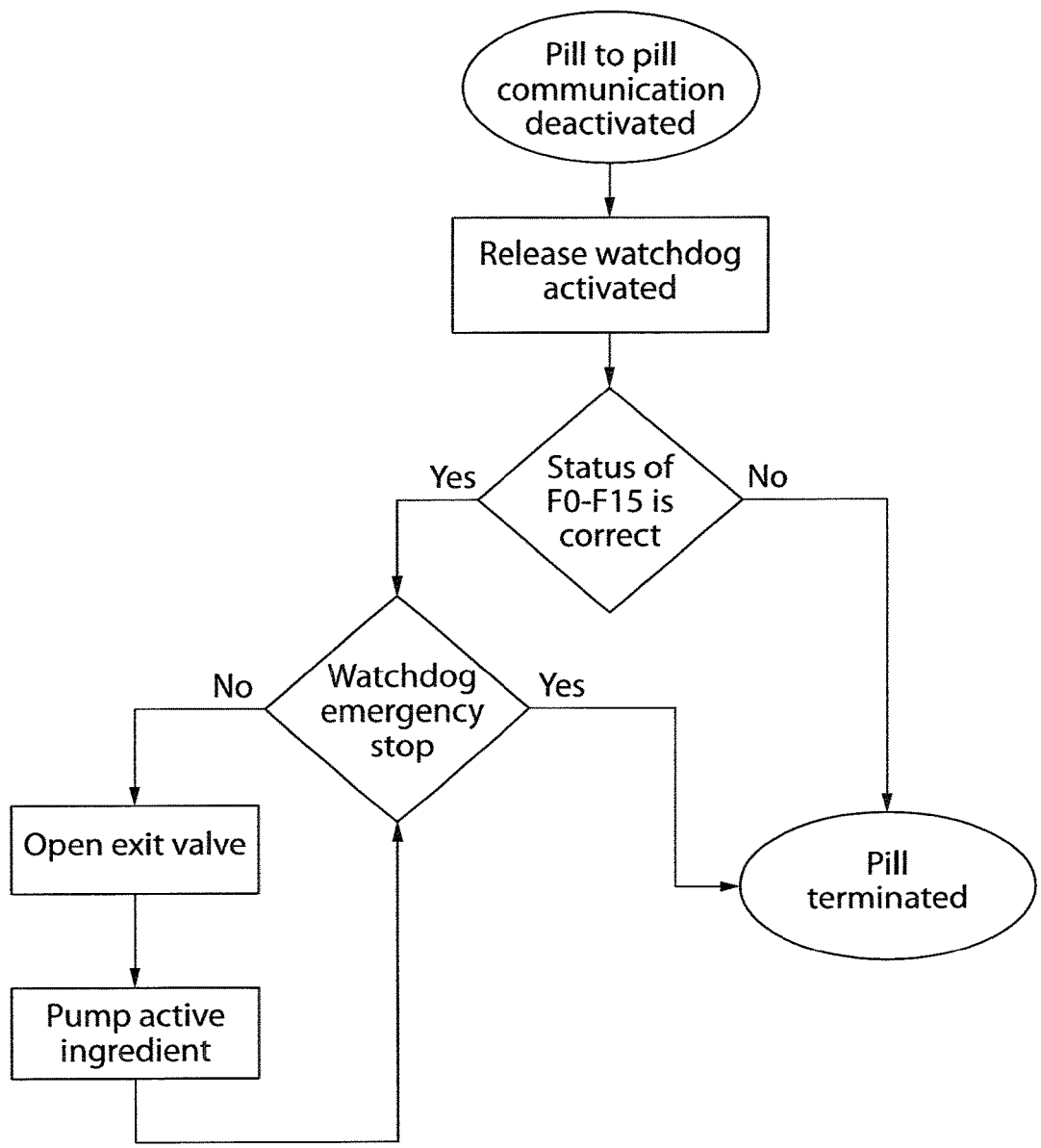
FIG. 8 is a flow diagram of the emergency overdose system.

A peer communication system (FIG. 4) using already existing systems will be implemented using a standard like ZigBee. ZigBee is a standard for communications that can be used to build M2M networks using small, low power, low cost battery operated digital radios. It is designed to work in harsh environments and is encrypted using a 128 Bit AES key. The ZigBee natively supports both star and tree networks, and generic Mesh networking. Using tree and mesh networks the coverage and communication distances can be dramatically extended allowing full warehouse coverage. It is a low power alternative to WiFi and Bluetooth connections.

In order to have a lighter and more energetic efficient communication one can use the EnOcean or even MyriaNed. MyriaNed is basically a self-organizing, "gossiping" Wireless Sensor Network. "An arbitrary node will broadcast a new message into the network. In general this will be initiated by a new sensor reading. This message will reach a number of nodes, but not all. Because the nodes also re-sent the received information, the information is spread through the network, and eventually the message is "known" by every node in the network. Epidemic message flooding through the network [is] called gossiping. Every node will have this 'behaviour', so at any time, every node is familiar with the state of all other nodes in the network, hence the state of the (distributed) system. This is called a shared state, which reflects the environmental situation that the network is in. So the system is situational aware. Applications of the net as substitute for RFID are also provided.

All of the above technologies offer layer five networking abstraction (net protocol). The smart pill system may comprise, e.g., a simpler layer 5 should be developed, or even use directly layer 4.

Terminal to Pill Communication

The terminal to pill is a point to point communication, thus requiring a much simpler system. The smart pills may comprise, e.g., two systems: a passive point to point, derived from, e.g., NFC/RFID standards, and a more complex Pill to Pill as indicated above which is activated only after ingestion, reducing the level of energy consumption during the pill lifetime. They are not necessary in the first of pills, but are envisaged for the following ones. All choices of networks presented allow the reading in any moment of the ingested pill unique ID (PID—see below) and thus the possibility to find during an emergency if pills were ingested and their type. (See FIGS. 5-9).

Set of Instructions in order to make the system safer only a [very] reduced number of commands are allowed:

get PID: returns pill's P.
enable F1, F2, F3 or F4 (P1,R1): enables the flags and starts the timer. Returns the operation exit code.

get F13-F15 (P1,R1): returns the number stored in F13-F15. In this way one can assess if the pill was subject to tampering or is disabled due to tampering attempts.

During the trial period there will be one more command:
get status (P1,R1): returns the status of all variables in the pill for enabling debug.

Command Authentication System

The "supplier/manufacturer" has a database with all the pills, univocally connecting PID, S1, M1, and all dug related data (type, batch, date, dosage etc.). When requested to supply an authentication challenge-response (P1,R1) it generates a random P1 and computes R1 using M1. It then supplies this pair over the delivery encrypted network that it used to give a command to the pill. The command exit is registered in the database, along with other information like programming terminal ID, patient terminal ID, pill status etc.

Communication/Authentication Network

The network is composed by the main database and programming terminals. The function and encryption is somewhat similar to the same to POS pay card terminals/network and includes:
terminal authentication (TERM ID)
encrypted communication channel
terminal physical anti tamper Emergency Overdose System Furthermore, when the smart pill 20 is ready for delivery (e.g., during an arbitrary defined interval), it is able to receive an emergency kill command which overrides all the security levels. This can happen only to a smart pill 20 that has passed the overdose protection system. As a result, the flag F0 changes to disable.

Alternative Protocol for Avoiding Inadvertent and Intentional Overdosing

As mentioned previously, FIG. 9 provides smart pill 20 (also referred to as "capsule") communication that designates the earliest ingested smart pill 20 as a "master" whose API is dispensed properly and all subsequently ingested smart pills 20 are identified in the time sequence of ingestion. With one smart pill 20 identified as the "master," all of the subsequent smart pills 20 are prevented from dispensing any further API, thereby preventing inadvertent as well as intentional overdosing. If the proper passage of time occurs following the proper dispensing of API from the "master" smart pill 20, the next-in-time ingested smart pill 20 becomes the "master" and is provided with the time sequence of ingestion data of subsequent smart pills 20 from the previous outgoing master smart pill 20.

It should be further understood that the identity of the healthcare provider that prepares/programs the smart pill (viz., see first two blocks in FIG. 9) must be included in the smart pill's 20 internal stored data, as well as any serial number from the smart pill manufacturer. This aspect of the smart pill configuration thus prevents counterfeiting since the smart pill's 20 source identity and preparer identity are memorialized within the smart pill 20 memory from its inception. Furthermore, this identity data cannot be manipulated or changed without the proper authorization. This is one of the purposes of the OTP memory, discussed previously, namely, to store initial critical pill data (e.g., source data including pill serial number, etc.) that cannot be erased, re-programmed, tampered with and/or modified, thereby preserving the provenance of the pill and preventing any counterfeiting of it.

Smart Pill Drug Delivery System

Figure 10A:
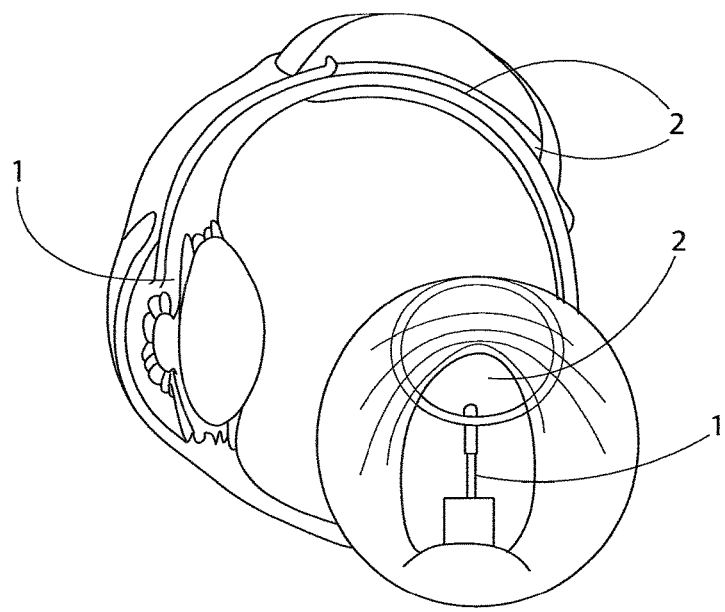
FIG. 10A is a functional diagram of an electrolytical pump, used in ophthalmological procedures, which can be used in the present invention.
Figure 10B:
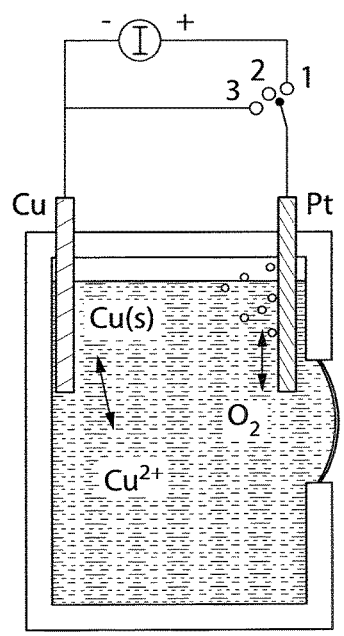
FIG. 10B is a functional diagram of the mechanism in FIG. 10A that creates the pump action via the creation of gas by the electrolysis of water.
Figure 10C:
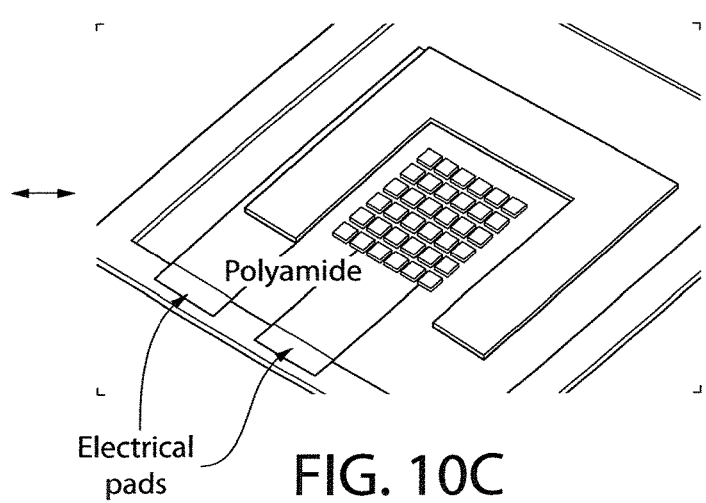
FIG. 10C is an exemplary implementation of the mechanism of FIG. 10B.

The smart pill drug delivery system may comprise an electrolytical pump, as used in opthalmological procedures. As shown most clearly in FIGS. 10A-10C, the pump displaces APIs (e.g., liquids, powders, etc.) by creating pressure through a volume increase due to gas creation through electrolysis of water. If required, the pressure system pushes a "piston" that effectively empties the pill's active ingredient compartment. The flow through a minute pipe is further controlled by a valve that, when closed, also blocks access of foreign liquid inside the smart pill 20. Furthermore, this drug delivery system can be used to dose the quantity of drug released or even establish a "neutralizer" release system by means of a secondary delivery system in the smart pill 20. An alternative embodiment may comprise a micromechanical actuator that slides a "cover" over the active ingredient. A further alternative may comprise, as shown in FIGS. 2C-2E, a self-contained electronic smart pill having the pill compartments 20A/20B that are held together by vacuum; to release the API, the electrolytic pump is activated, generating the gas that inflates the membrane and reduces the vacuum resulting in the components disengaging or remaining connected.

Treatment

The ingestible drug delivery device can be used in a method for treating a disorder in a vertebrate subject. The method can include releasing at least one bioactive substance to one or more tissues of the vertebrate subject with one or more bioactive substance module and/or deactivation modules, wherein the one or more bioactive substance module and/or deactivation modules are configured to release substance, and controlling the one or more bioactive substance module and/or deactivation modules with a programmable microprocessor configured to provide instructions to the one or more bioactive substance module and/or deactivation modules in response to information regarding one or more physiological conditions of the vertebrate subject. The method can further include providing one or more medicaments in combination with applying the device configured to release bioactive substance for the treatment of a disorder.

The method for treating a disorder in a subject can further include providing the ingestible drug delivery device as described herein comprising one or more medicaments configured to treat a disorder. The medicaments can include one or more medicaments for the treatment of veterinary and human conditions.

The method for treating a disorder in a subject can further include providing the ingestible drug delivery device as described herein wherein the one or more sensors may be configured to provide data to the electronics module and/or the programmable microprocessor regarding the plasma, blood, and/or tissue levels of bioactive substance. The programmable microprocessor may be configured to respond to the data received from the sensors by adjusting the one or more bioactive substance module and/or deactivation modules to appropriately release and/or not release the bioactive substance and/or deactivation substance in order to titrate, for example, blood and/or or plasma concentration, to for example, treat a condition or prevent overdose. Alternatively or in addition, the electronics module is configured to process the data from the sensor and provide instructions and/or programming to the programmable microprocessor to adjust the one or more bioactive substance module and/or deactivation modules to appropriately release the deactivation substance to, for example, deactivate the bioactive substance.

The method for treating a disorder in a subject can further include providing the ingestible drug delivery device as described herein wherein the ingestible drug delivery device may be configured to have a "controlled" quantity, e.g., a partial bioactive substance delivery in the instance where a full load of bioactive substance would go over, for example, a "threshold cutoff" blood, plasma, and/or tissue concentration of the bioactive substance but is not high enough to provide the correct dosage until the next dosing time point.

The method for treating a disorder in a subject can further include providing the ingestible drug delivery device as described herein wherein the ingestible drug delivery device may be configured to monitor the dosage prescribed by the health care provider for the diagnosed condition and it's effectivity with treating the particular symptom. For example, establishing two cutoff levels for pain sensing/alleviation and if the dosing is insufficient for the management for the amount of pain this information could be communicated back to the health care provider for an adjustment in the dosage and/or a change in the medicament selected.

Glucocorticoid Receptor Antagonists

Glucocorticoid receptor antagonists bind to the receptor and prevent glucocorticoid receptor agonists from binding and eliciting GR mediated events, including transcription. RU486 is an example of a non-selective glucocorticoid receptor antagonist.

Compounds having high glucocorticoid receptor binding affinity and, in addition, high in vivo anti-glucocorticoid activity, while having, for example, low androgenic and progestagenic activities are disclosed in U.S. Pat. No. 6,011,025, incorporated herein by reference in its entirety. ORG 34517 is an example of a compound with high glucocorticoid receptor binding affinity while having low androgenic and progestagenic activities. Therapeutic compositions and methods using ORG 34517 are disclosed in U.S. Pat. No. 8,986,677, incorporated herein by reference in its entirety.

It has been found that 11-(substituted phenyl)-estra-4,9-diene derivatives of formula I

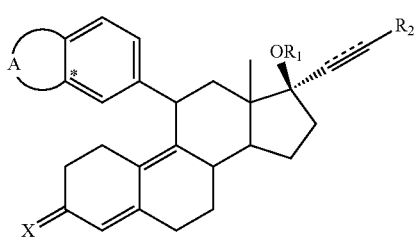

(I)

wherein

A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond, show specific and high glucocorticoid receptor binding affinity and are highly active in vivo showing predominant anti-glucocorticoid activity.

The compounds lack appreciable affinity for mineralocorticoid, progesterone, estrogen and androgen receptors, indicating a clean side effect profile.

The 11-(substituted phenyl)-estra-4,9-diene derivatives of the invention can be used in the prevention and treatment of glucocorticoid dependent diseases or symptoms, like Cushing syndrome, diabetes, glaucoma, sleep disturbances, depression, anxiety, atherosclerosis, hypertension, adiposity, osteoporosis and withdrawal symptoms from narcotics and their mixtures. It should be noted that U.S. Pat. No. 8,986,677 is incorporated by reference herein in its entirety.

Preferred compounds according to this invention are 11-(substituted phenyl) estra-4,9-diene derivatives, wherein the heteroatom(s) are (is) O, the 5- or 6-membered ring being optionally substituted with one or more fluorine atoms; R1 is H; and X is O or NOH.

More preferred compounds are 11-(substituted phenyl) estra-4,9-diene derivatives wherein A is a residue of a 5-membered ring. Particularly preferred are 11-(substituted phenyl) estra-4,9-diene derivatives wherein A contains 2 heteroatoms being O.

Especially preferred are 11-(substituted phenyl) estra-4,9-diene derivatives wherein R2 is methyl and the interrupted line represents a bond.

The most preferred compound is (11β,17β)-11-(1,3-benzodioxol-5-yl)-17-hydroxy-17-(1-propynyl) estra-4,9-dien-3-one (ORG 34517).

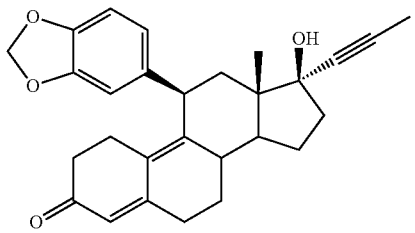

ORG 3457

The term halogen means a fluorine, chlorine, bromine or iodine atom. Fluorine is the preferred halogen in ring A and when R2 is halogen, chlorine is preferred.

The terms (1-4C)alkyl and (1-8C)alkyl, as used in the definitions of R1 and R2, respectively, mean alkyl groups having 1-4 and 1-8 carbon atoms, respectively, for example methyl, ethyl, propyl, isopropyl, butyl, sec-butyl, tert-butyl, pentyl, neopentyl, hexyl, octyl.

The 11-(substituted phenyl)-estra-4,9-diene derivatives according to the present invention can be prepared by a process wherein a compound of formula II

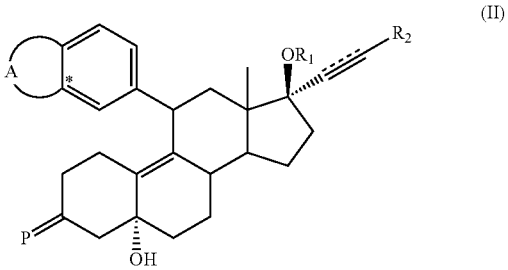

(II)

wherein A, R2 and the interrupted line have the meanings as previously defined, R1 is H, and P is a protected keto-group, is dehydrated and deprotected, after which the 17β-OH is optionally esterified by reaction with an appropriate carboxylic acid to give a derivative wherein R1 is 1-oxo(1-4C)alkyl, and optionally the 3-oxo group is converted into the corresponding 3-hydroxy- or 3-oxime derivative. The 3-oxo group can be reduced to form the 3-hydroxy-derivative by using a suitable reducing agent, such as sodium borohydride. The 3-oxime derivatives can be prepared by hydroxylamine treatment in a suitable solvent, like pyridine.

The derivatives of formula II may be prepared according to well known methods described and used for the preparation of steroids.

A suitable process for the preparation of derivatives of formula II starts from estra-4,9-diene-3,17-dione. Selective reduction of the 17-keto group to 17β-OH, 17α-H, e.g. with sodium borohydride, followed by protection of the 3-keto group, e.g., by ketalisation with ethyleneglycol, triethylorthoformate and p-toluenesulfonic acid, and oxidation of the 17-hydroxy group, e.g. with pyridinium chlorochromate, provides the 3-ketoprotected estra-5(10),9(11)-diene-3,17-dione. Alkynylation at the 17-position (yielding a 17α-alkynyl,17β-OH derivative), followed by epoxidation of the 5(10) double bond, e.g. with hydrogen peroxide, trifluoroacetophenone, and pyridine in dichloromethane according to the method as disclosed in European patent application EP 0 298 020, provides the 3-ketoprotected 5α,10α-epoxy-17α-alkynyl-17β-hydroxy-estr-9(11)-ene-3-one.

Subsequently, compounds of formula II are formed from this epoxide derivative, for example by reaction with an organometallic compound of the formula

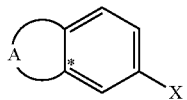

wherein X is a (alkali)metal, like lithium, or a magnesiumhalide, preferably magnesium bromide.

Suitable protective groups and methods to remove these groups are known in the art, for example from T. W. Green: Protective Groups in Organic Synthesis (Wiley, N Y, 1981). Particularly suitable protective groups for the protection of keto groups are acetals, e.g. 1,2-ethylene ketal.

The specificity of ORG 34517 for GR blockade, without significant cross-binding to other related steroidal hormone receptors (such as those for estrogen and progesterone), eliminates the likelihood of significant toxicities and side effects. Indeed, none were identified in all the substantial phase I and phase II clinical trials that already have been performed with the compound. Because the drug is envisioned as being used in limited dosing over time, coordinated with the intermittent dosing strategies typical for chemotherapeutic agents, the GR blockade also would not lead to significant alteration of HPA-axis functioning, with rapid restitution of the HPA-axis to baseline following dosing.

Combination Therapy

Compositions and methods for treating GC-responsive conditions, including for example, the prevention or addiction induced anxiety and withdrawal side effects as a therapeutic, for wound healing and transplants, for the prevention or treatment of stress induced osteoporosis and for the rapid healing of bone related injuries, and regenerative therapy, in a subject are provided by the present invention.

Methods of treating a GC-responsive condition in a subject are provided according to embodiments of the present invention which includes administering, the ingestible drug delivery device of the invention comprising, e.g., in combination, a GR antagonist and at least one additional therapeutic agent as set forth herein. The phrase "administering in combination" as used herein refers to any form of administration of one or more GR antagonists and at least one additional therapeutic agent as set forth herein.

Addiction and Withdrawal

The present invention relates to methods of and compositions for treating and relieving symptoms associated with substance abuse and withdrawal. The present invention relates to methods of and compositions for treating addiction to, for example, alcohol, drugs, caffeine, sugar, food, nicotine, opiates, and/or marijuana, etc.

Treatment of addiction to prescription medications (e.g., narcotics such as oxycodone, oxycontin, Vicodin), particularly when their use is initiated for the treatment of acute or chronic pain syndromes, can be difficult. Not only is there significant withdrawal following chronic use, but the risk of relapse is significantly increased by the clinical need for continued use.

Substance addiction and abuse is a multi-factorial neurological disease. Over time, repeated exposure to various substances, both endogenous and exogenous, causes modification of the neurotransmission circuits and adaptations in post-receptor signaling cascades. There are several effects of this neuronal modification. Among them, there is a reduction in the ability of natural rewards to activate the reward pathways leading to depressed motivation and mood and an increased compulsion to compensate for the physiological change.

While the common perception underlying addiction is that of a "reward circuit", pleasure may not necessarily be a strong enough impetus to drive people towards their addictions. Rather, addictive behavior arises from an intense desire to manage and/or avoid the anxiety that arises when someone is experiencing withdrawal.

Traditional treatments for substance dependency, such as benzodiazepine abuse, have been based upon cognitive-behavioral therapy or drug therapy, or a combination thereof. Conventional methods of treatment fail, however, in that they do not address the physiochemical changes that occur with addiction and dependence. Thus, conventional treatments for controlling withdrawal symptoms and cravings for addictive substances have had limited success and often have undesirable side effects.

What is therefore needed are improved methods of, and compositions and/or devices for preventing addiction to, and physiological dependence upon addictive substances. What is also needed is an improved treatment methodology for controlling cravings and withdrawal symptoms caused by substance abuse.

Accordingly, the invention provides methods of, and compositions and/or ingestible devices for, preventing addiction to, and physiological dependence upon addictive substances. Also provided are methods of and compositions for an improved treatment methodology for controlling cravings and withdrawal symptoms caused by substance abuse.

The present invention relates to the use of, for example, ingestible drug delivery device of the invention comprising, e.g., cortisol blockers (glucocorticoid receptor [GR] antagonists) for the prevention or addiction induced anxiety and withdrawal side effects as a therapeutic and in concert with a diagnostic.

The ingestible drug delivery device of the invention may be administered orally. The ingestible drug delivery device of the invention may comprise, e.g. an active pharmaceutical ingredient in combination with pharmaceutically suitable auxiliaries, e.g. as described in the standard reference, Gennaro et al., Remington's Pharmaceutical Sciences. By means of pharmaceutically suitable liquids the compounds can also be applied in the form of a solution, suspension, emulsion, e.g. for use in an the ingestible drug delivery device of the invention.

Suitable carriers with which the compositions can be administered include lactose, starch, cellulose derivatives and the like, or mixtures thereof, used in suitable amounts.

The present invention reflects the role of endogenous glucocorticoids (GCs) in withdrawal from substances of abuse and addictive substances (hereafter referred to as "drug" or "drugs", inclusive of, but not restricted to, alcohol, nicotine, caffeine, cocaine (including crack cocaine), *cannabis*, amphetamines (including crystal methamphetamine), opiates and opiate analogues (including heroine, oxycodone, hydrocodone, hydromorphone, methadone), dextromethorphan, benzodiazepines, ecstacy (MDMA), GHB, barbiturates, khat, kratom, PCP, LSD, ketamine, peyote, mescaline, psilocybin, rohypnol, *Salvia divinorum*, antidepressants, anti-anxiety 5 medications, sleep aids, allergy medications.

Combination treatments of withdrawal from narcotics and subsequent prevention of relapse of, e.g., narcotic use can be accomplished by:

1. treatment with ORG34517 prior to, or at time of withdrawal of narcotic, preventing symptoms of withdrawal (e.g., U.S. Pat. No. 8,986,677, which is incorporated by reference herein);

followed by:

2. restoration of narcotic use using "smart pill" encapsulation of prescription narcotic, to establish:
    a. new baseline dose for treatment of pain syndromes
    b. prevent self medication with higher doses
    c. prevention of overdose
    d. tracking of narcotics in case of loss/theft/illegal transfer using "smart pill" encoding of intended patient, intended dose, and loading pharmacist and pharmacy.

Increased circulating levels of GCs may relate to direct elevating effects of substances of abuse or from stress-associated GC elevations in response to neuropsychiatric and physical stresses of withdrawal.

The present invention relates to using the ingestible drug delivery device of the invention in a method of co-administration of a selective GC receptor antagonist, such as ORG34517 administered during the active intoxication phase of drug use, prior to drug use, or after cessation of drug use to reduce neuropsychiatric and physical symptoms of withdrawal, such as anxiety, hallucinations, dysphoria, depression, delirium tremens, chills, shakes, tremors, akathisia, restlessness, restless leg syndrome, musculoskeletal aches and pains, cramping, chills, weakness, using the ingestible drug delivery device of the invention.

The present invention relates to single dose of GC receptor antagonist or sustained administration of GC receptor antagonist for hours, days, weeks, or months for prevention of and/or treatment of symptoms of drug withdrawal using the ingestible drug delivery device of the invention.

The ingestible drug delivery device of the invention may be designed for co-administration with anti-anxiety drugs and anti-depressant drugs to better control sporadic episodes, flare-ups of anxiety or depression. The invention provides regular co-administration of the ingestible drug delivery device of the invention with anti-anxiety and/or anti-depressant drugs using the ingestible drug delivery device of the invention.

The present invention may also be used in concert with a diagnostic (for example, a diagnostic test using saliva, blood, plasma, serum, urine or tears as substrate) for the specific constituent i.e.: alcohol, cocaine, caffeine, nicotine, etc. to monitor the specific level of said constituent in the individual to prevent from occurrences of anxiety and withdrawals.

The present invention may also be used in concert with a diagnostic (for example, a diagnostic test using saliva, blood, plasma, serum, urine or tears as substrate) for cortisol to determine which individuals have elevated circulating cortisol or dysregulated cortisol and may therefore be most likely to benefit from administration of GC receptor antagonist.

The present invention may be packaged for use alone, as a single dose (by prescription or over the counter), as a limited number of timed doses in packaging designed to specifically guide self-administration, and in combination with drug or cortisol diagnostic test (using saliva, blood, plasma, serum, urine or tears as substrate) for self-administration or administration by health care professional or technician.

Bioactive Substances

The ingestible drug delivery device of the invention may comprise one or more bioactive substances. The bioactive substance may include active compounds, and compounds for veterinary and human use, such as but not limited to: pharmaceutical actives, nutriceuticals, cosmeceuticals, cosmetics, complementary medicines, natural products, foods, vitamins, nutrients, biologics, amino acids, proteins, peptides, nucleotides, and nucleic acids. In a preferred form the bioactive substance is adapted for oral administration.

In a preferred embodiment of the invention, the bioactive substance is an organic compound. In a highly preferred embodiment of the invention, the bioactive substance is an organic, therapeutically active compound for human use. In another embodiment of the present invention, the bioactive substance is an inorganic compound. When the biological active material is a drug, it can be of a neutral species, basic or acidic as well as salts of an acid or base. This invention is not limited to any drug specific class, application type, chemical type or function grouping.

The bioactive substance is ordinarily an agent for which one of skill in the art desires improved fast dissolution for oral administration. The bioactive substance may be a conventional active agent or drug.

The ingestible drug delivery device of the invention can be configured for the delivery of liquid, semi-liquid or solid forms of drug or all three. Solid forms of drug can include both powder or pellet. Semi liquid can include a slurry or paste. The drug can be contained within a cavity of the capsule, or in the case of the liquid or semi-liquid, within an enclosed reservoir. In some embodiments, the capsule can include a first second, or a third drug (or more). Such drugs can be contained within the tissue penetrating member lumen (in the case of solids or powder) or in separate reservoirs within the capsule body. The bioactive substance may be in a powder, liquid, and/or gel The ingestible drug delivery device of the invention may comprise pharmaceutical compositions comprising a bioactive substance which may comprise at least one or more active pharmaceutical ingredients (API), as well as optionally, also include one or more excipients. Excipients include physiologically acceptable carriers, adjuvants or vehicles, collectively referred to as carriers. The compositions can be formulated in solid, gel, powder, or liquid form.

Excipients can include one or more binding agents, filling agents, lubricating agents, suspending agents, sweeteners, flavoring agents, preservatives, buffers, wetting agents, disintegrants, effervescent agents and other excipients. Such excipients are known in the art. Examples of filling agents include lactose monohydrate, lactose anhydrous, microcrystalline cellulose, such as Avicel® PH101 and Avicel® PH102, microcrystalline cellulose and silicified microcrystalline cellulose (ProSolv SMCC®), and various starches; examples of binding agents are various celluloses and cross-linked polyvinylpyrrolidone. Suitable lubricants, including agents that act on the flowability of the powder to be compressed, include colloidal silicon dioxide, such as Aerosil® 200, talc, stearic acid, magnesium stearate, calcium stearate and silica gel. Sweeteners can be any natural or artificial sweetener, such as, for example, sucrose, xylitol, sodium saccharin, cyclamate, aspartame, sucralose, maltitol and acsulfame. Examples of flavoring agents include Magnasweet® (trademark of MAFCO), bubble gum flavor, and fruit flavors, and the like. Examples of preservatives include potassium sorbate, methylparaben, propylparaben, benzoic acid and its salts, other esters of parahydroxybenzoic acid, such as butylparaben; alcohols, such as ethyl or benzyl alcohol. Suitable diluents include pharmaceutically acceptable inert fillers, such as microcrystalline cellulose, lactose, dibasic calcium phosphate, saccharides and/or mixtures of any of the foregoing. Examples of diluents include microcrystalline cellulose, such as Avicel® PH101 and Avicel® PH1 02; lactose, such as lactose monohydrate, lactose anhydrous, and Pharmatose® DCL21; dibasic calcium phosphate, such as Emcompress®; mannitol; starch; sorbitol; sucrose; and glucose. Suitable disintegrants include lightly crosslinked polyvinyl pyrrolidone, corn starch, potato starch, maize starch, and modified starches, croscarmellose sodium, cross-povidone, sodium starch glycolate and mixtures thereof. Examples of effervescent agents are effervescent couples, such as an organic acid and a carbonate or bicarbonate. Suitable organic acids include, e.g., citric, tartaric, malic, fumaric, adipic, succinic and alginic acids and anhydrides and acid salts. Suitable carbonates and bicarbonates include, e.g., sodium carbonate, sodium bicarbonate, potassium carbonate, potassium bicarbonate, magnesium carbonate, sodium glycine carbonate, L-lysine carbonate and arginine carbonate. Alternatively, only the sodium bicarbonate component of the effervescent couple may be present.

The ingestible drug delivery device of the invention may comprise pharmaceutical compositions of the bioactive agents which may comprise at least one or more of the following: (a) one or more inert excipients (or carriers), such as sodium citrate or dicalcium phosphate; (b) fillers or extenders, such as starches, lactose, sucrose, glucose, mannitol and silicic acid; (c) binders, such as carboxymethylcellulose, alginates, gelatin, polyvinylpyrrolidone, sucrose and acacia; (d) humectants, such as glycerol; (e) disintegrating agents, such as cross-linked starches, polyvinylpyrrolidone XL, agar-agar, calcium carbonate, potato or tapioca starch, alginic acid, certain complex silicates and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate or mixtures thereof. For capsules, tablets and pills, the dosage forms may also comprise buffering agents.

Liquid forms for oral administration include pharmaceutically acceptable emulsions, solutions, suspensions, syrups and elixirs. In addition, the liquid dosage forms may include excipients such as inert diluents commonly used in the art, such as water or other solvents, co-solvents, solubilizing agents and emulsifiers. Non-limiting examples of solvents and co-solvents include ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol and dimethyl isosorbide, polyethyleneglycols, fatty acid esters of sorbitan, or mixtures of these substances, and the like. The composition can also include adjuvants, such as wetting agents, emulsifying and suspending agents, sweetening, flavoring and perfuming agents. Liquid formulations can also be prepared by dissolving or suspending one or the combination of Bioactive substances in a conventional liquid vehicle acceptable for pharmaceutical administration so as to provide the desired dosage in one to four teaspoonful.

Dosage forms can be administered to the patient on a regimen of, for example, one, two, three, four, five, six, or other doses per day In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in the bioactive substance composition are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Examples of bioactive substances suitable for use in the invention include actives, biologics, amino acids, proteins, peptides, nucleotides, nucleic acids, and analogues, homologs and first order derivatives thereof. The bioactive substance can be selected from a variety of known classes of drugs, including, however not limited to: anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, cough suppressants (expectorants and mucolytics), diagnostic agents, diagnostic imaging agents, diuretics, dopaminergics (anti-Parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of bioactive substances and a listing of species within each class can be found in Martindale's 'The Extra Pharmacopoeia', 31st Edition (The Pharmaceutical Press, London, 1996), and the 'Physician's Desk Reference' (60th Ed., 2005), both specifically incorporated by reference and familiar to those of skill in the art. The active agents are commercially available and/or can be prepared by techniques known in the art.

Additionally, examples of suitable bioactive substances include, however are not limited to, those listed below: Analgesics and anti-inflammatory agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac. Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole. Anti-arrhythmic agents: amiodarone HCl, disopyramide, flecamide acetate, quinidine sulphate. Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphad iazine, sulphafurazole, sulphamethoxazole, sulphapyridine, tetracycline, trimethoprim. Anti-coagulants: dicoumarol, dipyridamole, nicoumalone, phenindione. Anti-depressants: amoxapine, ciclazindol, maprotiline HCl, mianserin HCl, nortriptyline HCl, trazodone HCl, trimipramine maleate. Anti-diabetics: acetohexamide, chlorpropamide, glibenclamide, gliclazide, glipizide, tolazamide, tolbutamide. Anti-epileptics: beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid. Antifungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid. Anti-gout agents: allopurinol, probenecid, sulphinpyrazone. Anti-hypertensive agents: amlodipine, benidipine, darodipine, diltiazem HCl, diazoxide, felodipine, guanabenz acetate, indoramin, isradipine, minoxidil, nicardipine HCl, nifedipine, nimodipine, phenoxybenzamine HCl, prazosin HCl, reserpine, terazosin HCl. Anti-malarials: amodiaquine, chloroquine, chlorproguanil HCl, halofantrine HCl, mefloquine HCl, proguanil HCl, pyrimethamine, quinine sulphate. Anti-migraine agents: dihydroergotamine mesylate, ergotamine tartrate, methysergide maleate, pizotifen maleate, sumatriptan succinate. Anti-muscarinic agents: atropine, benzhexyl HCl, biperiden, ethopropazine HCl, hyoscine butyl bromide, hyoscyamine, mepenzolate bromide, orphenadrine, oxyphencylcimine HCl, tropicamide. Anti-neoplastic agents and immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone. Anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole. Anti-thyroid agents: carbimazole, propylthiouracil. Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone. Beta-Blockers: acebutolol, alprenolol, atenolol, labetalol, metoprolol, nadolol, oxprenolol, pindolol, propranolol. Cardiac Inotropic agents: aminone, digitoxin, digoxin, enoximone, lanatoside C, medigoxin. Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone. Diuretics: acetazolamide, amiloride, bendrofluazide, bumetanide, chlorothiazide, chlorthalidone, ethacrynic acid, frusemide, metolazone, spironolactone, triamterene. Anti-Parkinson agents: bromocriptine mesylate, lysuride maleate. Gastro-intestinal agents: bisacodyl, cimetidine, cisapride, diphenoxylate HCl, domperidone, famotidine, loperamide, mesalazine, nizatidine, omeprazole, ondansetron HCl, ranitidine HCl, sulphasalazine. Histamine H1-receptor antagonists: acrivastine, astemizole, cinnarizine, cyclizine, cyproheptadine HCl, dimenhydrinate, flunarizine HCl, loratadine, meclozine HCl, oxatomide, terfenadine, triprolidine. Lipid regulating agents: bezafibrate, clofibrate, fenofibrate, gemfibrozil, probucol. Local anaesthetics: Neuromuscular agents: pyridostigmine Nitrates and other antianginal agents: amyl nitrate, glyceryl trinitrate, isosorbide dinitrate, isosorbide mononitrate, pentaerythritol tetranitrate. Nutritional agents: betacarotene, vitamin A, vitamin B2, vitamin D, vitamin E, vitamin K. Opioid analgesics: codeine, dextropropyoxyphene, diamorphine, dihydrocodeine, meptazinol, methadone, morphine, nalbuphine, pentazocine, midazolam, fentanyl, codeine, buprenorphine, tramadol, fentany, hydromonorphone, morphine, oxycodone/naloxone, opiate, opium, acetyldihydrocodeine, alfentani, allylprodine, alphamethylfentanyl, alphaprodine, benzylmorphine, betaprodine, bezitriamide, buprenorphine, butorphanol, bremazocine, carfentan (carfentanyl), contin, dextromoramide, dextropropoxyphene, dezocine, diacetylmorphine, diamorphine, dihydrocodeine, dihydromorphine, dihydromorphone, diphenoxylate, dipipanone, enadoline, ethylketazocine, ethylmorphine, etonitazene, etorphine, fentanyl, heroin, hydrocodone, hydromorphin (hydromorphine), hydromorphone, ketazocine, ketobemidone, lefetamine, levomethadon, levomethadyl, levomethorphan, levor-phanol, loperamide, meperidine, meptazinol, methadone, methadyl, methylmorphine, morphin (morphine), nalbuphine, narcotic, nicocodeine, nicomorphine, normorphine, noscapin, ohmefentanyl, oripavine, oxycodone, oxycontin, oxymorphone, papaveretum, papaverin, pentazocine, percocet, peronine, pethidine, phenazocine, phencyclidine, pholcodine, piritramid (priitramidine), prodine, promedol, propoxyphene, remifentanil, sufentanil, tapentadol, thebaine, tilidine, tramadol, ultracet, morphine, codeine, diyhydrocodeine, diacetylmorphine, hydrocodone, hydomorphone, levorphanol, oxymorphone, alfentanil, buprenorphine, butorphanol, fentanyl, sufentanyl, meperidine, methadone, nabulfina, propoxyphene, pentazocine and their pharmaceutically acceptable salt derivatives. Benzodiazepines: diazepam, alprazolam or xanax or xanor or tafil or alprox or frontal, bromazepam or lexotanil or lexotan or lexomil or somalium or bromam, chlordiazepoxide or Librium or tropium or risolid or klopoxid, cinolazepam or gerodorm, clonazepam or klonopin or rivotril or iktorivi, cloxazolam or olcadil, clorazepate or tranxene, diazepam or valium or pax or apzepam or stesolid, estazolam or proSom, flunitrazepam or rohypnol or fluscand or flunipam or rona or rohydorm, flurazepam or dalmadorm or dalmane, flutoprazepam or restas, halazepam or paxipam or ketazolam or anxon or loprazolam or dormonoct, iorazepam or ativan or temesta or tavor, lorabenz, lormetazepam or loramet or noctamid or pronoctan, medazepam or nobrium, midazolam or dormicum or versed or hypnovel or dormonid, nimetazepam or erimin, nitrazepam or mogadon or alodorm or pacisyn or dumolid, nordazepam or madar or stilny, oxazepam or seresta or serax or serenid or serepax or sobril, pinazepam or domar or prazepam or lysanxia or centrax or quazepam or doral, temazepam or restoril or normison or euhypnos or tenox, Tetrazepam or Mylostan or Triazolam or Halcion or Rilamir.

Oral vaccines: Vaccines designed to prevent or reduce the symptoms of diseases of which the following is a representative however not exclusive list: Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Travellers' Diarrhea, Hepatitis A, B and C, Otitis Media, Dengue Fever, Rabies, Parainfluenza, Rubella, Yellow Fever, Dysentery, Legionnaires Disease, *Toxoplasmosis*, Q-Fever, Haemorrhegic Fever, Argentina Haemorrhagic Fever, Caries, Chagas Disease, Urinary Tract Infection caused by *E. coli*, Pneumoccoccal Disease, Mumps, and Chikungunya. Vaccines to prevent or reduce the symptoms of other disease syndromes of which the following is a representative, however not exclusive list of causative organisms: *Vibrio* species, *Salmonella* species, *Bordetella* species, *Haemophilus* species, *Toxoplasmosis gondii*, Cytomegalovirus, *Chlamydia* species, *Streptococcal* species, Norwalk Virus, *Escherischia coli, Helicobacter pylori*, Rotavirus, *Neisseria gonorrhae, Neisseria meningiditis*, Adenovirus, Epstein Barr Virus, Japanese Encephalitis Virus, *Pneumocystis carini*, Herpes simplex, *Clostridia* species, Respiratory Syncytial Virus, *Klebsiella* species, *Shigella* species, *Pseudomonas aeruginosa*, Parvovirus, *Campylobacter* species, *Rickettsia* species, *Varicella zoster, Yersinia* species, Ross River Virus, J. C. Virus, *Rhodococcus equi, Moraxella catarrhalis, Borrelia burgdorferi* and *Pasteurella haemolytica*. Further specific examples include opioids such as fentanyl or midazolam. Vaccines directed to non-infections immuno-modulated disease conditions: such as topical and systematic allergic conditions such as Hayfever, Asthma, Rheumatoid Arthritis and Carcinomas. Vaccines for veterinary use: including those directed to Coccidiosis, Newcastle Disease, Enzootic pneumonia, Feline leukaemia, Atrophic rhinitis, Erysipelas, Foot and Mouth disease, Swine, pneumonia, and other disease conditions and other infections and auto-immune disease conditions affecting companion and farm animals.

Proteins, peptides and recombinant drugs: insulin (hexameric/dimeric/monomeric forms), glucagon, growth hormone (somatotropin), polypeptides or their derivatives, (preferably with a molecular weight from 1000 to 300,000), calcitonins and synthetic modifications thereof, enkephalins, interferons (especially Alpha-2 interferon for treatment of common colds), LHRH and analogues (nafarelin, buserelin, zolidex), GHRH (growth hormone releasing hormone), secretin, bradykin antagonists, GRF (growth releasing factor), THF, TRH (thyrotropin releasing hormone), ACTH analogues, IGF (insulin like growth factors), CGRP (calcitonin gene related peptide), atrial natriurectic peptide, vasopressin and analogues (DDAVP, lypressin), factor VIII, G-CSF (granulocyte-colony stimulating factor), EPO (erythropoitin). Sex hormones: clomiphene citrate, danazol, ethinyloestradiol, medroxyprogesterone acetate, mestranol, methyltestosterone, norethisterone, norgestrel, oestradiol, conjugated oestrogens, progesterone, stanozolol, stiboestrol, testosterone, tibolone. Spermicides: nonoxynol. Stimulants: amphetamine, dexamphetamine, dexfenfluramine, fenfluramine, mazindol, pemoline.

Notwithstanding the general applicability of the method of the invention, more specific examples of bioactive substances include, but are not limited to: haloperidol (dopamine antagonist), DL isoproterenol hydrochloride (.beta.-adrenergic agonist), terfenadine (H1-antagonist), propranolol hydrochloride (.beta.-adrenergic antagonist), desipramine hydrochloride (antidepressant), sildenafil citrate, tadalafil and vardenafil. Minor analgesics (cyclooxygenase inhibitors), fenamic acids, piroxicam, Cox-2 inhibitors, naproxen, and others, may all benefit from being formulated into an oral dosage form of the present invention.

Further examples of bioactive substances include, but are not limited to: alfaxalone, acetyl digoxin, acyclovir analogs, alprostadil, aminofostin, anipamil, antithrombin III, atenolol, azidothymidine, beclobrate, beclomethasone, belomycin, benzocaine and derivatives, beta carotene, beta endorphin, beta interferon, bezafibrate, binovum, biperiden, bromazepam, bromocriptine, bucindolol, buflomedil, bupivacaine, busulfan, cadralazine, camptothesin, canthaxanthin, captopril, carbamazepine, carboprost, cefalexin, cefalotin, cefamandole, cefazedone, cefluoroxime, cefinenoxime, cefoperazone, cefotaxime, cefoxitin, cefsulodin, ceftizoxime, chlorambucil, chromoglycinic acid, ciclonicate, ciglitazone, clonidine, cortexolone, corticosterone, cortisol, cortisone, cyclophosphamide, cyclosporin A and other cyclosporins, cytarabine, desocryptin, desogestrel, dexamethasone esters such as the acetate, dezocine, diazepam, diclofenac, dideoxyadenosine, dideoxyinosine, digitoxin, digoxin, dihydroergotamine, dihydroergotoxin, diltiazem, dopamine antagonists, doxorubicin, econazole, endralazine, enkephalin, enalapril, epoprostenol, estradiol, estramustine, etofibrate, etoposide, factor ix, factor viii, felbamate, fenbendazole, fenofibrate, fexofenedine, flunarizin, flurbiprofen, 5-fluorouracil, flurazepam, fosfomycin, fosmidomycin, furosemide, gallopamil, gamma interferon, gentamicin, gepefrine, gliclazide, glipizide, griseofulvin, haptoglobulin, hepatitis B vaccine, hydralazine, hydrochlorothiazide, hydrocortisone, ibuprofen, ibuproxam, indinavir, indomethacin, iodinated aromatic x-ray contrast agents such as iodamide, ipratropium bromide, ketoconazole, ketoprofen, ketotifen, ketotifen fumarate, K-strophanthin, labetalol, *lactobacillus* vaccine, lidocaine, lidoflazin, lisuride, lisuride hydrogen maleate, lorazepam, lovastatin, mefenamic acid, melphalan, memantin, mesulergin, metergoline, methotrexate, methyl digoxin, methylprednisolone, metronidazole, metisoprenol, metipranolol, metkephamide, metolazone, metoprolol, metoprolol tartrate, miconazole, miconazole nitrate, minoxidil, misonidazol, molsidomin, nadolol, nafiverine, nafazatrom, naproxen, natural insulins, nesapidil, nicardipine, nicorandil, nifedipine, niludipin, nimodipine, nitrazepam, nitrendipine, nitrocamptothesin, 9-nitrocamptothesin, olanzapine, ORG34517, oxazepam, oxprenolol, oxytetracycline, penicillins such as penicillin G benethamine, penecillin O, phenylbutazone, picotamide, pindolol, piposulfan, piretanide, piribedil, piroxicam, pirprofen, plasminogenici activator, prednisolone, prednisone, pregnenolone, procarbacin, procaterol, progesterone, proinsulin, propafenone, propanolol, propentofyllin, propofol, propranolol, raloxifene, rifapentin, simvastatin, semi-synthetic insulins, sobrerol, somastotine and its derivatives, somatropin, stilamine, sulfinalol hydrochloride, sulfinpyrazone, suloctidil, suprofen, sulproston, synthetic insulins, talinolol, taxol, taxotere, testosterone, testosterone propionate, testosterone undecanoate, tetracane HI, tiaramide HCl, tolmetin, tranilast, triquilar, tromantadine HCl, urokinase, valium, verapamil, vidarabine, vidarabine phosphate sodium salt, vinblastine, vinburin, vincamine, vincristine, vindesine, vinpocetine, vitamin A, vitamin E succinate, and X-ray contrast agents.

In addition, it is also expected that new chemical entities (NCE) and other actives for which the solid dosage forms of the present invention are suitable for delivery of will be created or become commercially available in the future and can be used as the bioactive substance.

The biological active material may be an active material that binds to one or more adrenergic receptors. Preferably, the active material that binds to one or more adrenergic receptors is adrenaline (epinephrine), or an adrenaline salt, such as adrenaline bitartrate or adrenaline hydrochloride. Alternatively, the active material that binds to one or more adrenergic receptors may be provided in the form of analogues and compounds related to adrenaline, such as norepinephrine, isoprenaline; or symphatomimetic agents such as tyramine, ephedrine, pseudoephedrine, the amphetamines, salbutamol, and terbutaline.

The bioactive substance may be an N-methyl-D-aspartate receptor antagonist. Preferably, the N-methyl-D-aspartate receptor antagonist is chosen from the list comprising: dextromethorphan, dextrorphan or ketamine.

The bioactive substance may be a cyclic guanosine monophosphate (cGMP) phosphodiesterase type 5 (PDE5) inhibitor. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

Examples of medicaments used for weight loss and treatment of obesity include, but are not limited to, lipase inhibitors (e.g., orlistat), appetite suppressants (e.g., sibutramine, rimonabant, phendimetrazine, diethylpropion, phentermine, bupropio, topiramate, zonisamide), agents that delay gastric emptying (e.g., hormones and their analogs such as exenatide and pramlintide), and metformin. Examples of medicaments used for the treatment of diabetes include, but are not limited to, insulin, sulfonylurea secretagogues (e.g., tolbutamide, acetohexamide, tolazamide, chlorporpamide, glipizide, glyburide, glimepiride, gliclazide), meglitinide secretagogues (e.g., repaglinide, nateglinide), biguanide insulin sensitizers (e.g., metformin), thiazolidinediones (e.g., rosiglitazone, pioglitazone), alpha-glucosidase inhibitors (e.g., miglitol, acarbose), glucagon-like peptide analogs and agonists (e.g., exenatide, liraglutide, taspoglutide), dipeptidyl peptidase-4 inhibitors (e.g., vildagliptin, sitagliptin, saxagliptin), and amylin analogues (e.g., pramlintide). Examples of medicaments used for the treatment of dyslipidemia and hypercholesterolemia include, but are not limited to, statins (e.g., atorvastatin, fluvastatin, lovastatin, pitavastatin, pravastatin, rosuvastatin, simvastatin), cholesterol absorption inhibitors (e.g., ezetimibe), bile acid sequestrants (e.g., cholestyramine, colestipol), fibrates (e.g., fenofibrate, gemifibrozil), and niacin.

In general, medicaments used to treat obesity, diabetes, dyslipidemia, and hypercholesterolemia as described above are also of use in treating aspects of metabolic syndrome. Additional aspects of metabolic syndrome, e.g., hypertension, can be treated with anti-hypertensive medicaments. Examples of medicaments for use in treating hypertension include, but are not limited to, diuretics (e.g., chlorthalidone, hydrochlorothiazide, metolazone, spironolactone, bumetanide), beta blockers (e.g., acebutanol, metoprolol, propranolol, carteolol, timolol), ACE inhibitors (e.g., benazepril, captopril, enalapril, moexipril), angiotensin II receptor blockers (e.g., candesartan, eprosartan, irbesarten, losartin), calcium channel blockers (e.g., amlodipine, diltiazem, nifedipine, verapamil), alpha blockers (e.g., doxazoin, prazosin, terazosin), combined alpha and beta-blockers (e.g., carvedilol, labetolol), central agonists (e.g., alpha methyldopa, clonidine, guanabenz acetate), peripheral adrenergic inhibitors (e.g., resiprine, guanadrel), and vasodilators (e.g., hydralazine, minoxidil).

Power Source

The ingestible drug delivery device including the one or more bioactive substance module and/or deactivation modules configured to be deliver to one or more tissues of a subject to treat the vertebrate subject, and a programmable microprocessor configured to provide instructions to the one or more bioactive substance module and/or deactivation modules in response to information regarding one or more physiological conditions of the subject, can include at least one power source configured to power the components of the device. The device can further include one or more sensors and/or one or more neurostimulators.

The power source can be one or more of a wireless power source. A wireless power source includes stored power, a battery, or a fuel cell. For an implantable device, the power source can be external, internal, or a combination thereof. The implanted device can be coupled to an external power source through a radio-frequency link. Alternatively, the implanted device can include a self-contained power source made using any means of generation or storage of energy, e.g., a primary battery, a replenishable or rechargeable battery, a thin film battery, a capacitor, or a supercapacitor. A replenishable or rechargeable self-contained power source can be replenished or recharged using a radio-frequency link, an optical link, or other energy-coupling link. See, e.g., U.S. Patent Application No. 2005/0143787, by B. Boveja, which is incorporated herein by reference. In an aspect, the power source for an implantable device is supplied from an external power source via a transcutaneous inductive coupling. See, e.g., U.S. Patent Application 2010/0076524, which is incorporated herein by reference.

The power source can include electrical energy generated by mechanical energy of a subject's movement. For example, the power source can be a linear motion electric power generator that uses a rare earth magnet and a coil positioned to move linearly back and forth relative to one another. The movement of the coil in the field of the magnet generates a current in the coil. See, e.g., U.S. Pat. No. 5,347,186, which is incorporated herein by reference. In this instance, power can be generated as the device moves, e.g., bounces up and down while jogging or while doing other physical activity, as exemplified by the nPower® PEG (Personal Energy Generator, from Tremont Electric, Tremont, Ohio). In an aspect, the power source can be one or more solar panel attached to one or more component of the device such as, for example, a portable refrigeration unit in a backpack with affixed solar panels. See, e.g., U.S. Patent Application 2009/0015022 which is incorporated herein by reference.

In an aspect, the power source can include a rubber film configured to harness energy associated with natural body movements. For example, the power source can include a material made of a ceramic piezoelectric material, e.g., fabricated lead zirconate titanate that is embedded in silicone rubber sheets. The rubber film can harness natural body movements such as walking and breathing as electricity when flexed, converting approximately 80% of mechanical energy into electrical energy. See, e.g., Qi, et al., Nano Lett., 10: 524-528, 2010, which is incorporated herein by reference.

The power source can include one or more of a battery or microbattery, a fuel cell or biofuel cell, or a nuclear battery. One or more power sources of the same or different types can be included in the device, without limitation. Batteries for a small implantable device can include a microbattery, e.g., as available from Quallion LLC, Sylmar, Calif. (http://www.quallion.com), or one designed as a film (U.S. Pat. Nos. 5,338,625 and 5,705,293), each of which is incorporated herein by reference. Alternatively, the power source could be one or more fuel cell, for example, a biofuel cell, such as an enzymatic, microbial, or photosynthetic fuel cell (US2003/0152823A1; WO03/106966A2; or Chen T et al., "J. Am. Chem. Soc. 2001, 123: 8630-8631, each of which is incorporated herein by reference). The fuel cell can be of any size, including the micro- or nano-scale. In an aspect, the power source can include laterally packaged piezoelectric fine wires that convert biomechanical energy (e.g., stretching muscles, beating heart, walking) into electrical energy using a nanogenerator. See, e.g., Yang et al., Nature Nanotechnol., 4: 34-39, 2009; Yang et al., Nano Lett., 9: 1201-1205, 2009, each of which is incorporated herein by reference. In another aspect, the power source can include a pressure-rectifying mechanism that utilizes pulsatile changes in blood pressure or an acceleration-rectifying mechanism as used in self-winding watches, or other types of flow-rectifying mechanism capable of deriving energy from other flow parameters. In an embodiment, the power source can be a nuclear battery. See, e.g., Wacharasindhut et al., Appl. Phys. Lett. 2009, 95: 014103, which is incorporated herein by reference.

In an aspect, the power source can be a power receiver capable of receiving power from an acoustic source or electromagnetic source (e.g., infrared energy, or inductively coupled, as described in U.S. Pat. Nos. 6,170,485, and 7,212,110; U.S. Patent Application No. 2005/0228259; and Budgett et al., J. Appl. Physiol. 2007, 102: 1658-1663, each of which is incorporated herein by reference). The power source can include power generated from thermoelectric heating based on the differential between body temperature of a subject and the ambient temperature. See, e.g., U.S. Pat. No. 6,075,199; U.S. Patent Application 2009/0056328, each of which is incorporated herein by reference. In an aspect, the device can include a power transmitter capable of transmitting power (e.g., acoustic power, electrical power, or optical power) from the device to a secondary location. The secondary location can be, for example, one or more bioactive substance module and/or deactivation modules, one or more sensors, another device, or combinations thereof.

Bioactive Substance Module

The release of the bioactive substance can be through a variety of means; osmotic plug piston, polymer cracking or trigger initiated solubilization on the capsule itself or other capsule voids, release from ion-bound linkage from polymer side chains to release the API. Another embodiment of the present invention, one which could be pharmacist controlled is by controlling the release of the active ingredient: release/pump it in the dissolving part of the pill, neutralize/block the active part. The Smart Pill can also be obtained by: sealing the passage to the dissolving part, neutralizing the active part by "cement" it in an inert material and chemically or physically (temperature/light, etc.) neutralize the active ingredient. Another embodiment of the present invention in a pump form which could be controlled for emergencies could also be described like two electrodes in water. The water compartment has a flexible wall. If you start making the water electrolyze you will obtain gases, which will increase the volume and press outward the flexible wall (or a piston). Thus no motor is required in this embodiment.

Deactivation Module

The ingestible drug delivery device of the invention may comprise a deactivation module. In exemplary embodiments, the deactivation module may comprise one or more deactivation agents which may be, for example, a chemical, and enzyme, and/or a pharmaceutical which can serve to deactivate the bioactive substance. In exemplary embodiments the deactivation module may release its contents into the bioactive substance module to deactivate the at least one bioactive substance. In alternative embodiments, the deactivation module may release its content directly into the patient. In certain embodiments the deactivation module may release a substance, such as a pharmaceutical, which is antagonistic to the bioactive substance. In exemplary embodiments, the deactivation module may comprise, for example, an enzyme, a chemical, and/or a pharmaceutical which can serve to deactivate and/or degrade the bioactive substance to prevent the pollution of the environment by inactivating the bioactive substance before excretion to prevent contamination of waste and wastewater effluents before they reach the environment.

Electronics Module

The electronics module may comprise a processor, a transponder and a memory, said memory comprising data selected from the group consisting of:
  (a) data related to a person who is permitted to ingest said ingestible drug medical device;
  (b) data related to said bioactive substance;
  (c) data related to a healthcare provider that enabled said electronics module;
  (d) data related to said sensor;
  (e) data related to the provenance of said ingested drug medical device;
  (f) combinations thereof, Tracking and Delivery Confirmation of Pharmaceutical Products A system and method are disclosed that track an ingestible drug delivery deliverable to a user. The system includes an identifier or tag secured to the deliverable, a computer system for interrogating the identifier, and a personal device in communication with the computer system, wherein the personal device is held by the user at the time the user is administered the deliverable to detect the unique identity associated with the identifier device and confirms delivery of the deliverable to the user. The method includes attaching an identifiable tag that produces a unique signature to the deliverable, interrogating the tag at about the time of delivery to the user, and confirming that the user has been administered the deliverable through detecting the identifiable tag. The system provides that the ingestible drug delivery device of the invention can communicate with each other and/or with a personal device and/or a computer system.

A system and method are disclosed that track a packaged product to a user. The system includes an identifier or tag secured to the deliverable, a computer system or APP for interrogating the identifier, and a personal device in communication with the computer system, wherein the personal device is held by the user at the time the user is administered the deliverable to detect the unique identity associated with the identifier device and confirms delivery of the deliverable, e.g., the ingestible drug delivery device of the invention, to the user. The method includes attaching an identifiable tag that produces a unique signature to the deliverable, interrogating the tag at about the time of delivery to the user, and confirming that the user has been administered the deliverable through detecting the identifiable tag.

Retail Tracking System

Another example of the Invention would be a retail tracking system, which incorporates a digital tag, which may be an attachable device for retail packaging configured for wireless communication with other retail packages with, for example, the devices of the invention. In exemplary embodiments, the smart pill system incorporates this technology. In an exemplary embodiment, the manufacturer of the goods applies the tag as part of or attached to the retail package. The package recognizes and communicates with other packages that are then placed into a shipping box. The box receives a corresponding tag label that tells the in other contents where they will be shipped and by what shipper. This prevents the theft or interception of the contents and maintains a digital signature of the manufacturer, the shipper and the retail establishment that was programmed to receive the goods. If found in the hands of someone who was not the targeted recipient, it can be evidence of the theft.

In an exemplary embodiment, when the box is scanned by the shipper the shipper knows the necessary information for shipping too. Each package knows its size, weight, dimensions, etc., and by communicating with the other packages in the box can also communicate its total contents. The first package that enters the box acts as the master and then retains all information from each subsequent entry to the box as they reach out and communicate with each other.

The box is delivered to the recipient, e.g., a retail establishment. The corresponding APP on the users system (smart phone, tablet, PC, etc.) receives it's communication from the packages that they have arrived. The user then places the desired quantity onto the retail shelves. The packages recognize the quantity placed on the shelf and that they are together. The packages then acknowledge and are aware when each package leaves the shelf as they provide a good bye hand shake to the other packages. All of this communication can be registered and monitored by the User. The last package to leave the shelf communicates with the User that everyone (all the packages) have left the shelf and more are needed from the supply room. The last package will know if the full quantity that was shipped in its box have been depleted or if additional packages are still there ready to be placed on the shelf. When scanned by the cashier the system automatically notifies the APP that the package has left the building and if it is the last one, it also notifies the User that reorders are necessary. It can ask the User if it wants a reorder placed and this can automatically be sent to the manufacturer to expedite the reorder and shipping and replenishment sequence. The system can also be set to varied needs ie: if quantity of packages is down to 6 units . . . re-order. The system is seamless and minimal cost to the retail establishment as it only requires the APP, everything else is provided by the participants of the system. i.e.: the manufacturer of the goods, the shipper, etc.

The Invention makes the package to package communication the key to the entire retail chain of events. It provides a very low cost digital tag which is a part of the retail package when shipped by the manufacturer. It provides continuous communication throughout the packages life cycle and provides a digital signature for every aspect from manufacturer, to shipper, to retailer. It is seamless and can advise the retailer of its life expectance i.e., near expiration date. It can also be tied into a home user APP that provides the consumer with helpful information including but not limited to: recipes, product uses, interaction concerns i.e., never use bleach with ammonia, etc.

In an exemplary embodiment. The digital tag may be attached to the packaging of the ingestible drug delivery devices of the invention. In another exemplary embodiment, the digital tag may be attached to the shipping boxes containing the ingestible drug delivery devices of the invention. In yet another exemplary embodiment, the digital tag may be incorporated into the ingestible drug delivery device itself.

Packaging/Treatment Kits

The present invention relates to a kit for conveniently and effectively carrying out the methods in accordance with the present invention. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose; or an AM dose is packaged with a PM dose. Alternatively, placebo dosages, or vitamin or dietary supplements, either in a form similar to or distinct from the pharmaceutical active dosages, can be included.

In one aspect, the package, kit or container comprises a "blister package" (also called a blister pack, or bubble pack). In one aspect, the blister package consists of two or more separate compartments: AM dosage of this invention, and PM dosage of this invention, or mid-day dosage of this invention. This blister package is made up of two separate material elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising a composition (e.g., a (the multi-ingredient combination of drugs of the invention) combination of active ingredients) of the invention. Blister packs, clamshells or trays can be designed to be non-reclosable, so consumers can tell if a package has already opened. They are used to package for sale goods where product tampering is a consideration, such as the pharmaceuticals of the invention. In one aspect, a blister pack of the invention comprises a moulded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one aspect, a specialized form of a blister pack is a strip pack.

In one aspect, a blister pack also comprises a method of packaging where the compositions comprising combinations of ingredients of the invention are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the invention are used, and they can comprise of two vacuum-formed PVC sheets meshed together at the edges, with the informative card inside.

In one aspect, blister packaging comprises at least two components (e.g., is a multi-ingredient combination of drugs of the invention): a thermoformed "blister" which houses the product (e.g., a pharmaceutical combination of the invention), and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or large. Conventional blister packs can also be sealed (e.g., using an AERGO 8 DUO®, SCA Consumer Packaging, Inc., DeKalb, Ill.) using regular heat seal tooling. This alternative aspect, using heat seal tooling, can seal common types of thermoformed packaging.

As discussed herein, the products of manufacture of the invention can comprise the packaging of the ingestible drug delivery devices of the invention, alone or in combination, as "blister packages" or as a plurality of packettes, including as lidded blister packages, lidded blister or blister card or packets, or a shrink wrap.

Other means for containing said ingestible drug delivery devices can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

Another drug delivery system comprises one or more ball semiconductor aggregations and facilitating release of a drug stored in a reservoir. The first aggregate is used for sensing and memory, and a second aggregation for control aspects, such as for pumping and dispensing of the drug. The system may communicate with a remote control system, or operate independently on local power over a long period for delivery of the drug based upon a request of the patient, timed-release under control by the system, or delivery in accordance with measured markers. See U.S. Pat. No. 6,464,687, incorporated herein by reference in its entirety.

EXAMPLES

The invention will be illustrated in more detail with reference to the following Examples, but it should be understood that the present invention is not deemed to be limited thereto.

Example 1

Typical Route from Manufacturer to Drug Release

The purpose is to illustrate how the above described system combine to have a secure, traceable and [as much as possible] safe delivery of the drug, for example a single pill dosage. The two pill dosages can be implemented and also "avoid" mixing drug schemes are envisaged.

The manufacturer doses the drug in the pill and activates it. This activity comprises several steps:
  reads the pill ID and associate all the drug information to it in the database
  enables the pill by issuing the enable security flag command enable F1 (P1,R1), which will change the status of the first security layer (flag). The pill will at first verify that the F0 is correct and only after apply the change as mandated by the multilevel security system policy.

The pills are sent to pharmacies. The database will register the pharmacies that received the pill.
  The pharmacist prepares the prescription:
  it uses a special terminal with unique TERM ID over the secure communication network
  reads the pill PID
  obtains from the server a challenging-response (P1, R1)
  issues a get F13-F15 (P1,R1) command to verify any tampering attempt.
  the pill verifies first the F0 and then F1 to see if the pill was activated by the manufacturer as mandated by the multilevel security system policy; if correct it continues, otherwise it stops issuing an error message; if the F1 layer is enabled it computes the result R of M1 using S1 and P. If R is the same of R1, it considers the command legitimate, and returns F13-F15 if it didn't arrive to the maximum allowed number, otherwise issue a pill disabled due to tampering message which is sent to the manufacturer. In this case the pill becomes unusable.

after receiving the F13-F15 response the terminal obtains another challenging-response (P2, R2)

issues a enable F2 (P2,R2) command the pill verifies first the F1 to see if the pill was activated by the manufacturer; if correct it continues, otherwise it stops issuing an error message; if the F1 layer is enabled it computes the result R of M1 using S1 and P2. If R is the same of R2, it considers the command legitimate, changes the status of F2 and issues an acknowledge message. The result is stored on the database.

Similar the terminal might issue an enable F3 command if a timer is envisaged. The logic follows the one described above. (see "Patient terminal" section).

If a user terminal is envisaged, the pharmacist will communicate the user's TERM ID to the manufacturer to be associated with the pill ID.

The user terminal will similarly exchange information with the pill and manufacturer and enable F3B security layer (first verifying the activation of F1, F2, F3 and the anti tampering counter F13-F15).

The pill gets ingested.

The sensors in the pill confirm that it was ingested (in the simplest case by temperature, liquid sensor and time). At this point it will initiate an over dose verification. If the result is ok will enable F12.

The drug release watch dog will verify the F0-F15 status and if it matches the expected result will enable the drug release command, and change the F0 to 0 (pill terminated).

While the invention has been described in detail and with reference to specific examples thereof, it will be apparent to one skilled in the art that various changes and modifications can be made therein without departing from the spirit and scope thereof.

What is claimed is:

1. A method for treating or preventing addiction, addiction induced anxiety, and/or withdrawal symptoms wherein said method comprises:
    (a) forming an ingestible drug delivery device by a device manufacturer, said ingestible drug delivery device comprising:
      a capsule body comprising:
      a sensor for sensing at least one biologic condition within a patient;
      a bioactive substance module comprising a container for holding a volume and/or quantity of bioactive substance therein and a microactuator for dispensing said bioactive substance from said container to a location outside of said capsule body, wherein said bioactive substance is at least one glucocorticoid receptor antagonist in a therapeutically effective amount;
      an electronics module, coupled to said sensor and said bioactive substance module, said electronics module comprising a processor, a transponder and a memory, said memory configured for storing data related to said bioactive substance and data received in signals from said sensor;
      a power source coupled to said sensor, said bioactive substance module and said electronics module;
    (b) establishing a unique device ID in said memory by the manufacturer and setting a first flag in said memory by the manufacturer;
    (c) conveying said ingestible drug delivery device to a pharmacist, the pharmacist communicating with said ingestible drug delivery device using a programming terminal to store data related to the pharmacist and a patient ID authorized to ingest said ingestible drug delivery device in said memory and to set a second flag in said memory;
    (d) administering said ingestible drug delivery device to the patient based on need of treatment of addiction, addiction induced anxiety and/or withdrawal from narcotics symptoms, the patient having a patient interface device that communicates with said ingestible drug delivery device to provide a patient ID to said ingestible drug delivery device;
    (e) analyzing, by said processor, to determine:
      (i) that said first flag is set;
      (ii) that said second flag is set; and
      (iii) that said patient ID provided by said patient interface device matches said patient ID provided by the pharmacist; and
    (f) dispensing said at least one bioactive substance to the patient only if said first and second flags are set and said patient ID provided by said patient interface device matches said patient ID provided by the pharmacist and disabling the dispensing of said at least one bioactive substance if either one of said first or second flags is not set or if no match is determined by said processor between said patient ID provided by said patient interface device and said patient ID provided by the pharmacist; and
    wherein addiction, addiction induced anxiety, and/or withdrawal symptoms are treated and/or prevented in the patient.

2. The method, according to claim 1, wherein the at least one glucocorticoid receptor antagonist is in a pharmaceutical preparation.

3. The method of claim 1, wherein the glucocorticoid receptor antagonist is selected from the group consisting of ORG 34517, 11-(substituted phenyl)-estra-4,9-diene derivatives, and 11-(substituted phenyl)-estra-4,9-diene derivatives of formula I

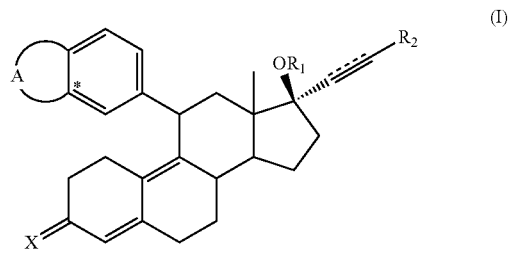

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H, OH), O, and NOH; and the interrupted line represents an optional bond.

4. The method of claim 1 wherein the GCR antagonist is ORG34517.

5. A method of treating or preventing addiction, addiction induced anxiety, and/or withdrawal symptoms in a patient in need thereof, comprising:
(a) forming an ingestible drug delivery device by a device manufacturer, said ingestible drug delivery device comprising:
a capsule body comprising:
a sensor for sensing at least one biologic condition within a patient;
a bioactive substance module comprising a container for holding a volume and/or quantity of bioactive substance therein and a microactuator for dispensing said bioactive substance from said container to a location outside of said capsule body;
an electronics module, coupled to said sensor and said bioactive substance module, said electronics module comprising a processor, a transponder and a memory, said memory configured for storing data related to said bioactive substance and data received in signals from said sensor;
a power source coupled to said sensor, said bioactive substance module and said electronics module;
(b) establishing a unique device ID in said memory by the manufacturer and setting a first flag in said memory by the manufacturer;
(c) conveying said ingestible drug delivery device to a pharmacist, the pharmacist communicating with said ingestible drug delivery device using a programming terminal to store data related to the pharmacist and a patient ID authorized to ingest said ingestible drug delivery device in said memory and to set a second flag in said memory; and wherein said bioactive substance is a composition comprising:
i) a first therapeutic agent which is a GCR antagonist, or pharmaceutically acceptable salts thereof;
ii) at least one or possibly more additional therapeutic agent(s) selected from the group consisting of anxiolytics, antidepressants, neuroleptics, or other psychotropic medications and combinations thereof; and
iii) at least one pharmaceutically acceptable carrier, wherein the first and second therapeutic agents are each present in an amount which, in combination, is a therapeutically effective amount for treating or preventing addiction, addiction induced anxiety, and/or withdrawal symptoms;
(d) administering the ingestible drug delivery device to the patient based on need of treatment of addiction, addiction induced anxiety and/or withdrawal from narcotics symptoms, the patient having a patient interface device that communicates with said ingestible drug delivery device to provide a patient ID to said ingestible drug delivery device;
(e) analyzing, by said processor, to determine:
(iv) that said first flag is set;
(v) that said second flag is set; and
(vi) that said patient ID provided by said patient interface device matches said patient ID provided by the pharmacist; and
(f) dispensing said at least one bioactive substance to the patient only if said first and second flags are set and said patient ID provided by said patient interface device matches said patient ID provided by the pharmacist and disabling the dispensing of said at least one bioactive substance if either one of said first or second flags is not set or if no match is determined by said processor between said patient ID provided by said patient interface device and said patient ID provided by the pharmacist; and
wherein addiction, addiction induced anxiety, and/or withdrawal symptoms are treated and/or prevented in the patient.

6. The method of claim 5 wherein the second therapeutic agent is selected from the group consisting of at least one anti-anxiety drug, at least one anti-depressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one anti-depressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof.

7. The method of claim 5, wherein the GCR antagonist is selected from the group consisting of ORG 34517, 11-(substituted phenyl)-estra-4,9-diene derivatives, and 11-(substituted phenyl)-estra-4,9-diene derivatives of formula I

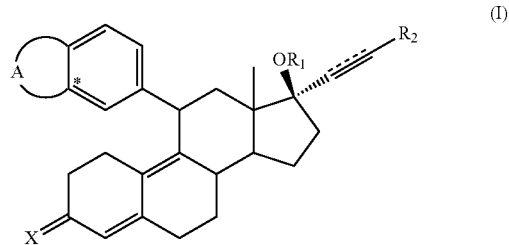

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H, OH), O, and NOH; and the interrupted line represents an optional bond.

8. The method of claim 5 wherein the GCR antagonist is ORG34517.

* * * * *